United States Patent
Koren et al.

(10) Patent No.: US 11,185,495 B2
(45) Date of Patent: Nov. 30, 2021

(54) FINISHED FIBROUS STRUCTURES AND METHODS OF THEIR USE AND PREPARATION

(71) Applicant: Clexio Biosciences Ltd., Jerusalem (IL)

(72) Inventors: Erez Koren, Ramat HaSharon (IL); Itzhak Shalev, Beit Gamliel (IL); Mark Zamansky, Givat Shaul (IL)

(73) Assignee: CLEXIO BIOSCIENCES LTD., Jerusalem (IL)

( * ) Notice: Subject to any disclaimer, the term of this patent is extended or adjusted under 35 U.S.C. 154(b) by 0 days.

(21) Appl. No.: 16/178,147

(22) Filed: Nov. 1, 2018

(65) Prior Publication Data

US 2019/0133929 A1 May 9, 2019

Related U.S. Application Data

(60) Provisional application No. 62/583,835, filed on Nov. 9, 2017, provisional application No. 62/579,987, filed on Nov. 1, 2017.

(51) Int. Cl.

| | |
|---|---|
| *A61K 9/00* | (2006.01) |
| *A61K 9/70* | (2006.01) |
| *A61K 31/4174* | (2006.01) |
| *D06M 16/00* | (2006.01) |
| *A61K 31/196* | (2006.01) |
| *A61K 31/192* | (2006.01) |
| *A61P 23/02* | (2006.01) |
| *A61P 17/06* | (2006.01) |
| *A61P 37/08* | (2006.01) |
| *A61P 25/00* | (2006.01) |
| *A61P 29/00* | (2006.01) |
| *A61P 31/10* | (2006.01) |
| *A61K 31/167* | (2006.01) |
| *A61F 13/00* | (2006.01) |
| *A61K 47/10* | (2017.01) |
| *A61K 47/26* | (2006.01) |
| *A61L 15/44* | (2006.01) |

(52) U.S. Cl.
CPC ...... *A61K 9/0014* (2013.01); *A61F 13/00008* (2013.01); *A61F 13/00063* (2013.01); *A61K 9/703* (2013.01); *A61K 9/7007* (2013.01); *A61K 31/167* (2013.01); *A61K 31/192* (2013.01); *A61K 31/196* (2013.01); *A61K 31/4174* (2013.01); *A61K 47/10* (2013.01); *A61K 47/26* (2013.01); *A61P 17/06* (2018.01); *A61P 23/02* (2018.01); *A61P 25/00* (2018.01); *A61P 29/00* (2018.01); *A61P 31/10* (2018.01); *A61P 37/08* (2018.01); *D06M 16/00* (2013.01); *A61L 15/44* (2013.01)

(58) Field of Classification Search
CPC .......... A61F 13/00008; A61F 13/00063; A61F 2013/00863; A61K 31/167; A61K 31/192; A61K 31/196; A61K 31/4174; A61K 47/10; A61K 47/26; A61K 9/0014; A61K 9/7007; A61K 9/703; A61L 15/44; A61P 17/06; A61P 23/02; A61P 25/00; A61P 29/00; A61P 31/10; A61P 37/08; D06M 16/00; A61M 35/00; A61M 35/10

See application file for complete search history.

(56) References Cited

U.S. PATENT DOCUMENTS

| | | | |
|---|---|---|---|
| 128,385 | A | 6/1872 | Goffinet |
| 2,772,999 | A | 12/1956 | Masci et al. |
| 3,052,237 | A | 9/1962 | Chand |
| 3,058,881 | A | 10/1962 | Wilde |
| 3,082,118 | A | 3/1963 | Shaw et al. |
| 3,140,227 | A | 7/1964 | Roth et al. |
| 3,200,035 | A | 8/1965 | Henry et al. |
| 3,227,614 | A | 1/1966 | Scheuer |
| 3,287,222 | A | 11/1966 | Raymond et al. |
| 3,328,259 | A | 6/1967 | Anderson |
| 3,720,037 | A | 3/1973 | Jones |
| 4,466,431 | A | 8/1984 | Tharrat et al. |
| 4,891,228 | A | 1/1990 | Thaman et al. |
| 5,152,996 | A | 10/1992 | Corey et al. |
| 5,234,957 | A | 8/1993 | Mantelle |
| 5,536,263 | A | 7/1996 | Rolf et al. |
| 5,919,471 | A | 7/1999 | Saferstein et al. |
| 6,258,368 | B1 | 7/2001 | Beerse et al. |
| 6,482,424 | B1 | 11/2002 | Gabbay |
| 7,485,111 | B1 | 2/2009 | Choi et al. |
| 7,785,376 | B1 | 8/2010 | Chun et al. |
| 9,956,387 | B2 | 5/2018 | Brown |
| 2001/0055651 | A1* | 12/2001 | Mao ............... D06M 13/144 427/434.6 |

(Continued)

FOREIGN PATENT DOCUMENTS

| | | |
|---|---|---|
| CN | 102485995 A | 6/2012 |
| EP | 0395476 A2 | 10/1990 |

(Continued)

OTHER PUBLICATIONS

English machine translation of EP1353002A2 made Jun. 2019. (Year: 2019).*
English machine translation of WO2008/068418A2 made Jun. 2019. (Year: 2019).*
English machine translation of ES-2518765-B2 made Apr. 6, 2020. (Year: 2020).*
Aspland, J R., A Series on Dyeing, Chapter 10: The Application of Ionic Dyes to Ionic Fibers: Nylon, Silk and Wool and Their Sorption of Anions; vol. 25, No. 2, Feb. 22-26, 1993.
Daunton, et al., A history of materials and practices for wound management; vol. 20, No. 4, Nov. 2012, pp. 174-186.
Koh, Joonseok, Dyeing with Disperse Dyes, Konkuk University, South Korea, ISBN 978-953-307-565-5; Dec. 2011, pp. 195-220.
Povidone Iodine Prep Pads—povidone iodine prep pads cloth Custom Kits Company Inc; Dec. 2017; 4 pages.

(Continued)

*Primary Examiner* — Michael B. Pallay
(74) *Attorney, Agent, or Firm* — BakerHostetler

(57) ABSTRACT

The disclosure is directed to fibrous structures finished with active pharmaceutical ingredients, as well as methods of their manufacturer and use.

20 Claims, 27 Drawing Sheets

(56) References Cited

U.S. PATENT DOCUMENTS

| | | | | |
|---|---|---|---|---|
| 2003/0013369 | A1* | 1/2003 | Soane | D06M 16/00 |
| | | | | 442/181 |
| 2006/0147504 | A1* | 7/2006 | Corry | A61P 17/00 |
| | | | | 424/443 |
| 2008/0102217 | A1* | 5/2008 | Lin | A01N 43/16 |
| | | | | 427/389.9 |
| 2009/0220612 | A1 | 9/2009 | Perera | |
| 2010/0058973 | A1* | 3/2010 | Beauge-Duguet | A61K 8/11 |
| | | | | 116/201 |
| 2011/0045041 | A1* | 2/2011 | Golubovic-Liakopoulos | |
| | | | | A61K 8/0208 |
| | | | | 424/401 |
| 2012/0192272 | A1 | 7/2012 | Hentunen | |
| 2013/0012892 | A1* | 1/2013 | Brown | A41D 27/00 |
| | | | | 604/290 |
| 2013/0064876 | A1* | 3/2013 | Viladot Petit | A61K 8/11 |
| | | | | 424/443 |
| 2013/0344122 | A1 | 12/2013 | Isaac et al. | |
| 2014/0271863 | A1* | 9/2014 | Anderson | A61K 47/32 |
| | | | | 424/486 |
| 2015/0110851 | A1 | 4/2015 | Haley | |
| 2015/0110852 | A1 | 4/2015 | Zhang | |
| 2016/0101114 | A1 | 4/2016 | Lacouture et al. | |
| 2016/0324872 | A1 | 11/2016 | Bruce et al. | |
| 2016/0346223 | A1 | 12/2016 | Fisch | |

FOREIGN PATENT DOCUMENTS

| | | | | |
|---|---|---|---|---|
| EP | 1353002 | A2 * | 10/2003 | D06B 1/00 |
| EP | 2443925 | A1 | 4/2012 | |
| ES | 2518765 | B2 * | 3/2015 | D06M 16/00 |
| GB | 0494964 | A | 11/1938 | |
| GB | 0697145 | A | 9/1953 | |
| GB | 0845841 | A | 8/1960 | |
| JP | 2012-097070 | A | 5/2012 | |
| WO | WO-2008068418 | A2 * | 6/2008 | A61K 8/11 |

OTHER PUBLICATIONS

Radu, et al., Comparative Study of a Drug Release from a Textile to Skin, Journal of Pharmaceutics & Drug Delivery Research, vol. 4, Issue 2, 1000134, 8 pages.

Schuster, et al., Drug Delivery Systems: Textile Structures with Active Ingredients; Kunststoffe international Feb. 2012; pp. 43-46.

Wienforth, et al., Smart Textiles: A New Drug Delivery System for Symptomatic Treatment of a Common Cold; J Clin Pharmacol 2007; 47:653-659.

Zhu, Chap 9, Drug delivery systems using biotextiles; Biotextiles as Medical Implants, Woodhead Publishing Series in Textiles, 2013, 213-231.

Certified English machine translation of EP 1353002A2 dated Mar. 12, 2020.

Cayman Chemical, Product Information, β-Endorphin (human) (trifluoroacetate salt) Item No. 24955, Oct. 1, 2019, 1 page.

Hollósi et al., Studies on the conformation of β-endorphin and its constituent fragments in water and trifluoroethanol by CD spectroscopy, FEBS letters. Mar. 1, 1977;74(2):185-189.

Phoenix Pharmaceuticals, Inc., Technical Sequence—Endorphin, beta (Equine) Catalog# 022-09, https://www.phoenixpeptide.com/products/view/Peptides/022-09, accessed online Jun. 1, 2020, 1 page.

Sigma-Aldrich, Product Specification, Product Name: β-Endorphin human—>95% (HPLC), Product No. E6261, https://www.sigmaaldrich.com/catalog/product/sigma/e6261?lang=en&region=US, accessed online Jun. 1, 2020, 1 page.

Taylor et al., The structural characterization of β-endorphin and related peptide hormones and neurotransmitters, Pharmacological reviews, Dec. 1, 1986;38(4):291-319.

Yang et al., Conformation of β-endorphin and β-lipotropin: formation of helical structure in methanol and sodium dodecyl sulfate solutions, Proceedings of the National Academy of Sciences, Aug. 1, 1977;74(8):3235-3238.

* cited by examiner

A

B

C

D

FINISHED FIBROUS STRUCTURES AND METHODS OF THEIR USE AND PREPARATION

CROSS REFERENCE TO RELATED APPLICATIONS

This application claims the benefit of U.S. Provisional Application No. 62/579,987, filed Nov. 1, 2017, and U.S. Provisional Application No. 62/583,835, filed Nov. 9, 2017, the entireties of which are incorporated by reference herein.

TECHNICAL FIELD

The disclosure is directed to fibrous structures finished with active pharmaceutical ingredients, as well as methods of their manufacturer and use.

BACKGROUND

The transdermal and dermal administration of active pharmaceutical ingredients is known. Transdermal and dermal formulations include, for example, gels, creams, sprays, and lotions that are applied to the skin. Other formulations include patches that are affixed to the skin using an adhesive. While these formulations are useful, there are occasions where a gel, cream, spray, ointment, foam or lotion might be too messy or greasy, resulting in a significant amount of the formulation being transferred away from the skin. In addition, in order to maintain efficacy, these types of formulations required two, three, or more applications, per day. A disadvantage of patch formulations, which is due to their inflexibility, is that there are areas of the body wherein a patch does not adhere well, for example on joint areas or areas having skin-to skin contact such as between fingers or toes. Patch use can also be limited to those areas with intact skin or non-irritable skin, since the adhesives can make removal damaging and/or painful.

Dyeing is a time honored, mature technology of aqueous application of color to fibrous structures, mainly using synthetic organic dyes and frequently at elevated temperatures and pressures in some of the steps. It is generally accepted that there is no dye which dyes all existing fibers and no fiber which can be dyed by all known dyes. The interaction between the dye and the fiber is related to their different chemical and physical characteristics. The desired interaction is dictated by the two main goals of textile dyeing technology, namely to obtain some affinity of the dyestuff to the fiber to promote transfer from the solvent medium to the fiber and to obtain a fixation of the dye to the fiber in order to achieve extraction resistance, known in the art as fastness. During dyeing, the dyes, possibly along with chemical aids such as surfactants, acids, alkali/bases, electrolytes, carriers, leveling agents, promoting agents, chelating agents, emulsifying oils, softening agents etc. . . . are applied to the textile to obtain a uniform depth of color and the color fastness properties suitable for the end use. Usually, this means satisfactory fastness to laundry, soaking, perspiration and abrasion. The dyeing process includes dispersion of the dye in the aqueous media, diffusion of the dye in the liquid phase followed by adsorption onto the outer surface of the fibers and finally diffusion and adsorption to the inner bulk of the fibers. Fastness properties are always required to render the textile fit for use. Surface coloration can also be accomplished by applying pigments (pigments differ from dyes by not showing chemical or physical affinity for the fibers) together with adhesives (polymers which fix the pigment to the fibers). This process is also common in textile printing.

The long established technology of dyeing of hydrophobic fibers with disperse dyes, is a good example of a commercial application of a non-soluble material to a fibrous substrate, which is well known to those versed in the art. Disperse dyes are stable, chemically inert pigments that can be milled to micron size to enhance their dispensability and dispersion stability, so that phase separation and/or aggregation and/or crystallization is minimal. The maximum amount of dye weight per fiber weight add-on required to obtain deep shades is usually under 10% (w/w). Disperse dyes diffuse into the polymer matrix and are therefore very durable to aqueous extraction. The relatively low add-on and full penetration into the polymer matrix result in minimal impact on the textile's functional and aesthetic properties. Such commercially practiced procedures are inadequate however to produce a useful finishing of a textile substrate with an active pharmaceutical ingredient (API). APIs are chemically active compounds which are typically both pH and heat sensitive and have a strong tendency to form large crystalline structures and phase separate from a dispersion or emulsion. Additionally, add-ons that exceed 10% (w/w) are usually required to obtain the desired therapeutic effects. Furthermore, the durability to extraction, sought in conventional practiced procedures, is actually a negative property for the purpose of transferring the API to the patient.

New methods for transdermally and dermally administering active pharmaceutical ingredients are needed.

SUMMARY

The disclosure is directed to non-occlusive, pharmaceutical fibrous structures finished with an active pharmaceutical ingredient, or pharmaceutically acceptable salt thereof. Methods of making and using the finished, non-occlusive, pharmaceutical fibrous structures are also described.

BRIEF DESCRIPTION OF THE DRAWINGS

FIG. 19 depicts stiffness with increasing percentage of Add-on.

FIG. 20A depicts force peak with increasing percentage Add-on.

FIG. 20B depicts percentage strain peak with increasing percentage Add-on.

DETAILED DESCRIPTION OF ILLUSTRATIVE EMBODIMENTS

Figure 1A:
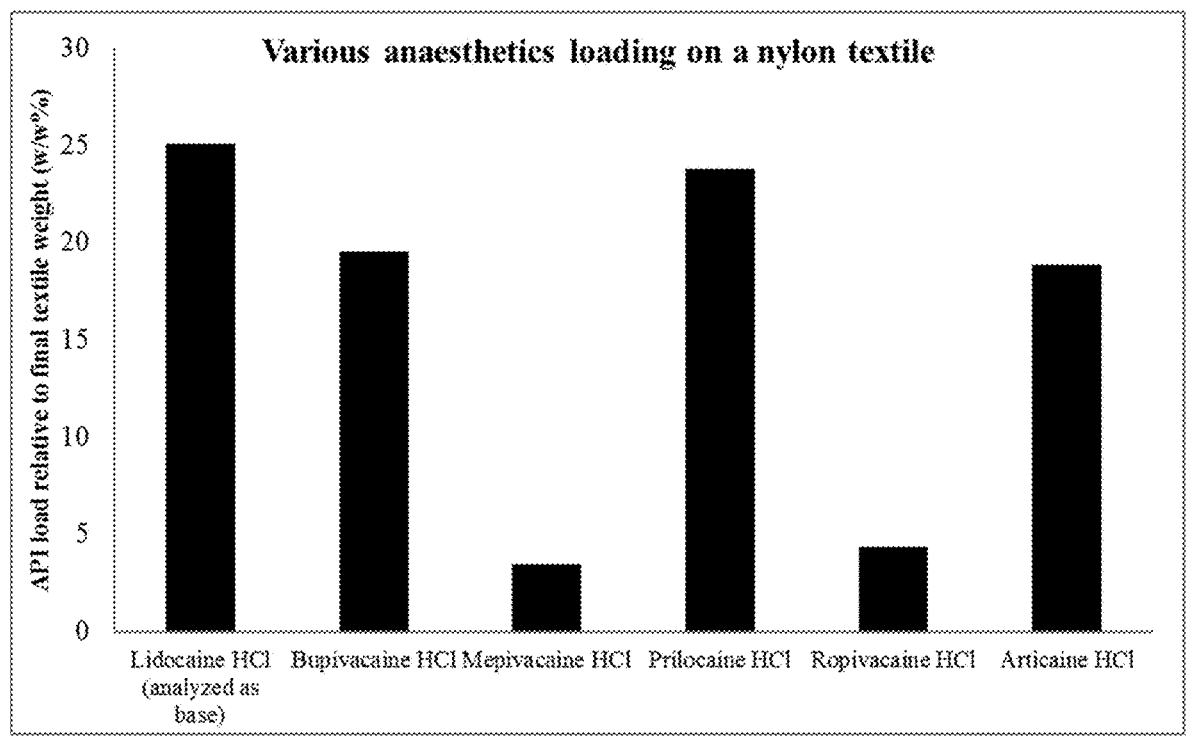
FIG. 1A depicts final fibrous structure weight as compared to original fibrous structure weight, prepared using methods of the disclosure.

The present disclosure may be understood more readily by reference to the following detailed description taken in connection with the accompanying figures and examples, which form a part of this disclosure. It is to be understood that this disclosure is not limited to the specific compositions or methods described and/or shown herein, and that the terminology used herein is for the purpose of describing particular embodiments by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. All ranges are inclusive and combinable.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any sub-combination. Further, reference to values stated in ranges includes each and every value within that range.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Subject" includes both humans and other mammals, including large and small animals such as dogs, cats, rabbits, horses, cows, pigs, and the like. The terms "patient" and "subject" are used interchangeably herein. Preferably, the subject is a human.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" of any disease or disorder refers to ameliorating at least one physical parameter, which may not be discernible by the subject. In yet another embodiment, "treating" or "treatment" of any disease or disorder refers to modulating the disease or disorder, either physically, (e.g., stabilization of a discernible symptom), physiologically, (e.g., stabilization of a physical parameter), or both. In yet another embodiment, "treating" or "treatment" of any disease or disorder refers to delaying the onset of the disease or disorder.

"Hypoallergenic," as used herein, refers to a product of the disclosure that is unlikely to elicit an allergy response in a subject exposed to the product.

"Non-irritant," as used herein, refers to a product of the disclosure that is unlikely to elicit an inflammatory and/or painful response in a subject exposed to the product.

"Therapeutically effective amount" as used herein refers to an amount of active pharmaceutical ingredient effective to exert the intended therapeutic action in a subject.

According to the disclosure, "finishing" is a process (i.e., a treatment) whereby one or more materials are caused to interact with a fibrous structure both by diffusion into the polymer comprising the fibers and/or by deposition onto the surfaces of the fibers and/or the interstices between the fibers.

According to the disclosure, "fibrous structures" are structures composed of either loose fibers, yarns, fabric (e.g., woven, knit, braided or non-woven fabrics) and comprised of natural fibers, manmade fibers, synthetic fibers, or mixtures thereof. In some embodiments, the fibrous structure is a woven fibrous structure comprised of natural fibers, manmade fibers, synthetic fibers, or mixtures thereof. In other embodiments, the fibrous structure is knit fibrous structure comprised of natural fibers, manmade fibers, synthetic fibers, or mixtures thereof. In other embodiments, the fibrous structure is non-woven fibrous structure comprised of natural fibers, manmade fibers, synthetic fibers, or mixtures thereof. The term "fibrous structures" is understood to relate to loose fibers, yarns, fabrics, garments and other such complete textiles.

Applying a substance to a fibrous structure, often referred to as "finishing," is a complex endeavor. Usually, the process is described in terms of interconnected, yet independently controlled steps: homogeneous dispersion of the substance in a liquid medium which can flow around and contact all the fiber surfaces of the structure, migration of the dispersed substance particles from the dispersion's bulk onto the fiber surfaces, interaction of the particles with the fiber surfaces, and optionally, diffusion of the particles into the polymer matrix of the fiber and, finally, fixation of the substance in the fibrous structure to prevent it from being easily detached, once the process is completed.

Homogeneous dispersion requires a suitable solvent to create a true solution. Alternately, if the substance is insoluble in the chosen solvent, then a stable colloid must be created by reduction of particle size and judicious use of surfactants, wetting agents, and stabilizers. Separation, sedimentation, crystallization, and aggregation should be prevented. Preferential migration of the substance onto the fiber surfaces requires an affinity to exist between the dispersed particles and the fibers. This affinity may be ionic, electrostatic, polar, Van der Waals, or hydrophobic/hydrophobic interaction. Affinity is required for an efficient process, otherwise much of the substance will remain in the bulk of the dispersion. Affinity cannot be too strong or an un-level finish may result. Once in contact with the fiber surface, the substance must preferentially interact with it, otherwise, it will randomly return to the dispersion bulk. Penetration of the substance into the fiber's polymer matrix depends on its ability to diffuse into the specific polymer. Fixation also depends on the chemical and physical characters of the substance and polymer.

There are many variables and multiple combinations of the variables which can affect the successful completion of a finishing process. A specific method must be developed for each unique fiber-substance pair. The chemical and physical characteristics of the substance and fiber involved affect the types of possible interactions and their response to process variables such as time, temperature, pressure, pH, ionic strength, solubility, presence and concentration of excipients, agitation, and sequence of the process steps. Those skilled in the art, guided by the present disclosure and examples, would understand that these are the variables that would be identified to establish the procedural conditions needed to practice the inventions.

The disclosure is directed to non-occlusive, pharmaceutical fibrous structures finished with an active pharmaceutical ingredient, or a pharmaceutically acceptable salt thereof. The disclosure is also directed to, among other things, methods of finishing a fibrous structure with an active pharmaceutical ingredient, as well as the finished fibrous structures produced according to the described methods.

These non-occlusive structures permit the passage of air, moisture vapor, and heat through the structure. In some aspects, the non-occlusive structures include a plurality of open pores that permit the passage of air, moisture vapor, and heat through the structure. The non-occlusive structures of the disclosure are in contrast to occlusive structures (e.g., structures having an oleophilic finish) which do not permit the passage of air, moisture vapor, and heat.

In preferred aspects, the non-occlusive, pharmaceutical fibrous structures of the disclosure are hypoallergenic. In other aspects, the non-occlusive, pharmaceutical fibrous structures are non-irritant. In other aspects, the non-occlusive, pharmaceutical fibrous structures of the disclosure are substantially non-adhesive to a subject's skin. In some aspects, the non-adhesive structures are non-tacky at ambient temperature or above. In some aspects, the non-adhesive structures may be devoid of any adhesive material, i.e., the structures do not comprise any material that is tacky at ambient temperature or above. In other aspects, the non-adhesive structure may comprise a material that is tacky at ambient temperature and above, but the amount of that material is insufficient to confer tackiness to the structure at ambient temperature or above.

According to the disclosure, the non-occlusive, pharmaceutical fibrous structures can be used to administer an active pharmaceutical ingredient to a subject. In these methods, the non-occlusive, pharmaceutical fibrous structure is topically applied to the intact skin of the subject. "Intact skin" refers to skin in which there are no breaks, scrapes, cuts, or abnormal openings. According to the disclosure, the non-occlusive, pharmaceutical fibrous structure is topically applied to the intact skin of the subject for a time sufficient to locally or systemically, or both, administer a therapeutically effective amount of the active pharmaceutical ingredient to the subject. In some aspects, the non-occlusive, pharmaceutical fibrous structure is topically applied to the intact skin of the subject for a time sufficient to locally administer a therapeutically effective amount of the active pharmaceutical ingredient to the subject. In some aspects, the non-occlusive, pharmaceutical fibrous structure is topically applied to the intact skin of the subject for a time sufficient to systemically administer a therapeutically effective amount of the active pharmaceutical ingredient to the subject. In some aspects, the non-occlusive, pharmaceutical fibrous structure is topically applied to the intact skin of the subject for a time sufficient to locally and systemically administer a therapeutically effective amount of the active pharmaceutical ingredient to the subject.

In some aspects, the non-occlusive, pharmaceutical fibrous structure is topically applied to the subject's intact skin for a time period of about 1 hour to about 72 hours. In some aspects, the non-occlusive, pharmaceutical fibrous structure is topically applied to the subject's intact skin for a time period of about 8 hours to about 72 hours. In some aspects, the non-occlusive, pharmaceutical fibrous structure is topically applied to the subject's intact skin for a time period of about 24 hours to about 72 hours. In some aspects, the non-occlusive, pharmaceutical fibrous structure is topically applied to the subject's intact skin for a time period of about 48 hours to about 72 hours. In some aspects, the non-occlusive, pharmaceutical fibrous structure is topically applied to the subject's intact skin for a time period of about 4 days. In some aspects, the non-occlusive, pharmaceutical fibrous structure is topically applied to the subject's intact skin for a time period of about 5 days. In some aspects, the non-occlusive, pharmaceutical fibrous structure is topically applied to the subject's intact skin for a time period of about 6 days. In some aspects, the non-occlusive, pharmaceutical fibrous structure is topically applied to the subject's intact skin for a time period of about 7 days.

In some aspects, the therapeutically effective amount of the active pharmaceutical ingredient is administered to the subject throughout the time period. That is, plasma levels sufficient to treat the subject's condition (either locally, systemically, or both) are substantially consistent throughout the time period. In some aspects, the therapeutically effective amount of the active pharmaceutical ingredient is administered to the subject for about 1 hour to about 72 hours. In some aspects, the therapeutically effective amount of the active pharmaceutical ingredient is administered to the subject for about 8 hours to about 72 hours. In some aspects, the therapeutically effective amount of the active pharmaceutical ingredient is administered to the subject for about 24 hours to about 72 hours. In some aspects, the therapeutically effective amount of the active pharmaceutical ingredient is administered to the subject for about 48 hours to about 72 hours. In some aspects, the therapeutically effective amount of the active pharmaceutical ingredient is administered to the subject for about 1, 2, 3, 4, 5, 6, 7, 8, 9, 10, 11, 12, 13, 14, 15, 16, 17, 18, 19, 20, 21, 22, 23, or about 24 hours. In some aspects, the therapeutically effective amount of the active pharmaceutical ingredient is administered to the subject for at least 4 hours. In some aspects, the therapeutically effective amount of the active pharmaceutical ingredient is administered to the subject for at least 6 hours. In some aspects, the therapeutically effective amount of the active pharmaceutical ingredient is administered to the subject for about 4 days. In some aspects, the therapeutically effective amount of the active pharmaceutical ingredient is administered to the subject for about 5 days. In some aspects, the therapeutically effective amount of the active pharmaceutical ingredient is administered to the subject for about 6 days. In some aspects, the therapeutically effective amount of the active pharmaceutical ingredient is administered to the subject for about 7 days.

The fibrous structures of the disclosure can comprise synthetic fibers, manmade fibers, and/or natural fibers, in any combination. Examples of synthetic fibers include, for example, polyamide fibers, acrylic fibers, elastane fibers, polyolefin fibers, polyester fibers and polylactic acid fibers. Examples of manmade fibers include, for example, modified cellulose fibers (e.g., rayon, lyocel), modified protein fibers (e.g., casein, soy, zein) and combinations thereof. Examples of natural fibers include, for example, protein fibers, cellulosic fibers (e.g., cotton, flax, hemp, jute), animal fibers (e.g., wool, mohair, cashmere), insect fibers (e.g., silk), and combinations thereof.

In some aspects, the fibrous structures comprise synthetic fibers. The structure may entirely comprise synthetic fibers, that is, 100% of the fibers are synthetic fibers. In other aspects, the fibrous structures comprise a blend of synthetic fibers and manmade fibers. In other aspects, the fibrous structures comprise a blend of synthetic fibers and natural fibers. In other aspects, the fibrous structures comprise a blend of synthetic fibers, manmade fibers, and natural fibers. In those aspects comprising a blend of synthetic fibers with other fibers, the fibrous structure may comprise about 5, 10, 15, 20, 25, 30, 35, 40, 45, 50, 55, 60, 65, 70, 75, 80, 85, 90, 91, 92, 93, 94, 95, 96, 97, 98, or about 99%, by weight, of synthetic fibers, with the remainder being manmade fibers, natural fibers, or a combination thereof.

In some aspects, the fibrous structures comprise manmade fibers. The structure may entirely comprise manmade fibers, that is, 100% of the fibers are manmade fibers. In other aspects, the fibrous structures comprise a blend of manmade and synthetic fibers. In other aspects, the fibrous structures comprise a blend of manmade fibers and natural fibers. In other aspects, the fibrous structures comprise a blend of manmade fibers, synthetic fibers, and natural fibers. In those aspects comprising a blend of manmade fibers with other fibers, the fibrous structure may comprise about 5, 10, 15, 20, 25, 30, 35, 40, 45, 50, 55, 60, 65, 70, 75, 80, 85, 90, 91, 92, 93, 94, 95, 96, 97, 98, or about 99%, by weight, of manmade fibers, with the remainder being synthetic fibers, natural fibers, or a combination thereof.

In some aspects, the fibrous structures comprise natural fibers. The structure may entirely comprise natural fibers, that is, 100% of the fibers are natural fibers. In other aspects, the fibrous structures comprise a blend of natural fibers and manmade fibers. In other aspects, the fibrous structures comprise a blend of natural fibers and synthetic fibers. In other aspects, the fibrous structures comprise a blend of natural fibers, synthetic fibers, and manmade fibers. In those aspects comprising a blend of natural fibers with other fibers, the fibrous structure may comprise about 5, 10, 15, 20, 25, 30, 35, 40, 45, 50, 55, 60, 65, 70, 75, 80, 85, 90, 91, 92, 93, 94, 95, 96, 97, 98, or about 99%, by weight, of natural fibers, with the remainder being synthetic fibers, manmade fibers, or a combination thereof.

The fibrous structures of the disclosure can be in any shape or form. For example, fibrous structures of the disclosure can be in the form of sheets or tubes. As used herein, the term "denier" refers to the linear mass density of a filament expressed as the mass in grams per 9000 meters of filament. The denier per filament (DPF) of the constituent fibers can range from 0.1 to 100 denier. The yarns may be made of staple fibers or continuous fibers with yarn denier ranging from 1 to 10,000 denier, plied or single, twisted or untwisted, textured or flat. The fabrics may be woven fabrics in plain weave, twill, sateen or jacquard interlacing. The fabrics may be knit fabrics either weft or warp knit, flat knit or circular knit, seamed or seamless. The fabrics may be nonwoven fabrics produced on needle punched, wet laid, air laid, thermobonded, calendared, spun-laced, spun-bonded, melt-blown or electrospun systems. The fabrics may be braided using any number of interlaced strands. In other aspects, the fibrous structures are in the form of a wearable garment, in particular a garment that can remain in contact with the skin on any place of the body or face. In certain aspects, the wearable garment fits tightly or snugly against the skin or body part of the wearer. Such garments include, for example, gloves, socks, shirts (including T-shirts), pants, caps, underpants, brassieres, and bands (e.g., armbands, legbands, headbands, wristbands, backbelts kneebands, anklebands, elbowbands, neckbands). Socks, t-shirts, gloves, and bands are particularly preferred garments. In some aspects, the garment is a non-occlusive, pharmaceutical garment, for example, in the forms of a sock, T-shirt, glove, or band.

The fibrous structures of the disclosure may optionally be scoured, bleached, or finished using conventional techniques. Alternatively, fibrous structures of the disclosure may be dyed or printed any color, using techniques known in the art.

Some aspects of the disclosure are directed to finished, non-occlusive, pharmaceutical fibrous structures that have been finished with a finishing composition comprising an active pharmaceutical ingredient, or a pharmaceutically acceptable salt thereof, and a solvent. The finishing composition may optionally also comprise a surfactant. While not wishing to be bound by any particular theory, it is believed that the addition of a surfactant may facilitate dispersion of the API (or salt thereof) in the finishing composition. The finishing composition may optionally also comprise a humectant. While not wishing to be bound by any particular theory, it is believed that the addition of a humectant may improve coating flexibility by holding on to water. The finishing composition may optionally also comprise a permeation enhancer. While not wishing to be bound by any particular theory, it is believed that the addition of a permeation enhancer may improve flow during deposition during the finishing treatment, improving uniformity (e.g., leveling) and/or increase permeation of the API through the subject's skin. In some aspects, the finishing composition may also comprise a surfactant, a humectant, a permeation enhancer, or a combination thereof.

In preferred aspects, the finished, non-occlusive, pharmaceutical fibrous structures of the disclosure that have been finished with finishing compositions, are hypoallergenic. In other aspects, these finished, non-occlusive, pharmaceutical fibrous structures are non-irritant. In other aspects, these finished, non-occlusive, pharmaceutical fibrous structures of the disclosure are substantially non-adhesive to a subject's skin. In some aspects, these non-adhesive structures are non-tacky at ambient temperature or above. In some aspects, these non-adhesive structures may be devoid of any adhesive material, i.e., the structures do not comprise any material that is tacky at ambient temperature or above. In other aspects, these non-adhesive structure may comprise a material that is tacky at ambient temperature and above, but the amount of that material is insufficient to confer tackiness to the structure at ambient temperature or above.

The fibrous structures of the finished, non-occlusive, pharmaceutical fibrous structures of the disclosure can comprise synthetic fibers, manmade fibers, and/or natural fibers as described herein. For example, in some of these aspects, the fibrous structures comprise synthetic fibers as described herein. In other aspects, the fibrous structures comprise manmade fibers. In other aspects, the fibrous structures comprise natural fibers as described herein. In other aspects, the fibrous structures comprise a blend of synthetic fibers and manmade fibers as described herein. In other aspects, the fibrous structures comprise a blend of synthetic fibers and natural fibers as described herein. In other aspects, the fibrous structures comprise a blend of manmade fibers and natural fibers as described herein. In other aspects, the fibrous structures comprise a blend of synthetic fibers, manmade fibers, and natural fibers as described herein.

The active pharmaceutical ingredients (APIs), or pharmaceutically acceptable salts thereof, can be present in the finishing compositions of the disclosure in an amount of from about 0.1% (w/w) to about 25% (w/w). For example, the API or API salt can be present in the finishing composition in an amount of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or about 25% (w/w). In some aspects, the API or API salt can be present in the finishing composition in an amount of from about 0.1% (w/w) to about 15% (w/w) or from about 0.1% (w/w) to about 10% (w/w). In some aspects, the API or API salt can be present in the finishing composition in an amount of from about 1% (w/w) to about 10% (w/w) or from about 10% (w/w) to about 25% (w/w). In some aspects, the API or API salt can be present in the finishing composition in an amount of from about 15% (w/w) to about 25% (w/w).

APIs useful in all aspects of the disclosure are those known in the art to be useful for transdermal or dermal administration to a subject. Those APIs that are particularly envisioned for use with the claimed methods and fibrous structures are those APIs that can be administered topically (transdermally or dermally) and that achieve a local-acting effect with low levels of systemic exposure. In other aspects, the APIs can be administered topically and achieve therapeutically effective systemic levels of exposure in the subject. In other aspects, the APIs can be administered topically and achieve therapeutically effective systemic levels of exposure in the subject, as well as therapeutically effective local levels of exposure in the subject. Preferred APIs are generally lipophilic. Alternatively, the API can be hydrophilic.

APIs useful in all aspects of the disclosure include antibiotics. Also within the scope of the disclosure are APIs useful for treating allergies, psoriasis, chronic venous insufficiency, and leg ulcers. Insecticides are also useful for the disclosure. Aesthetic and cosmetic APIs can be useful within the scope of the disclosure. Anti-inflammatory APIs can be useful within the scope of the disclosure. Angiogenesis or anti-angiogenesis APIs can be useful within the scope of the disclosure. Wound healing and anti-scarring APIs can be useful within the scope of the disclosure. APIs useful in treating the common cold are also within the scope of the disclosure. APIs useful for treating gout are also within the scope of the disclosure.

For example, suitable APIs useful in all aspects of the disclosure include, for example, sodium channel blockers, analgesics, non-steroidal anti-inflammatory drugs, and opioids (e.g., morphine). In some aspects, the API is lidocaine, prilocaine, bupivacaine, mepivacaine, ropivacaine, articaine, tetracaine, capsaicin, diclofenac, menthol, methyl salicylate, salicylic acid, and combinations thereof. In other aspects, the API is Scopolamine, Nitroglycerin, Clonidine, Estradiol, Estradiol/norethidrone, Ethinyl estradiol/norelgestromin, Estradiol/levonorgestrel Fentanyl, Nicotine, Testosterone, Lidocaine, Oxybutynin, Lidocaine/tetracaine, Prilocaine, Methylphenidate, Selegiline, Rotigotine, Rivastigmine. In some aspects, the API is lidocaine. In some aspects, the API is prilocaine. In some aspects, the API is bupivacaine. In some aspects, the API is mepivacaine, ropivacaine. In some aspects, the API is articaine. In some aspects, the API is tetracaine. In some aspects, the API is capsaicin. In some aspects, the API is diclofenac. In some aspects, the API is menthol. In some aspects, the API is methyl salicylate. In some aspects, the API is salicylic acid. In some aspects, the API is Scopolamine. In some aspects, the API is Nitroglycerin. In some aspects, the API is Clonidine. In some aspects, the API is Estradiol. In some aspects, the API is Estradiol/norethidrone. In some aspects, the API is Ethinyl estradiol/norelgestromin. In some aspects, the API is Estradiol/levonorgestrel Fentanyl. In some aspects, the API is Nicotine. In some aspects, the API is Testosterone. In some aspects, the API is Oxybutynin. In some aspects, the API is Lidocaine/tetracaine. In some aspects, the API is Methylphenidate. In some aspects, the API is Selegiline. In some aspects, the API is Rotigotine. In some aspects, the API is Rivastigmine. In some aspects, the API is Betamethasone. In some aspects, the API is Buprenorphine. In some aspects, the API is Triclocarban. In some aspects, the API is Acyclovir. In some aspects, the API is Adapalene. In some aspects, the API is Allantoin. In some aspects, the API is Benzocaine. In some aspects, the API is Bexarotene. In some aspects, the API is Brimonidine. In some aspects, the API is Calcipotriene. In some aspects, the API is Calcitriol. In some aspects, the API is Ciclopirox. In some aspects, the API is Clindamycin. In some aspects, the API is lobetasol. In some aspects, the API is Dapsone. In some aspects, the API is Diphenhydramine. In some aspects, the API is Doxepin. In some aspects, the API is Econazole. In some aspects, the API is Fluocinolone. In some aspects, the API is Fluticasone. In some aspects, the API is Halobetasol. In some aspects, the API is Hydrocortisone. In some aspects, the API is Imiquimod. In some aspects, the API is Ingenol. In some aspects, the API is Ivermectin. In some aspects, the API is Ketoconazole. In some aspects, the API is Loteprednol. In some aspects, the API is Luliconazole. In some aspects, the API is Mafenide. In some aspects, the API is Ibuprofen. In some aspects, the API is Metronidazole. In some aspects, the API is Miconazole. In some aspects, the API is Minoxidil. In some aspects, the API is Mometasone. In some aspects, the API is Mupirocin. In some aspects, the API is Neomycin. In some aspects, the API is Nystatin. In some aspects, the API is Penciclovir. In some aspects, the API is Phenylephedrine. In some aspects, the API is Pimecrolimus. In some aspects, the API is Pramoxine. In some aspects, the API is Selenium. In some aspects, the API is Sulconazole. In some aspects, the API is Sulfacetamide. In some aspects, the API is Tacrolimus. In some aspects, the API is Tavaborole. In some aspects, the API is Tetracycline. In some aspects, the API is Tioconazole. In some aspects, the API is Tretinoin. In some aspects, the API is Triamcinolone. In some aspects, the API is Triclosan. In some aspects, the API is Terbinafine. In some aspects, the API is Clotrimazole. In some aspects, the API is Detomidine. Is some aspects, the API is Medetomidine. In some aspects, the API is Dexmedetomidine.

The following classes of APIs are also envisioned:
Metals and metal salts—Antimicrobial
Quaternary ammonium compounds—Antimicrobial
Triclosan—Antimicrobial agent
Chitosan—Antibacterial
N-halamines—Antimicrobial polymers
Natural dyestuffs—Antimicrobial
Peroxyacids—Antimicrobial
Clotrimazole—Antifungal
Terbinafine—Antifungal
Menthol—Allergy
Propolis extract—Allergy
Tacrolimus, calcipotriene, tofacitinib—Psoriasis
Hydrocortisone acetate—Psoriasis
Ciprofloxacin—Antibiotic (wound healing)
Troxerutin—A plant flavonoid, antioxidant
Dithranol—Psoriasis
Curcumin—Inflammation, skin healing
Citric acid—Antimicrobial, atopic dermatitis
*Citrus grandis* osbeck extract—Antimicrobial, atopic dermatitis
Caffeine—Anti-cellulite
Lidocaine—Pain
Ethereal oils—common cold
Cyclodextrins, aza-crown ethers or fullerenes—common cold
Caffeine and Gallic acid—anti-cellulite and antioxidant
Ibuprofen—anti-inflammatory compound
Antibiotics—Chronic wounds/bacterial infection
Antibiotics—Atopic dermatitis
Vascular endothelial growth factor (VEGF)—angiogenesis
Ascorbic acid—Chronic venous leg ulcers
Deferoxamine—diabetic foot ulcers
*Ficus racemosa* (alkaloid & flavonoid fractions)—wound healing
Colchicine—gout Combinations of APIs are also envisioned. For example, fibrous structures finished with lidocaine and prilocaine are within the scope of the disclosure. Combinations such as lidocaine, bupivacaine, mepivacaine, prilocaine, ropivacaine, and articaine are also envisioned.

The solvent used in the finishing compositions of the disclosure can be an aqueous solvent or an organic solvent or a combination of water and an organic solvent. In some aspects, the finishing composition of the disclosure is an aqueous solution comprising an aqueous solvent combined with the other components. The aqueous solvent can be water. In other aspects, the aqueous solvent can comprise water and an organic, water-miscible solvent. In some aspects, the aqueous solvent comprising at least about 10% (v/v) water. In other aspects, the aqueous solvent comprises at least about 15, 20, 25, 30, 35, 40, 45, 50, 55, 60, 65, 70, 75, 80, 85, 90, 95, or about 100% (v/v) of water. In other aspects, the solvent comprises less than 10% (v/v) water, for example, 9, 8, 7, 6, 5, 4, 3, 2, or 1% (v/v) or less of water. Alternatively, the finishing composition of the disclosure is an organic solvent (e.g., chloroform, diethyl ether, tetrahydrofuran, toluene, hexanes, methanol, ethanol, propanol, and the like, and mixtures thereof), or combination of organic solvents, combined with other components. In some aspects, the organic solvent can be methanol, ethanol or propanol.

In some aspects, the finishing compositions of the disclosure are prepared by combining the active pharmaceutical ingredient, or a pharmaceutically acceptable salt thereof, in the solvent to form the finishing composition. The solvent can be water, an organic solvent (e.g., chloroform, diethyl ether, tetrahydrofuran, toluene, hexanes, methanol, ethanol, propanol, and the like, and mixtures thereof), or a mixture of water and an organic solvent, as described herein.

In other aspects, finishing compositions of the disclosure, in addition to the API (or salt thereof) and the solvent, may further comprise a surfactant. In some of these aspects, the surfactant is combined with the active pharmaceutical ingredient, or a pharmaceutically acceptable salt thereof, in the solvent to form a finishing composition. In some aspects, finishing compositions are prepared by combining a surfactant and the active pharmaceutical ingredient, or a pharmaceutically acceptable salt thereof, in an aqueous solvent to form a finishing composition. In some aspects, finishing compositions are prepared by combining a surfactant and the active pharmaceutical ingredient, or a pharmaceutically acceptable salt thereof, in water to form a finishing composition. In some aspects, finishing compositions are prepared by combining a surfactant and the active pharmaceutical ingredient, or a pharmaceutically acceptable salt thereof, in an organic solvent (e.g., chloroform, diethyl ether, tetrahydrofuran, toluene, hexanes, methanol, ethanol, propanol, and the like, and mixtures thereof) to form a finishing composition. In some aspects, finishing compositions are prepared by combining a surfactant and the active pharmaceutical ingredient, or a pharmaceutically acceptable salt thereof, in solvent comprising water and an organic solvent (e.g., chloroform, diethyl ether, tetrahydrofuran, toluene, hexanes, methanol, ethanol, propanol, and the like, and mixtures thereof) to form a finishing composition.

The surfactant can be present in the finishing composition in an amount of from about 0.1% (w/w) to about 5% (w/w). For example, the surfactant can be present in the finishing composition in an amount of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5% (w/w). In some aspects, the surfactant can be present in the finishing composition in an amount of from about 0.1% (w/w) to about 3% (w/w) or from about 1% (w/w) to about 3% (w/w). In some aspects, the surfactant can be present in the finishing composition in an amount of from about 0.5% (w/w) to about 3.5% (w/w) or from about 1.5% (w/w) to about 2.5% (w/w). In some aspects, the surfactant can be present in the finishing composition in an amount of from about 1.5% (w/w) to about 4% (w/w).

In other aspects, the surfactant can be present in the finishing composition in an amount of up to 30% (w/w). For example, the surfactant can be present in the finishing composition in an amount of about 6, 7, 8, 9, 10, 11, 12, 13, 14, 15, 16, 17, 18, 19, 20, 21, 22, 23, 24, 25, 26, 27, 28, 29, or about 30% (w/w). In some aspects, the surfactant can be present in the finishing composition in an amount of from about 6% (w/w) to about 30% (w/w) or from about 10% (w/w) to about 30% (w/w). In some aspects, the surfactant can be present in the finishing composition in an amount of from about 15% (w/w) to about 25% (w/w) or from about 15% (w/w) to about 20% (w/w). In some aspects, the surfactant can be present in the finishing composition in an amount of from about 20% (w/w) to about 25% (w/w).

Surfactants suitable for use in the disclosure are known in the art and include nonionic surfactants. Preferred nonionic surfactants include, for example, fatty acid esters of glycerol and fatty acid esters of sorbitol, ethoxylated amines, fatty acid amide (e.g., polyethoxylated tallow amine, cocamide monoethanolamine, cocamide diethanolamine), terminally blocked ethoxylates (e.g., poloxamers), as well as combinations thereof. In preferred embodiments, the surfactant is a fatty acid ester of sorbitol. Preferred fatty acid esters of sorbitol are polysorbates, for example, polysorbate 20, polysorbate 40, polysorbate 60, and polysorbate 80. Polysorbate 80 is preferred.

The finishing composition can optionally include a humectant. In some embodiments, the finishing composition comprises a humectant and the active pharmaceutical ingredient, or a pharmaceutically acceptable salt thereof, in a solvent (aqueous or organic solvent). In some embodiments, the finishing composition comprises a surfactant, a humectant, and the active pharmaceutical ingredient, or a pharmaceutically acceptable salt thereof, in a solvent (aqueous or organic solvent). In those aspects wherein the humectant is a liquid at ambient temperature, the finishing composition may be prepared in the absence of a solvent. That is, in these embodiments, the finishing compositions comprises a humectant and the active pharmaceutical ingredient, or a pharmaceutically acceptable salt thereof. In other of these aspects, the finishing composition comprises a surfactant, a humectant, and the active pharmaceutical ingredient, or a pharmaceutically acceptable salt thereof.

In those embodiments employing a humectant, the humectant can be present in the finishing composition in an amount of from about 5% (w/w) to about 25% (w/w). For example, the humectant can be present in the finishing composition in an amount of about 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or about 25% (w/w). In some aspects, the humectant can be present in the finishing composition in an amount of from about 5% (w/w) to about 10% (w/w) or from about 10% (w/w) to about 15% (w/w). In some aspects, the humectant can be present in the finishing composition in an amount of from about 15% (w/w) to about 25% (w/w). In some aspects, the humectant can be present in the finishing composition in an amount of from about 20% (w/w) to about 25% (w/w). In some aspects, the humectant can be present in the finishing composition in an amount of from about 8% (w/w) to about 12% (w/w) or from about 9% (w/w) to about 11% (w/w). In some aspects, the humectant can be present in the finishing composition in an amount of from about 12% (w/w) to about 15% (w/w).

Humectants suitable for use in the disclosure are known in the art and include, for example, polyalkene glycols, polymeric polyols, sugar alcohols, and combinations thereof. Suitable polyalkene glycols include, for example, polyethylene glycols, such as, for example, polyethylene glycols having an average molecular weight of about 200 daltons to about 800 daltons, for example, 200, 400, 600, or about 800 daltons. Polyethylene glycol 400 is a preferred humectant. Suitable polymeric polyols include, for example, polymers of monosaccharides, such as, for example, polydextrose. Suitable sugar alcohols include, for example, arabitol, erythritol, fucitol, glycerol, galactitol, HSH, iditol, inositol, isomalt, lactitol, maltitol, mannitol, ribitol, sorbitol, threitol, volemitol, and xylitol.

The finishing compositions of the disclosure can optionally include a permeation enhancer. In those embodiments, the finishing composition comprises a surfactant, a permeation enhancer, and the active pharmaceutical ingredient, or a pharmaceutically acceptable salt thereof, in a solvent (aqueous or organic solvent). In other aspects, the finishing composition comprises a permeation enhancer and the active pharmaceutical ingredient, or a pharmaceutically acceptable salt thereof, in a solvent (aqueous or organic solvent). The finishing composition can optionally include both a humectant and a permeation enhancer. In those embodiments, the finishing composition comprises a surfactant, a humectant, a permeation enhancer, and the active pharmaceutical ingredient, or a pharmaceutically acceptable salt thereof, in a solvent (aqueous or organic solvent). In those aspects wherein the permeation enhancer is a liquid at ambient temperature, the finishing composition may be prepared in the absence of a solvent. That is, in these embodiments, the finishing compositions comprises a surfactant, a permeation enhancer, and the active pharmaceutical ingredient, or a pharmaceutically acceptable salt thereof. In other of these aspects, the finishing composition comprises a surfactant, a humectant, a permeation enhancer, and the active pharmaceutical ingredient, or a pharmaceutically acceptable salt thereof. In other of these aspects, the finishing composition comprises a permeation enhancer and the active pharmaceutical ingredient, or a pharmaceutically acceptable salt thereof.

In those embodiments employing a permeation enhancer, the permeation enhancer can be present in the finishing composition in an amount of from about 5% (w/w) to about 25% (w/w). For example, the permeation enhancer can be present in the finishing composition in an amount of about 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or about 25% (w/w). In some aspects, the permeation enhancer can be present in the finishing composition in an amount of from about 5% (w/w) to about 10% (w/w) or from about 10% (w/w) to about 15% (w/w). In some aspects, the permeation enhancer can be present in the finishing composition in an amount of from about 15% (w/w) to about 25% (w/w). In some aspects, the permeation enhancer can be present in the finishing composition in an amount of from about 20% (w/w) to about 25% (w/w). In some aspects, the permeation enhancer can be present in the finishing composition in an amount of from about 8% (w/w) to about 12% (w/w) or from about 9% (w/w) to about 11% (w/w). In some aspects, the permeation enhancer can be present in the finishing composition in an amount of from about 12% (w/w) to about 15% (w/w).

Permeation enhancers suitable for use in the disclosure are known in the art and include, for example, monomeric glycols, monomeric polyols (e.g., glycerol), monomeric alcohols, pyrrolidones, medium chain glycerides, laurate salts, bile salts and derivatives, fatty acids, fatty acid derivatives, chelating agents, sulfoxides, urea and urea derivatives, terpenes, terpenoids, phospholipids, dimethyl acetamide, dimethylformamide, diethylene glycol monoethyl ether, dimethyl isosorbide, and combinations thereof. Suitable monomeric glycols include, for example, propylene glycol. Suitable monomeric alcohols include, for example, ethanol, 2-propanol, and decanol. Suitable pyrrolidones include, for example, 2-pyrrolidone and N-methyl pyrrolidone. Bile salts and derivatives include, for example, sodium glycolate and sodium deoxycholate. Suitable sulfoxides include, for example, dimethyl sulfoxide. Fatty acids are known in the art and include, for example, oleic acid and caprylic acid. Chelating agents include, for example, ethylenediaminetetraacetic acid (EDTA) and citric acid.

The finished, non-occlusive, pharmaceutical fibrous structures of the disclosure are such that the active pharmaceutical ingredient (or pharmaceutically acceptable salt thereof) is distributed substantially homogenously throughout the fibrous structure. In these aspects, the finish is a "level" finish. That is, the API (or salt thereof) is distributed throughout the fibrous structure such that the concentration of API (or salt thereof) differs by 25% or less, across the whole of the structure. For example, the concentration of API (or salt thereof) differs by 1, 2, 3, 4, 5, 6, 7, 8, 9, 10, 11, 12, 13, 14, 15, 16, 17, 18, 19, 20, 21, 22, 23, 24, or 25% or less across the whole of the fibrous structure.

In some aspects, the finished, non-occlusive, pharmaceutical fibrous structures of the disclosure are such that the quantitative distribution of API (or salt thereof), the thickness distribution of the API (or salt thereof), the crystallinity of the API (or salt thereof), the adherence of the API (or salt thereof), or a combination thereof, is level throughout the structure. In some aspects, the quantitative distribution of API (or salt thereof) differs by 25% or less, across the whole of the structure. For example, the quantitative distribution of API (or salt thereof) differs by 1, 2, 3, 4, 5, 6, 7, 8, 9, 10, 11, 12, 13, 14, 15, 16, 17, 18, 19, 20, 21, 22, 23, 24, or 25% or less across the whole of the structure. In some aspects, the thickness distribution of API (or salt thereof) differs by 25% or less, across the whole of the structure. For example, the thickness distribution of API (or salt thereof) differs by 1, 2, 3, 4, 5, 6, 7, 8, 9, 10, 11, 12, 13, 14, 15, 16, 17, 18, 19, 20, 21, 22, 23, 24, or 25% or less across the whole of the structure. In some aspects, the crystallinity of the API (or salt thereof) differs by 25% or less, across the whole of the structure. For example, the crystallinity of the API (or salt thereof) differs by 1, 2, 3, 4, 5, 6, 7, 8, 9, 10, 11, 12, 13, 14, 15, 16, 17, 18, 19, 20, 21, 22, 23, 24, or 25% or less across the whole of the structure. In some aspects, the adherence of the API (or salt thereof) differs by 25% or less, across the whole of the structure. For example, the adherence of the API (or salt thereof) differs by 1, 2, 3, 4, 5, 6, 7, 8, 9, 10, 11, 12, 13, 14, 15, 16, 17, 18, 19, 20, 21, 22, 23, 24, or 25% or less across the whole of the structure.

Non-occlusive, pharmaceutical fibrous structures according to the disclosure (including those produced according to the described methods) contain sufficient quantities of API so as to allow for administration of the API. The amount of API on the finished fibrous structure can be identified by analysis of the mass balance of the finishing composition and/or by the fibrous structure's percentage Add on. The percentage Add on of the finished fibrous structure can be calculated as 100*(weight of the finished fibrous structure–weight of the fibrous structure prior to finishing)/weight of the fibrous structure prior to finishing. In some aspects, the percentage Add on of the finished fibrous structure can be from 20% to about 300%. For example, the percentage Add on of the finished fibrous structure can be 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300%, as compared to the dry weight of the fibrous structure absent the finishing composition treatment. In some aspects, the percentage Add on of the finished fibrous structure is increased at least about 20%. In other aspects, the percentage Add on of the finished fibrous structure is increased up to about 300%, as compared to the dry weight of the fibrous structure absent the finishing composition treatment.

In some aspects, the Add on weight is present on the finished fibrous structure of the disclosure in an amount of about 1 $g/m^2$ to about 1200 $g/m^2$. In some aspects, the Add on weight is present on the finished fibrous structure of the disclosure in an amount of about 1 $g/m^2$ to about 50 $g/m^2$. In some aspects, the Add on weight is present on the finished fibrous structure of the disclosure in an amount of about 50 $g/m^2$ to about 100 $g/m^2$. In some aspects, the Add on weight is present on the finished fibrous structure of the disclosure in an amount of about 100 $g/m^2$ to about 150 $g/m^2$. In some aspects, the Add on weight is present on the finished fibrous structure of the disclosure in an amount of about 150 $g/m^2$ to about 200 $g/m^2$. In some aspects, the Add on weight is present on the finished fibrous structure of the disclosure in an amount of about 200 $g/m^2$ to about 250 $g/m^2$. In some aspects, the Add on weight is present on the finished fibrous structure of the disclosure in an amount of about 250 $g/m^2$ to about 300 $g/m^2$. In some aspects, the Add on weight is present on the finished fibrous structure of the disclosure in an amount of about 300 $g/m^2$ to about 350 $g/m^2$. In some aspects, the Add on weight is present on the finished fibrous structure of the disclosure in an amount of about 350 $g/m^2$ to about 400 $g/m^2$. In some aspects, the Add on weight is present on the finished fibrous structure of the disclosure in an amount of about 400 $g/m^2$ to about 450 $g/m^2$. In some aspects, the Add on weight is present on the finished fibrous structure of the disclosure in an amount of about 450 $g/m^2$ to about 500 $g/m^2$. In some aspects, the Add on weight is present on the finished fibrous structure of the disclosure in an amount of about 500 $g/m^2$ to about 600 $g/m^2$. In some aspects, the Add on weight is present on the finished fibrous structure of the disclosure in an amount of about 600 g/m² to about 700 g/m². In some aspects, the Add on weight is present on the finished fibrous structure of the disclosure in an amount of about 700 g/m² to about 800 g/m². In some aspects, the Add on weight is present on the finished fibrous structure of the disclosure in an amount of about 800 g/m² to about 900 g/m². In some aspects, the Add on weight is present on the finished fibrous structure of the disclosure in an amount of about 900 g/m² to about 1000 g/m². In some aspects, the Add on weight is present on the finished fibrous structure of the disclosure in an amount of about 1000 g/m² to about 1100 g/m². In some aspects, the Add on weight is present on the finished fibrous structure of the disclosure in an amount of about 1100 g/m² to about 1200 g/m². In some aspects, the Add on weight is present on the finished fibrous structure of the disclosure in an amount of about 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050, 1100, 1150, or about 1200 g/m².

The API finished fibrous structures of the disclosure are found to maintain both the functional and aesthetic properties of the fibrous structure as found prior to its finishing. As such, the API finished fibrous structures of the disclosure are found to have minor changes in the tensile strength when compared to the fibrous structure as found prior to its finishing, which do not affect their softness, strength, breathability, vapor transport, flexibility and appearance when compared to their structures prior to finishing. Similarly, the API finished fibrous structures of the disclosure are found to have minimal friability of the finishing composition from the fibrous structure.

In some aspects, the finished, non-occlusive, pharmaceutical fibrous structures of the disclosure have a tensile strength of about 10 kgf to about 50 kgf peak load at 25° C. and 51% relative humidity, when tested according to ASTM D5034-09. In some aspects, the finished, non-occlusive, pharmaceutical fibrous structures of the disclosure have a tensile strength of about 10 kgf to about 15 kgf peak load at 25° C. and 51% relative humidity. In some aspects, the finished, non-occlusive, pharmaceutical fibrous structures of the disclosure have a tensile strength of about 15 kgf to about 20 kgf peak load at 25° C. and 51% relative humidity. In some aspects, the finished, non-occlusive, pharmaceutical fibrous structures of the disclosure have a tensile strength of about 20 kgf to about 25 kgf peak load at 25° C. and 51% relative humidity. In some aspects, the finished, non-occlusive, pharmaceutical fibrous structures of the disclosure have a tensile strength of about 25 kgf to about 30 kgf peak load at 25° C. and 51% relative humidity. In some aspects, the finished, non-occlusive, pharmaceutical fibrous structures of the disclosure have a tensile strength of about 30 kgf to about 35 kgf peak load at 25° C. and 51% relative humidity. In some aspects, the finished, non-occlusive, pharmaceutical fibrous structures of the disclosure have a tensile strength of about 35 kgf to about 40 kgf peak load at 25° C. and 51% relative humidity. In some aspects, the finished, non-occlusive, pharmaceutical fibrous structures of the disclosure have a tensile strength of about 40 kgf to about 45 kgf peak load at 25° C. and 51% relative humidity. In some aspects, the finished, non-occlusive, pharmaceutical fibrous structures of the disclosure have a tensile strength of about 45 kgf to about 50 kgf peak load at 25° C. and 51% relative humidity. In some aspects, the finished, non-occlusive, pharmaceutical fibrous structures of the disclosure have a tensile strength of about 10, 15, 20, 25, 30, 35, 40, 45, or about 50 kgf peak load at 25° C. and 51% relative humidity.

In some aspects, the finished, non-occlusive, pharmaceutical fibrous structures of the disclosure have a tensile strength that is equivalent to, or up to 150% greater than, the tensile strength of the fibrous structure absent the treatment with the finishing composition, when tested according to ASTM D5034-09. In some aspects, the finished, non-occlusive, pharmaceutical fibrous structures of the disclosure have a tensile strength that is equivalent to the tensile strength of the fibrous structure absent the treatment with the finishing composition. In some aspects, the finished, non-occlusive, pharmaceutical fibrous structures of the disclosure have a tensile strength that is up to 150% greater than the tensile strength of the fibrous structure absent the treatment with the finishing composition. In some aspects, the finished, non-occlusive, pharmaceutical fibrous structures of the disclosure have a tensile strength that is 5% to 20% greater than the tensile strength of the fibrous structure absent the treatment with the finishing composition. In some aspects, the finished, non-occlusive, pharmaceutical fibrous structures of the disclosure have a tensile strength that is 20% to 50% greater than the tensile strength of the fibrous structure absent the treatment with the finishing composition. In some aspects, the finished, non-occlusive, pharmaceutical fibrous structures of the disclosure have a tensile strength that is 50% to 75% greater than the tensile strength of the fibrous structure absent the treatment with the finishing composition. In some aspects, the finished, non-occlusive, pharmaceutical fibrous structures of the disclosure have a tensile strength that is 75% to 100% greater than the tensile strength of the fibrous structure absent the treatment with the finishing composition. In some aspects, the finished, non-occlusive, pharmaceutical fibrous structures of the disclosure have a tensile strength that is 100% to 125% greater than the tensile strength of the fibrous structure absent the treatment with the finishing composition. In some aspects, the finished, non-occlusive, pharmaceutical fibrous structures of the disclosure have a tensile strength that is 125% to 150% greater than the tensile strength of the fibrous structure absent the treatment with the finishing composition. In some aspects, the finished, non-occlusive, pharmaceutical fibrous structures of the disclosure have a tensile strength that is 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, or about 150% greater than the tensile strength of the fibrous structure absent the treatment with the finishing composition.

In some aspects, the finished, non-occlusive, pharmaceutical fibrous structures of the disclosure have a stiffness of about 10 mm to about 50 mm, when tested according to ASTM method D1388-18. In some aspects, the finished, non-occlusive, pharmaceutical fibrous structures of the disclosure have a stiffness of about 10 mm to about 20 mm. In some aspects, the finished, non-occlusive, pharmaceutical fibrous structures of the disclosure have a stiffness of about 20 mm to about 30 mm. In some aspects, the finished, non-occlusive, pharmaceutical fibrous structures of the disclosure have a stiffness of about 30 mm to about 40 mm. In some aspects, the finished, non-occlusive, pharmaceutical fibrous structures of the disclosure have a stiffness of about 40 mm to about 50 mm. In some aspects, the finished, non-occlusive, pharmaceutical fibrous structures of the disclosure have a stiffness of about 10, 15, 20, 25, 30, 35, 40, 45, or about 50 mm.

In some aspects, the finished, non-occlusive, pharmaceutical fibrous structures of the disclosure have a stiffness that is equivalent to, or up to 300% greater than, the stiffness of the fibrous structure absent treatment with the finishing composition, when tested according to ASTM method D1388-18. In some aspects, the finished, non-occlusive, pharmaceutical fibrous structures of the disclosure have a stiffness that is equivalent to the stiffness of the fibrous structure absent treatment with the finishing composition. In some aspects, the finished, non-occlusive, pharmaceutical fibrous structures of the disclosure have a stiffness that is up to 300% greater than the stiffness of the fibrous structure absent treatment with the finishing composition. In some aspects, the finished, non-occlusive, pharmaceutical fibrous structures of the disclosure have a stiffness that is 10% to 50% greater than the stiffness of the fibrous structure absent treatment with the finishing composition. In some aspects, the finished, non-occlusive, pharmaceutical fibrous structures of the disclosure have a stiffness that is 50% to 100% greater than the stiffness of the fibrous structure absent treatment with the finishing composition. In some aspects, the finished, non-occlusive, pharmaceutical fibrous structures of the disclosure have a stiffness that is 100% to 150% greater than the stiffness of the fibrous structure absent treatment with the finishing composition. In some aspects, the finished, non-occlusive, pharmaceutical fibrous structures of the disclosure have a stiffness that is 150% to 200% greater than the stiffness of the fibrous structure absent treatment with the finishing composition. In some aspects, the finished, non-occlusive, pharmaceutical fibrous structures of the disclosure have a stiffness that is 200% to 250% greater than the stiffness of the fibrous structure absent treatment with the finishing composition. In some aspects, the finished, non-occlusive, pharmaceutical fibrous structures of the disclosure have a stiffness that is 250% to 300% greater than the stiffness of the fibrous structure absent treatment with the finishing composition. In some aspects, the finished, non-occlusive, pharmaceutical fibrous structures of the disclosure have a stiffness that is 1, 2, 3, 4, 5, 6, 7, 8, 9, 10, 15, 20, 25, 30, 35, 40, 45, 50, 55, 60, 65, 70, 75, 80, 85 90, 95, 100, 125, 150, 175, 200, 225, 250, 275, or about 300% greater than the stiffness of the fibrous structure absent treatment with the finishing composition.

In some aspects, the finished, non-occlusive, pharmaceutical fibrous structures of the disclosure have an air permeation rate of about 200 mm/second to about 400 mm/second, when tested according to ASTM D737-09. These air permeation rates are particularly preferred for fibrous structures comprising nylon. In some aspects, the finished, non-occlusive, pharmaceutical fibrous structures of the disclosure have an air permeation rate of about 200 mm/second to about 250 mm/second. In some aspects, the finished, non-occlusive, pharmaceutical fibrous structures of the disclosure have an air permeation rate of about 250 mm/second to about 300 mm/second. In some aspects, the finished, non-occlusive, pharmaceutical fibrous structures of the disclosure have an air permeation rate of about 300 mm/second to about 350 mm/second. In some aspects, the finished, non-occlusive, pharmaceutical fibrous structures of the disclosure have an air permeation rate of about 350 mm/second to about 400 mm/second. In some aspects, the finished, non-occlusive, pharmaceutical fibrous structures of the disclosure have an air permeation rate of about 200, 225, 250, 275, 300, 325, 350, 375, or about 400 mm/second.

In some aspects, the finished, non-occlusive, pharmaceutical fibrous structures of the disclosure have an air permeation rate of about 2100 mm/second to about 2600 mm/second, when tested according to ASTM D737-09. These air permeation rates are particularly preferred for fibrous structures comprising cotton. In some aspects, the finished, non-occlusive, pharmaceutical fibrous structures of the disclosure have an air permeation rate of about 2100 mm/second to about 2200 mm/second. In some aspects, the finished, non-occlusive, pharmaceutical fibrous structures of the disclosure have an air permeation rate of about 2200 mm/second to about 2300 mm/second. In some aspects, the finished, non-occlusive, pharmaceutical fibrous structures of the disclosure have an air permeation rate of about 2300 mm/second to about 2400 mm/second. In some aspects, the finished, non-occlusive, pharmaceutical fibrous structures of the disclosure have an air permeation rate of about 2400 mm/second to about 2500 mm/second. In some aspects, the finished, non-occlusive, pharmaceutical fibrous structures of the disclosure have an air permeation rate of about 2500 mm/second to about 2600 mm/second. In some aspects, the finished, non-occlusive, pharmaceutical fibrous structures of the disclosure have an air permeation rate of about 2100, 2125, 2150, 2175, 2200, 2225, 2250, 2275, 2300, 2325, 2350, 2375, 2400, 2425, 2450, 2475, 2500, 2525, 2550, 2575, or about 2600 mm/second.

In some aspects, the finished, non-occlusive, pharmaceutical fibrous structures of the disclosure have an air permeation rate that is equivalent to, or +/−50% of, the air permeation rate of the fibrous structure absent treatment with the finishing composition, when tested according to ASTM D737-09. In some aspects, the finished, non-occlusive, pharmaceutical fibrous structures of the disclosure have an air permeation rate that is equivalent to the air permeation rate of the fibrous structure absent treatment with the finishing composition. In some aspects, the finished, non-occlusive, pharmaceutical fibrous structures of the disclosure have an air permeation rate that is less than 50% of (−50% of), the air permeation rate of the fibrous structure absent treatment with the finishing composition. In some aspects, the finished, non-occlusive, pharmaceutical fibrous structures of the disclosure have an air permeation rate that is greater than 50% of (50% of), the air permeation rate of the fibrous structure absent treatment with the finishing composition. In some aspects, the finished, non-occlusive, pharmaceutical fibrous structures of the disclosure have an air permeation rate that is 50% of (50% of), the air permeation rate of the fibrous structure absent treatment with the finishing composition. In some aspects, the finished, non-occlusive, pharmaceutical fibrous structures of the disclosure have an air permeation rate that is −50, −45, −40, −35, −30, −25, −20, −15, −10, −5, 0, 5, 10, 15, 20, 25, 30, 35, 40, 45 or about 50% of the air permeation rate of the fibrous structure absent treatment with the finishing composition.

The finishing compositions of the disclosure can be in the form of a solution, a suspension, an emulsion, or a dispersion. In some aspects, the finishing composition is a solution. In other aspects, the finishing composition is a suspension. In other aspects, the finishing composition is an emulsion. In other aspects, the finishing composition is a dispersion.

According to the disclosure, the non-occlusive, pharmaceutical fibrous structures finished with a finishing composition of the disclosure can be used to administer an active pharmaceutical ingredient to a subject. In these methods, the non-occlusive, pharmaceutical fibrous structure finished with a finishing composition of the disclosure is topically applied to the intact skin of the subject. According to the disclosure, the non-occlusive, pharmaceutical fibrous structure finished with a finishing composition of the disclosure is topically applied to the intact skin of the subject for a time sufficient to locally or systemically, or both, administer a therapeutically effective amount of the active pharmaceutical ingredient to the subject. In some aspects, the non-occlusive, pharmaceutical fibrous structure finished with a finishing composition of the disclosure is topically applied to the intact skin of the subject for a time sufficient to locally administer a therapeutically effective amount of the active pharmaceutical ingredient to the subject. In some aspects, the non-occlusive, pharmaceutical fibrous structure finished with a finishing composition of the disclosure is topically applied to the intact skin of the subject for a time sufficient to systemically administer a therapeutically effective amount of the active pharmaceutical ingredient to the subject. In some aspects, the non-occlusive, pharmaceutical fibrous structure finished with a finishing composition of the disclosure is topically applied to the intact skin of the subject for a time sufficient to locally and systemically administer a therapeutically effective amount of the active pharmaceutical ingredient to the subject.

In some aspects, the non-occlusive, pharmaceutical fibrous structure finished with a finishing composition of the disclosure is topically applied to the subject's intact skin for a time period of about 1 hour to about 72 hours. In some aspects, the non-occlusive, pharmaceutical fibrous structure finished with a finishing composition of the disclosure is topically applied to the subject's intact skin for a time period of about 8 hours to about 72 hours. In some aspects, the non-occlusive, pharmaceutical fibrous structure finished with a finishing composition of the disclosure is topically applied to the subject's intact skin for a time period of about 24 hours to about 72 hours. In some aspects, the non-occlusive, pharmaceutical fibrous structure finished with a finishing composition of the disclosure is topically applied to the subject's intact skin for a time period of about 48 hours to about 72 hours. In some aspects, the non-occlusive, pharmaceutical fibrous structure finished with a finishing composition of the disclosure is topically applied to the subject's intact skin for a time period of about 12 hours. In some aspects, the non-occlusive, pharmaceutical fibrous structure finished with a finishing composition of the disclosure is topically applied to the subject's intact skin for a time period of about 1 day. In some aspects, the non-occlusive, pharmaceutical fibrous structure finished with a finishing composition of the disclosure is topically applied to the subject's intact skin for a time period of about 2 days. In some aspects, the non-occlusive, pharmaceutical fibrous structure finished with a finishing composition of the disclosure is topically applied to the subject's intact skin for a time period of about 3 days. In some aspects, the non-occlusive, pharmaceutical fibrous structure finished with a finishing composition of the disclosure is topically applied to the subject's intact skin for a time period of about 4 days. In some aspects, the non-occlusive, pharmaceutical fibrous structure finished with a finishing composition of the disclosure is topically applied to the subject's intact skin for a time period of about 5 days. In some aspects, the non-occlusive, pharmaceutical fibrous structure finished with a finishing composition of the disclosure is topically applied to the subject's intact skin for a time period of about 6 days. In some aspects, the non-occlusive, pharmaceutical fibrous structure finished with a finishing composition of the disclosure is topically applied to the subject's intact skin for a time period of about 7 days.

In some aspects, the therapeutically effective amount of the active pharmaceutical ingredient is administered to the subject throughout the time period that the finishing, non-occlusive, pharmaceutical fibrous structure is applied to the subject's intact skin. That is, plasma levels sufficient to treat the subject's condition (either locally, systemically, or both) are substantially consistent throughout the time period. In some aspects, the therapeutically effective amount of the active pharmaceutical ingredient is administered to the subject for about 1 hour to about 72 hours. In some aspects, the therapeutically effective amount of the active pharmaceutical ingredient is administered to the subject for about 8 hours to about 72 hours. In some aspects, the therapeutically effective amount of the active pharmaceutical ingredient is administered to the subject for about 24 hours to about 72 hours. In some aspects, the therapeutically effective amount of the active pharmaceutical ingredient is administered to the subject for about 48 hours to about 72 hours. In some aspects, the therapeutically effective amount of the active pharmaceutical ingredient is administered to the subject for about 1, 2, 3, 4, 5, 6, 7, 8, 9, 10, 11, 12, 13, 14, 15, 16, 17, 18, 19, 20, 21, 22, 23, or about 24 hours. In some aspects, the therapeutically effective amount of the active pharmaceutical ingredient is administered to the subject for at least 4 hours. In some aspects, the therapeutically effective amount of the active pharmaceutical ingredient is administered to the subject for at least 6 hours. In some aspects, the therapeutically effective amount of the active pharmaceutical ingredient is administered to the subject for about 4 days. In some aspects, the therapeutically effective amount of the active pharmaceutical ingredient is administered to the subject for about 5 days. In some aspects, the therapeutically effective amount of the active pharmaceutical ingredient is administered to the subject for about 6 days. In some aspects, the therapeutically effective amount of the active pharmaceutical ingredient is administered to the subject for about 7 days.

In some aspects, the therapeutically effective amount of the active pharmaceutical ingredient is achieved within two hours of applying the finished, non-occlusive pharmaceutical fibrous structure to the subject's intact skin. In some aspects, the therapeutically effective amount of the active pharmaceutical ingredient is achieved within 1 hour of applying the finished, non-occlusive pharmaceutical fibrous structure to the subject's intact skin. In some aspects, the therapeutically effective amount of the active pharmaceutical ingredient is achieved within 30 minutes of applying the finished, non-occlusive pharmaceutical fibrous structure to the subject's intact skin. In some aspects, the therapeutically effective amount of the active pharmaceutical ingredient is achieved within 15 minutes of applying the finished, non-occlusive pharmaceutical fibrous structure to the subject's intact skin. In some aspects, the therapeutically effective amount of the active pharmaceutical ingredient is achieved within 10 minutes of applying the finished, non-occlusive pharmaceutical fibrous structure to the subject's intact skin. In some aspects, the therapeutically effective amount of the active pharmaceutical ingredient is achieved within 5 minutes of applying the finished, non-occlusive pharmaceutical fibrous structure to the subject's intact skin.

The finished, non-occlusive pharmaceutical fibrous structures of the disclosure, for example, those treated with a finishing composition of the disclosure, can be applied to the subject's intact skin continuously throughout the time period. For example, in some aspects, the finished, non-occlusive pharmaceutical fibrous structures of the disclosure, for example, those treated with a finishing composition of the disclosure, can be applied to the subject's intact skin continuously throughout the daytime hours, for example for about 12 hours to about 18 hours. In other aspects, the finished, non-occlusive pharmaceutical fibrous structures of the disclosure, for example, those treated with a finishing composition of the disclosure, can be applied to the subject's intact skin continuously throughout the nighttime hours, for example for about 6 hours to about 12 hours.

In other aspects, the finished, non-occlusive pharmaceutical fibrous structures of the disclosure, for example, those treated with a finishing composition of the disclosure, can be applied to the subject's intact skin intermittently throughout the time period. In these embodiments wherein the structure is intermittently applied during the time period, the subject will experience brief periods where the structure is not applied to the subject's intact skin. These periods can range from 1 minute to 1 hour, for example, 1, 2, 3, 4, 5, 6, 7, 8, 9, 10, 11, 12, 13, 14, 15, 20, 25, 30, 35, 40, 45, 50, 55, or about 60 minutes. The subject may experience one or more of these periods during the time period of application. In other aspects, the subject will experience longer periods where the structure is not applied to the subject's intact skin. These periods can range from over to hour to about 12 hours to about 24 hours, for example, 2, 3, 4, 5, 6, 7, 8, 9, 10, 11, 12, 13, 14, 15, 16, 17, 18, 19, 20, 21, 22, 23, or about 24 hours. In some aspects, the structure is applied to the subject's intact skin for about 12 hours, followed by a period of about 12 hours wherein no structure of the disclosure is applied to the subject's intact skin.

In some aspects, the finished, non-occlusive pharmaceutical fibrous structures of the disclosure, for example, those treated with a finishing composition of the disclosure, are replaced with another finished, non-occlusive pharmaceutical fibrous structure of the disclosure, after the time period. In these aspects, the finished, non-occlusive pharmaceutical fibrous structures of the disclosure are worn in a manner similar to how conventional garments are worn and are replaced with other garments or finished, non-occlusive pharmaceutical structures of the disclosure, worn as garments.

In some aspects of the disclosure, the finished, non-occlusive pharmaceutical fibrous structures are applied to the subject with an intermittent or continuous pressure. In some aspects of the disclosure, the finished, non-occlusive pharmaceutical fibrous structures are applied to the subject with an intermittent pressure. Intermittent pressure may arise, for example, from the subject's usual activities such as walking, sitting, standing, laying, etc. In some aspects of the disclosure, the finished, non-occlusive pharmaceutical fibrous structures are applied to the subject with a constant pressure. Constant pressure may arise, for example, from an external, mechanical application of force to the fibrous structure. According to the disclosure, the amount of active pharmaceutical ingredient administered to the subject from a finished, non-occlusive pharmaceutical fibrous structure of the disclosure will be clinically equivalent to the amount of active pharmaceutical ingredient administered to the subject absent the pressure. That is, the local and/or systemic levels of the active pharmaceutical agent administered will be independent of the pressure (if any) applied to the fibrous structure during the application to the subject's intact skin.

In some aspects, the subject may produce sweat between the intact skin and the finished, non-occlusive pharmaceutical fibrous structure of the disclosure. In these embodiments, the amount of active pharmaceutical ingredient administered to the subject will be clinically equivalent to the amount of active pharmaceutical ingredient administered to the subject, absent the sweat.

Methods of producing the finished, non-occlusive, pharmaceutical fibrous structures of the disclosure are also within the scope of the invention. According to these methods, a fibrous structure (i.e., of synthetic, manmade, and/or natural fibers as described herein) is treated with a finishing composition of the disclosure. The finishing compositions comprise an active pharmaceutical ingredient (or a pharmaceutically acceptable salt thereof) and a solvent. The finishing compositions may optionally include a surfactant, a humectant, a permeation enhancer, or a combination thereof. Finishing compositions of the disclosure are described in more detail supra. According to the disclosure, the fibrous structure is treated with the finishing composition for a time sufficient to finish the fibrous structure with the active pharmaceutic ingredient (or salt thereof).

In some aspects, the fibrous structure is treated with the finishing composition for about 5 minutes to about 24 hours. In some aspects, the fibrous structure is treated with the finishing composition for about 5 seconds to about 24 hours. In other aspects, the fibrous structure is treated with the finishing composition for about 5 minutes to about 90 minutes. In other aspects, the fibrous structure is treated with the finishing composition for about 5 minutes to about 60 minutes. In other aspects, the fibrous structure is treated with the finishing composition for about 5 minutes to about 30 minutes. In other aspects, the fibrous structure is treated with the finishing composition for about 5 minutes to about 15 minutes. In other aspects, the fibrous structure is treated with the finishing composition for about 5 minutes to about 10 minutes. In some aspects, the fibrous structure can be treated for about 1, 5, 10, 15, 20, 25, 30, 35, 40, 45, 50, 55, or about 60 minutes. In other embodiments, the fibrous structure can be treated for about 1.5, 2, 2.5, 3, 3.5, 4, 4.5, or about 5 hours. In other embodiments, the fibrous structure can be treated for about 6, 7, 8, 9, 10, 11, 12, 13, 14, 15, 16, 17, 18, 19, 20, 21, 22, 23, or about 24 hours.

The finishing may be a batch process or a continuous process. In a batch process, the fibrous structure is loaded into a process vessel and removed after the process is completed. In a continuous process, the fibrous structure is continuously transported into a finishing bath or a coating device and subsequently to a drying zone.

In some aspects of the disclosure, a fibrous structure of the disclosure is treated by immersing the fibrous structure into the finishing composition. The fibrous structure can be immersed for a sufficient amount of time, for example, for about 5 seconds to about 24 hours, preferably about 5 minutes to about 24 hours for the batch process. For example, the fibrous structure can be immersed for about 1, 5, 10, 15, 20, 25, 30, 35, 40, 45, 50, 55, or about 60 minutes. In other embodiments, the fibrous structure can be immersed for about 1.5, 2, 2.5, 3, 3.5, 4, 4.5, or about 5 hours. In other embodiments, the fibrous structure can be immersed for about 6, 7, 8, 9, 10, 11, 12, 13, 14, 15, 16, 17, 18, 19, 20, 21, 22, 23, or about 24 hours.

In other aspects of the disclosure, a structure of the disclosure is treated by coating the fibrous structure with the finishing composition. Coating can be achieved using methods known in the art, for example, by spraying or printing. In these methods, the fibrous structure can be treated for a sufficient amount of time, for example, for about 1 second to about 1 hour, preferably about 1 second to about 30 minutes or about 1 second to about 10 minutes. For example, the fibrous structure can be treated for about 1, 5, 10, 15, 20, 25, 30, 35, 40, 45, 50, 55, or about 60 seconds. In other embodiments, the fibrous structure can be treated for about 1, 2, 3, 4, 5, 6, 7, 8, 9, 10, 15, 20, 25, 30, 35, 40, 45, 50, 55, or about 60 minutes.

According to the methods of the disclosure, the pH of the finishing composition can be, or can be optionally adjusted to, a pH that is, for example, pH 7 or above, during the treatment process. For example, the pH of the finishing composition can be adjusted to 7, 7.1, 7.2, 7.3, 7.4, 7.5, 7.6, 7.8, 7.9, 8, 8.1, 8.2, 8.3, 8.4, 8.5, 8.6, 8.7, 8.8, 8.9, 9, 9.5, or about pH 10 during the treatment process. Such pH adjustment may be desirable when the API is provided in a pharmaceutically acceptable salt form. In such instances, the pH of the finishing composition is adjusted so as to free-base the API. As those of ordinary skill in the art will appreciate, pH can be adjust by adding a sufficient amount of aqueous base (or aqueous buffer) to achieve the desired pH. In preferred embodiments wherein the API is provided as a salt form, pH is adjusted with an appropriate amount of an aqueous solution of KOH or an aqueous solution of NaOH or by an organic base such as diethethanolamine, triethanolamine or diethylamine.

In some embodiments, the pH of the finishing composition is less than pH 7 during the treatment process. For example, the pH of the finishing composition is about 3, 3.5, 4, 4.5, 5, 5.5, 6, or about 6.5 during the treatment process. The pH of the finishing composition can be between about 3 to 7. In other aspects, the pH is from about 5 to 7 during the treatment process. In some aspects, the pH of the finishing composition is adjusted to a pH of 7 or below during the treatment process. Finishing compositions having a pH of 7 or below will be particularly useful for fibrous structures that comprise, or that are, cotton. Typically, a finishing compositions is above pH 7 for fibrous structures that comprise, or that are, polyamide and/or polyester.

According to the disclosure, the finishing compositions can be heated to a temperature that is about 20° C. during the finishing treatment process. In some aspects, the finishing composition is heated to a temperature of from about 25° C. to about 100° C. For example, the finishing composition can be heated to a temperature of about 25, 30, 35, 40, 45, 50, 55, 60, 65, 70, 75, 80, 85, 90, 95, or about 100° C. In other aspects, the finishing composition is heated to a temperature of from about 30° C. to about 100° C. In other aspects, the finishing composition is heated to a temperature of from about 30° C. to about 60° C. In other aspects, the finishing composition is heated to a temperature of from about 70° C. to about 90° C. In other aspects, the finishing composition is heated to a temperature of from about 40° C. to about 70° C.

In other aspects of the disclosure, the finishing composition can be cooled during treatment to a temperature that is below 20° C. during the finishing treatment process. In some aspects, the finishing composition be cooled during treatment to a temperature that is between about 0° C. and 20° C. In some aspects, the finishing composition be cooled during treatment to a temperature that is between about 0° C. and 15° C. In some aspects, the finishing composition be cooled during treatment to a temperature that is between about 0° C. and 10° C. In some aspects, the finishing composition be cooled during treatment to a temperature that is about 0, 5, 10, 15, or about 20° C.

After a sufficient time of treatment, either by immersion or otherwise, the finished, non-occlusive, pharmaceutical fibrous structure is removed from the finishing composition. In some aspects, after the fibrous structure is removed from the finishing composition, excess solution can be mechanically removed from the fibrous structure. In those embodiments wherein the finishing compositions comprises a solvent, this process is known as "dewatering" of the finished, non-occlusive pharmaceutical fibrous structure. For example, in these embodiments, the fibrous structure can be spun, for example, by centrifugation, to remove excess finishing composition. In other aspects, the fibrous structure can be hung so as to permit excess finishing composition to drip from the fibrous structure. In other aspects, the fibrous structure can be squeezed so as to permit excess finishing composition be released from the fibrous structure. In other aspects, either following a spinning step or directly following removal from the finishing composition, the fibrous structure is dried. The fibrous structure can be dried by any method known in the art, for example, using heat, reduced pressure and heat, or via sublimation. In some aspects, the fibrous structure is dried at a temperature of from about 150° C. to about 170° C. In other aspects, the fibrous structure is dried at a temperature of from about 30° C. to about 90° C. Such drying conditions, especially secondary to an initial dewatering process, may also be referred to as "curing."

In some aspects, the finished, non-occlusive, pharmaceutical fibrous structure is rinsed after removal from the finishing composition. The finished, non-occlusive, pharmaceutical fibrous structure can be rinsed with a solvent. For example, in some aspects, the finished, non-occlusive, pharmaceutical fibrous structure is rinsed with water. In other aspects, the finished, non-occlusive, pharmaceutical fibrous structure is rinsed with an organic solvent (e.g., chloroform, diethyl ether, tetrahydrofuran, toluene, hexanes, methanol, ethanol, propanol, and the like, and mixtures thereof). In other aspects, the finished, non-occlusive, pharmaceutical fibrous structure is rinsed with a combination of water and an organic solvent (e.g., chloroform, diethyl ether, tetrahydrofuran, toluene, hexanes, methanol, ethanol, propanol, and the like, and mixtures thereof). In other aspects, the finished, non-occlusive, pharmaceutical fibrous structure is rinsed with both water and an organic solvent, for example, a first rinsing with water and a second rinsing with an organic solvent. In other aspects, the finished, non-occlusive, pharmaceutical fibrous structure is first rinsed with an organic solvent and a subsequent rinse is with water.

In some aspects of the disclosure, the rate of release of the active pharmaceutical ingredient from the finished, non-occlusive pharmaceutical fibrous structure of the disclosure can be modified by treating the fibrous structure with a finishing composition of the disclosure, wherein the temperature of the finishing composition during the treatment is between 5° C. and 95° C. In these aspects, increased temperature within this range decreases the in vitro rate of release of the active pharmaceutical ingredient from the finished, non-occlusive, pharmaceutical fibrous structure after 5 minutes in about 500 mL of aqueous NaOH, pH 13, at room temperature and 450 rpm. In some aspects, the temperature of the finishing composition during the treatment is about 5° C. In some aspects, the temperature of the finishing composition during the treatment is about 25° C. In some aspects, the temperature of the finishing composition during the treatment is about 50° C. In some aspects, the temperature of the finishing composition during the treatment is about 55° C. In some aspects, the temperature of the finishing composition during the treatment is about 60° C. In some aspects, the temperature of the finishing composition during the treatment is about 65° C. In some aspects, the temperature of the finishing composition during the treatment is about 70° C. In some aspects, the temperature of the finishing composition during the treatment is about 75° C. In some aspects, the temperature of the finishing composition during the treatment is about 80° C. In some aspects, the temperature of the finishing composition during the treatment is about 95° C.

In some aspects, the non-occlusive, pharmaceutical fibrous structures finished with a treatment comprising a finishing composition of the disclosure will exhibit an in vitro release of 85% or less of the active pharmaceutical ingredient after 5 minutes in 500 mL of aqueous NaOH, pH 13, at room temperature and at 450 rpm under sink conditions (i.e., under conditions of sufficient media to ensure unimpaired dissolution). In some aspects, the non-occlusive, pharmaceutical fibrous structures finished with a treatment comprising a finishing composition of the disclosure will exhibit an in vitro release of 80% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 75% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 70% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 65% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 60% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 55% or less of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 50% or less of the active pharmaceutical ingredient after 5 minutes in 500 mL of aqueous NaOH, pH 13, at room temperature and at 450 rpm.

In some aspects, the non-occlusive, pharmaceutical fibrous structures finished with a treatment comprising a finishing composition of the disclosure will exhibit an in vitro release of 85% or more of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 90% or more of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 95% or more of the active pharmaceutical ingredient after 5 minutes in 500 mL of aqueous NaOH, pH 13, at room temperature and at 450 rpm. In some aspects, the non-occlusive, pharmaceutical fibrous structures finished with a treatment comprising a finishing composition of the disclosure will exhibit an in vitro release of 99% or more of the active pharmaceutical ingredient after 5 minutes in 500 mL of aqueous NaOH, pH 13, at room temperature and at 450 rpm.

Finished, non-occlusive, pharmaceutical fibrous structures produced according to any of the described methods are envisioned. Fibrous structures produced according to the described methods are useful for transdermally administering the APIs. Fibrous structures produced according to the described methods are also useful for dermally administering the APIs. For example, a fibrous structure produced according to a method of the disclosure can be applied to the skin of a subject in need of treatment with the API. In some aspects, the API is delivered systemically, that is, the API achieves an effective therapeutic concentration in the subject's bloodstream. In other aspects, the API is delivered substantially locally, that is, the API does not achieve an effective therapeutic concentration in the subject's bloodstream, but does achieve an effective therapeutic concentration at the locally-administered site.

In some aspects, the subject is in need of treatment for pain. For example, the pain may be neuropathic pain, for example, postherpetic neuralgia. Alternatively, the neuropathic pain can be painful diabetic neuropathy. In other aspects, the pain is pain associated with chemotherapy. In other aspects, the pain is pain associated with HIV. In still other aspects, the pain is erythromelalgia. In other aspects, the pain is pain associated with osteoarthritis. In other aspects, the pain is post-operative pain. In other aspects, the pain is back pain, in particular, lower (lumbar) back pain. The lower back pain may be associated with osteoarthritis or with degenerative disc disease.

In some aspects, the subject is in need of treatment for an infection. For example, the subject may be in need of treatment for a microbial infection, such as a bacterial infection, a viral infection, or a parasitic infection. In other aspects, the subject may be in need of treatment for a fungal infection.

In other aspects, the subject is in need of treatment for an allergy.

In other aspects, the subject is in need of treatment for eczema, for example, atopic dermatitis. In other aspects, the subject is in need of treatment for psoriasis.

In other aspects, the subject is in need of treatment for acute inflammation. In other aspects, the subject is in need of treatment for chronic inflammation.

In other aspects, the subject is in need of treatment with an API having anti-proliferative properties, e.g. treatment of the subject with an anti-proliferative API is indicated. In other aspects, the subject is in need of treatment with an API having anti-angiogenic, e.g. treatment of the subject with an anti-angiogenic API is indicated. In other aspects, the subject is in need of treatment with an API having anti-cancer properties, e.g. treatment of the subject with an anti-cancer API is indicated.

"Tensile strength" refers to a stress/strain property of a material and can be measured by a tensile testing machine such as a Testometric® M350 Universal Testing Machine using an accepted standard method such as ASTM D5034-09. Results may be reported in load (kgf) versus elongation (%). "Strength" refers to resistance to break of a material under tensile load and can be measured by a tensile testing machine such as a Testometric® M350 Universal Testing Machine using an accepted standard method such as ASTM D5034-09. Results may be reported in peak load (kgf).

"Softness" or "stiffness" or "flexibility" refers to the ease of deformation and can be measured by a Shirley bending length tester using an accepted standard method such as ASTM method D1388-18. Results may be reported in bending length (mm).

"Breathability" or "air permeability" refers to the ability of a material to allow air flow through it under a given pressure drop and can be measured by an air permeability tester such as YG461E/II Digital Fabric Air Permeability Tester using an accepted standard method such as ASTM D737-09. Results may be reported in air permeability flow rate (mm/sec).

"Vapor transport" refers to the ability of a material to allow moisture vapor flow through it under given conditions and can be measured by a moisture vapor transport rate measuring apparatus such as Ludlow Corp. CS-141 Moisture Transmission Tester using an accepted standard method such as ASTM E96-80. Results may be reported in moisture flow rate ($gr/m^2/24$ hrs) or as the evaporation % weight loss.

"Leveling" refers to the uniformity of finishing in terms of the differing amount of material deposited on different areas of the fibrous structure and can be measured by extraction, color difference spectroscopy or gravimetrically. Segments of the fibrous structure are examined for the local concentrations of the material and results reported in term of relative standard deviation (RSD).

ASPECTS

Aspect 1. A method of impregnating a textile with an active pharmaceutical ingredient
comprising
combining
a surfactant;
optionally, a humectant;
optionally, a permeation enhancer;
the active pharmaceutical ingredient or a pharmaceutically acceptable salt thereof;
and
an aqueous solvent;
to form an impregnation solution;
heating the impregnation solution;
immersing the textile in the impregnation solution for a time sufficient to impregnate the textile with the active pharmaceutical ingredient;
optionally adjusting the pH of the impregnation solution to a pH of 7 or above; and
removing the textile from the impregnation solution.

Aspect 2. The method of Aspect 1, wherein the impregnation solution comprises from about 0.1% (w/w) to about 5% (w/w) of the surfactant.

Aspect 3. The method of any one of the preceding Aspects, wherein the surfactant is a nonionic surfactant, preferably a fatty acid ester of glycerol or a fatty acid ester of sorbitol or a combination thereof.

Aspect 4. The method of Aspect 3, wherein the surfactant is a fatty acid ester of sorbitol, preferably a polysorbate.

Aspect 5. The method of any one of the preceding Aspects, wherein the impregnation solution comprises a humectant.

Aspect 6. The method of Aspect 5, wherein the impregnation solution comprises about 5% (w/w) to about 25% (w/w) of the humectant.

Aspect 7. The method of any one of Aspects 5 or 6, wherein the humectant is a polyalkene glycol, a polymeric polyol, a sugar alcohol, or a combination thereof.

Aspect 8. The method of Aspect 7, wherein the humectant is a polyethylene glycol, preferably polyethylene glycol 400.

Aspect 9. The method of any one of the preceding Aspects, wherein the impregnation solution comprises a permeation enhancer.

Aspect 10. The method of Aspect 9, wherein the impregnation solution comprises from about 5% (w/w) to about 15% (w/w) of the permeation enhancer.

Aspect 11. The method of any one Aspects 9 or 10, wherein the permeation enhancer is a monomeric glycol, a monomeric alcohol, a pyrrolidone, or a combination thereof.

Aspect 12. The method of Aspect 11, wherein the permeation enhancer is a monomeric glycol, preferably propylene glycol.

Aspect 13. The method of any one of the preceding Aspects, wherein the impregnation solution comprises from about 0.1% (w/w) to about 25% (w/w) of the active pharmaceutical ingredient or the pharmaceutically acceptable salt thereof.

Aspect 14. The method of any one of the preceding Aspects, wherein the active pharmaceutical ingredient is a lipophilic active pharmaceutical ingredient.

Aspect 15. The method of any one of the preceding Aspects, wherein the active pharmaceutical ingredient is lidocaine, prilocaine, bupivacaine, mepivacaine, ropivacaine, articaine, tetracaine, capsaicin, diclofenac, menthol, methyl salicylate, salicylic acid, or a pharmaceutically acceptable salt thereof, or a combination thereof.

Aspect 16. The method of any one of the preceding Aspects, wherein the active pharmaceutical ingredient is lidocaine, prilocaine, or a pharmaceutically acceptable salt thereof, or a combination thereof.

Aspect 17. The method of any one of the preceding Aspects, wherein the textile comprises synthetic fibers, cellulose fibers, animal fibers, insect fibers, or a combination thereof.

Aspect 18. The method of any one of the preceding Aspects, wherein the textile comprises polyamide fibers, nylon fibers, spandex fibers, lycra fibers, wool fibers, fleece fibers, silk fibers, cotton fibers, polyester fibers, or a combination thereof.

Aspect 19. The method of any one of the preceding Aspects, wherein the textile is in the form of a sheet or a garment.

Aspect 20. The method of any one of the preceding Aspects, wherein the impregnation solution is heated to a temperature of from about 30° C. to about 100° C., preferably between about 40° C. and about 70° C.

Aspect 21. The method of any one of the preceding Aspects, wherein the time is from about 5 minutes to about 24 hours, preferably about 15 minutes to about 90 minutes.

Aspect 22. The method of any one of the preceding Aspects, further comprising drying of the textile after its removal from the impregnation solution.

Aspect 23. A textile impregnated with an active pharmaceutical ingredient prepared according to any one of the preceding Aspects.

Aspect 24. A method of transdermally or dermally administering an active pharmaceutical ingredient to a subject in need of treatment comprising applying the textile of Aspect 23 to the skin of the subject.

Aspect 25. The method of Aspect 24, wherein the subject is in need of treatment for pain.

Aspect 26. The method of Aspect 25, wherein the pain is neuropathic pain, preferably postherpetic neuralgia or painful diabetic neuropathy, pain associated with chemotherapy, pain associated with HIV, erythromelalgia, pain associated with osteoarthritis, or lower back pain.

The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Polyethylene glycol 400 (100 g), propylene glycol (100 g), Polysorbate 80 (20 g), and lidocaine HCl (100 g) were added into a beaker. Double distilled water was then added to the beaker, up to final weight of 1000 g. The resulting mixture was stirred and heated to 50° C. to form a clear and homogenous solution. The solution was divided into two aliquots of 500 g, each. A polyamide fibrous structure (~50 g) was added into each of the aliquots. A 45% w/w potassium hydroxide solution was added to the aliquots, while stirring, until pH reached 7-8 pH values. The aliquots were then placed in a Labomat type <BFA> dying apparatus (Mathis AG, Switzerland) for 30 minutes, at 50° C., while rotating clockwise and anticlockwise. The fibrous structures were removed from the solutions, spun to remove excess solution, and placed into an AEG combined washing-drying machine to dry. Drug content on the finished fibrous structure was estimated by fibrous structure weight gain. Amounts of lidocaine finished on the fibrous structures was further analyzed using HPLC or by UV spectrophotometric techniques.

A similar procedure was used to impregnate a polyamide fibrous structure with lidocaine, bupivacaine, mepivacaine, prilocaine, ropivacaine, or articaine, each example using a solution including 10% (w/w) of the API as its HCl salt. See FIG. 1A.

Figure 1B:
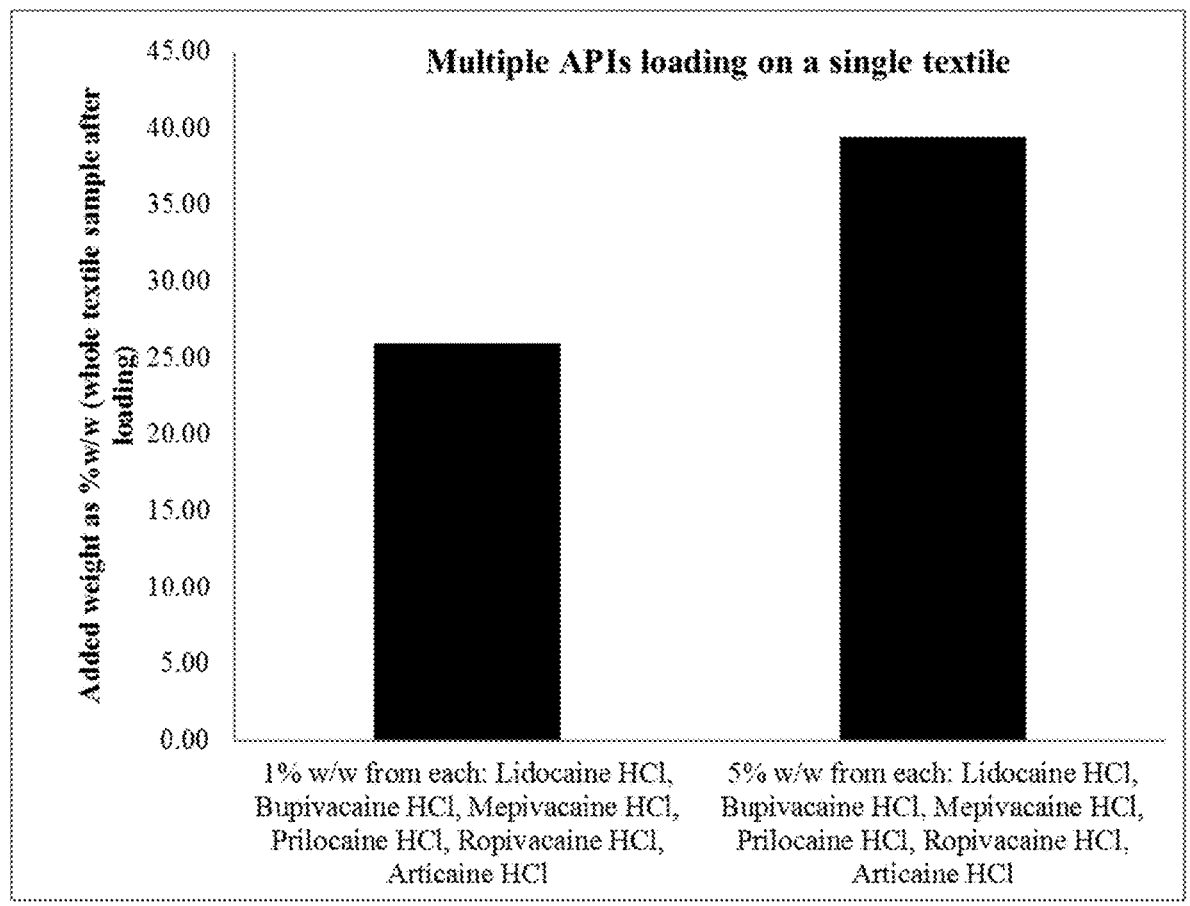
FIG. 1B depicts final fibrous structure weight as compared to original fibrous structure weight, prepared using methods of the disclosure.

A fibrous structure finished with six APIs (lidocaine, bupivacaine, mepivacaine, prilocaine, ropivacaine, and articaine) was prepared using a similar procedure, using a solution including 1% (w/w) or 5% (w/w) of the APIs as their HCl salts. See FIG. 1B.

Example 2

Lidocaine base was finished on a polyamide fibrous structure using a procedure similar to that described in Example 1, but starting with lidocaine free base and without pH adjustment. Instead of 50° C., the finishing composition was heated to 60° C.

Example 3

A combination of lidocaine and prilocaine was finished on a polyamide fibrous structure using a procedure similar to that described in Example 1, but with 15% (w/w) of lidocaine HCl and 15% (w/w) of prilocaine HCl.

Example 4

Figure 2:
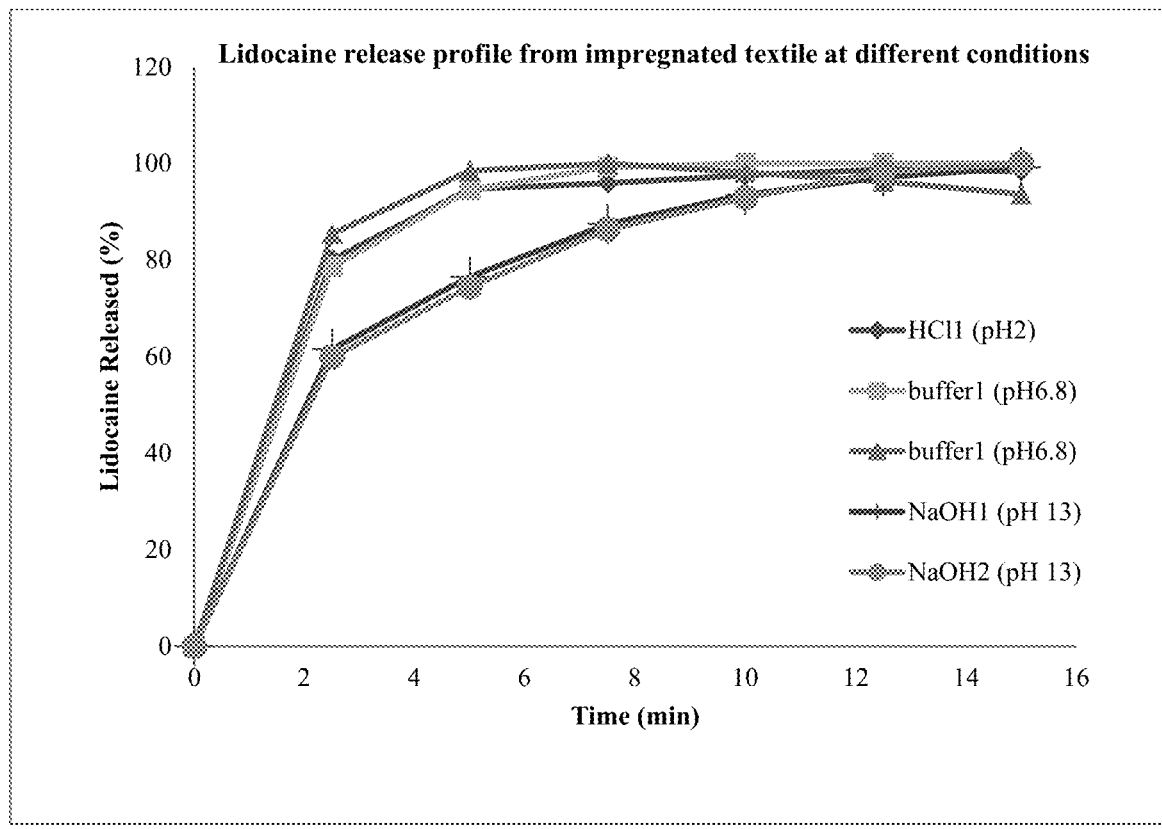
FIG. 2 depicts the percentage of API released over time, as a function of pH.

This study was conducted to characterize drug release profiles from a fibrous structure at different pH conditions. 708-DS Dissolution Apparatus 2 (Agilent Technologies Inc., Palo Alto, Calif.) connected to Agilent 8453 Spectrophotometer and UV-visible ChemStation for Dissolution testing were used. Three different pH solutions (pH 2 (n=1), 6.8 (n=2), and 13 (n=2)) were added into separate 900 mL beakers. Substantially identical, lidocaine-loaded, fibrous structures were added and the drug levels in the solutions were measured using an on-line UV spectrophotometer. Results are presented in FIG. 2.

Example 5

Figure 3:
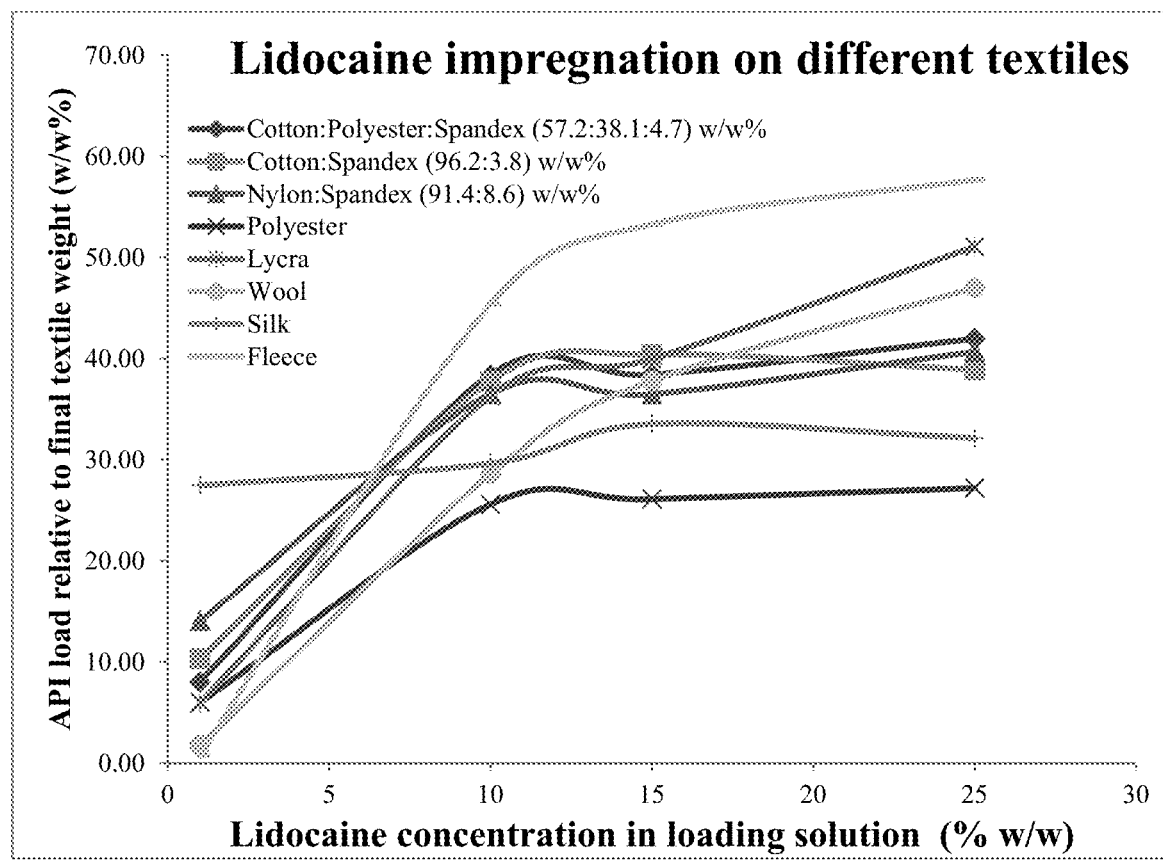
FIG. 3 depicts mean lidocaine finishing of different fibrous structures, using methods of the disclosure.
Figure 4A:
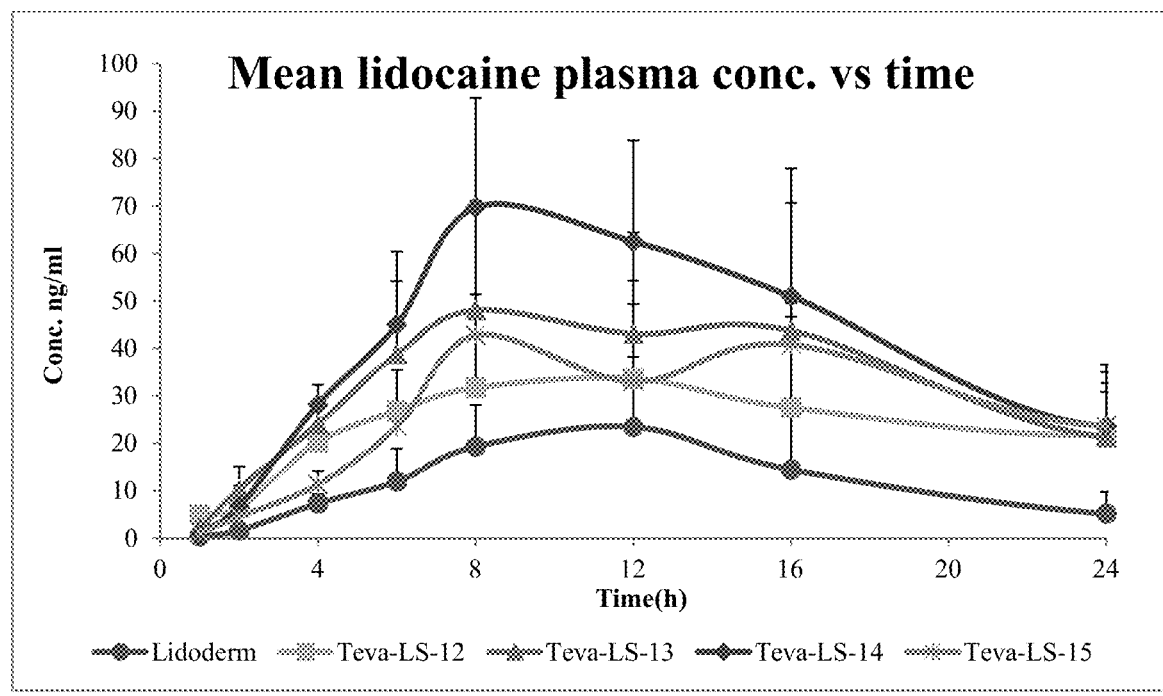
FIG. 4A depicts mean lidocaine plasma concentration versus time for embodiments of the disclosure, as compared to a reference.
Figure 4B:
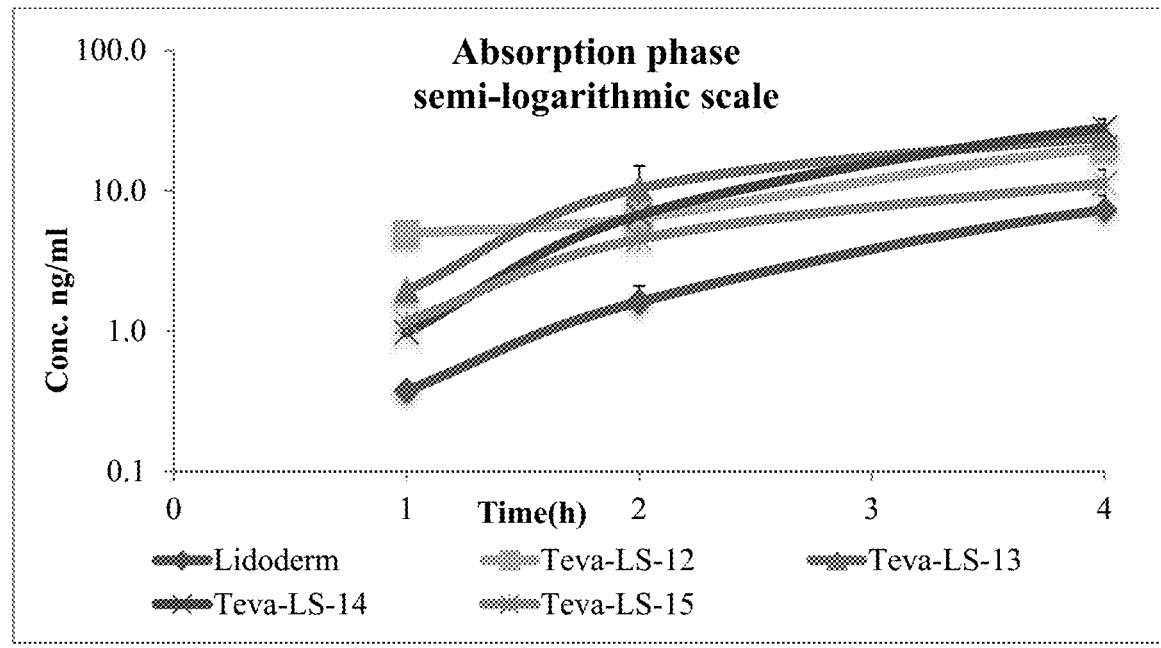
FIG. 4B depicts mean lidocaine plasma concentration over time for embodiments of the disclosure, as compared to a reference.
Figure 4C:
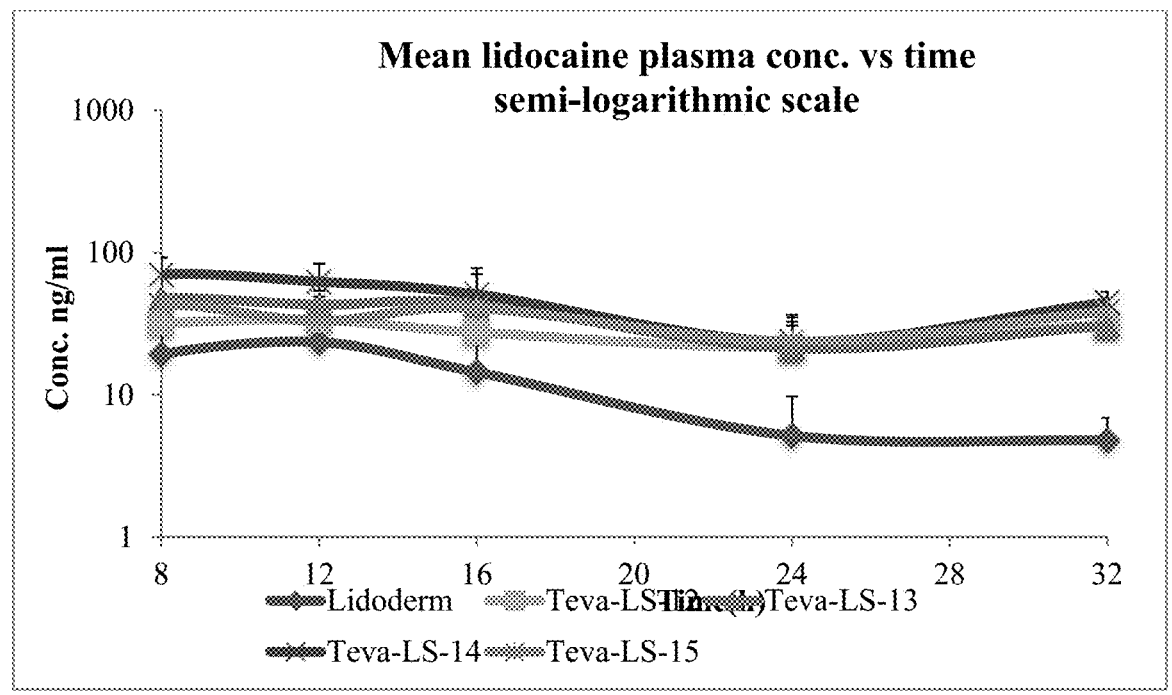
FIG. 4C depicts mean lidocaine plasma concentration over time for embodiments of the disclosure, as compared to a reference.
Figure 5:
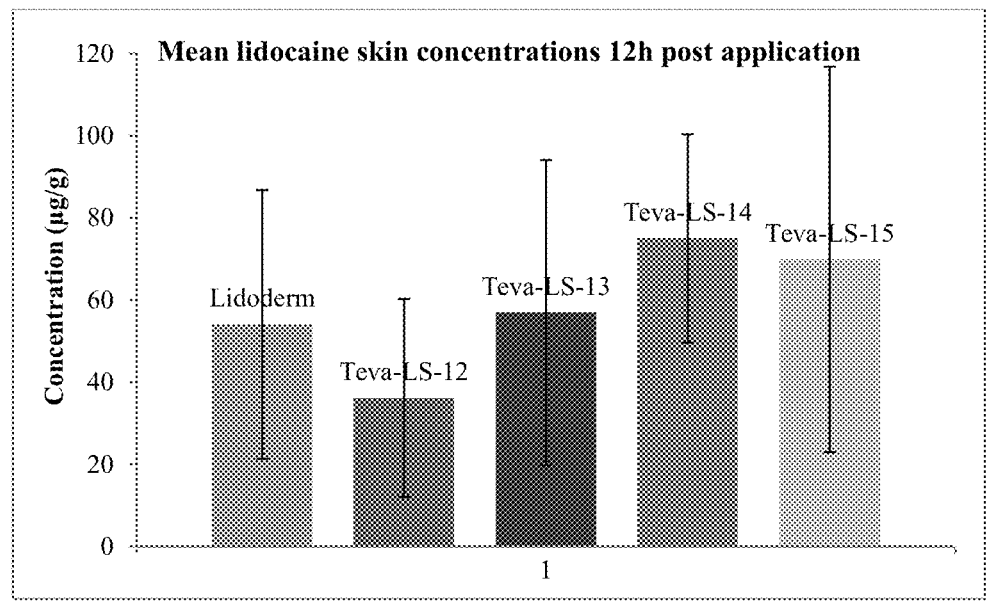
FIG. 5 depicts mean lidocaine skin concentrations after exposure to embodiments of the disclosure, as compared to a reference.
Figure 6:
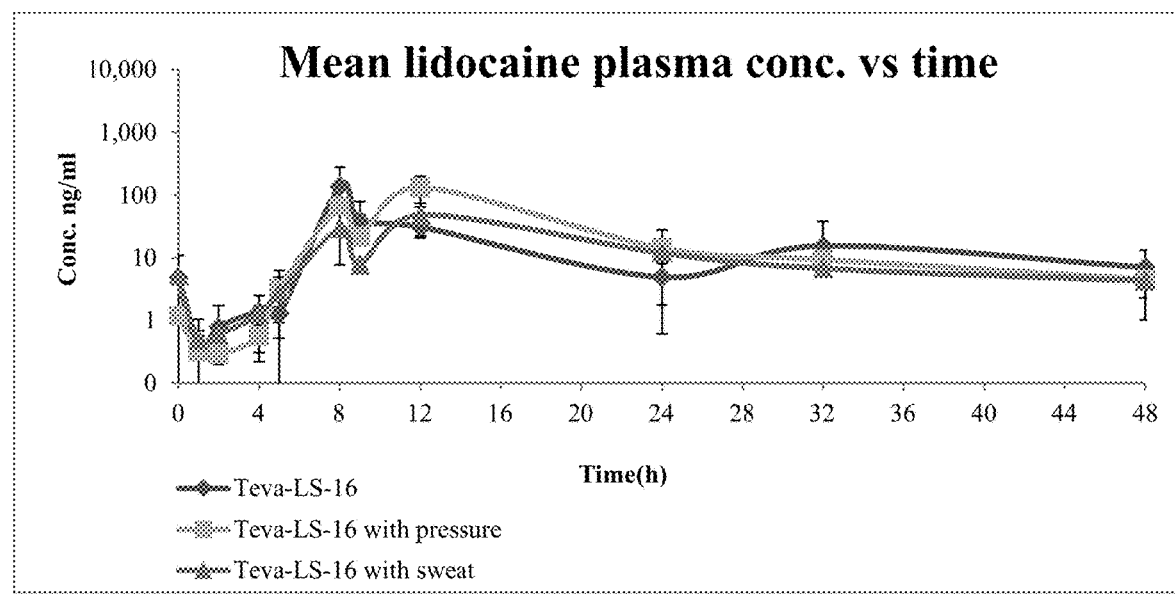
FIG. 6 depicts mean lidocaine plasma concentration over time for an embodiment of the disclosure.
Figure 7:
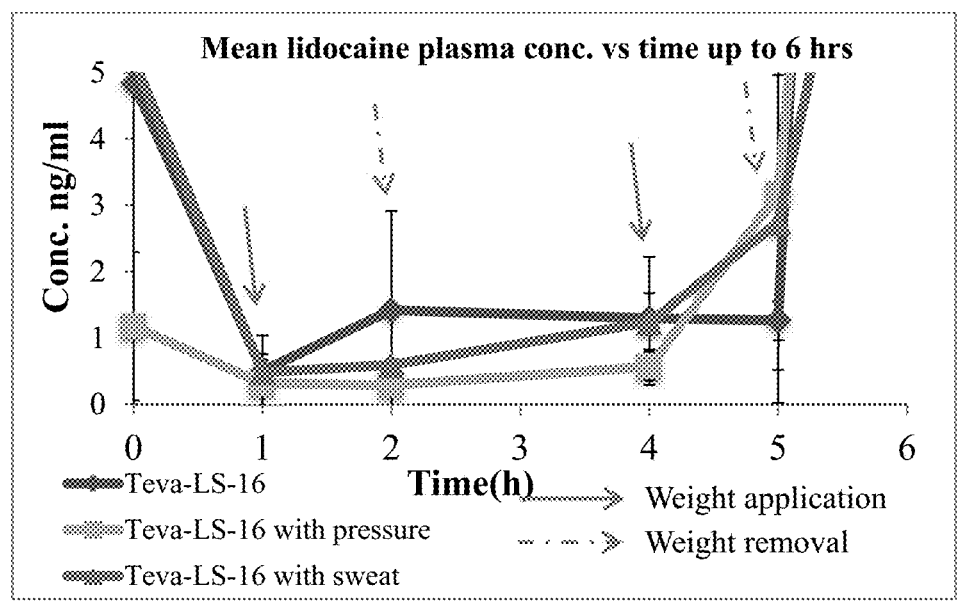
FIG. 7 depicts mean lidocaine plasma concentration over time for an embodiment of the disclosure.
Figure 8:
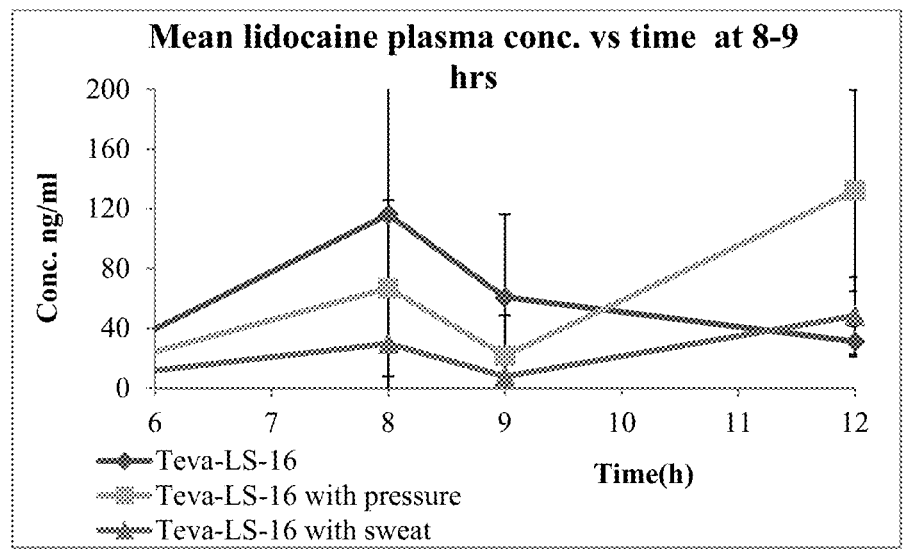
FIG. 8 depicts mean lidocaine plasma concentration over time for an embodiment of the disclosure.
Figure 9A:
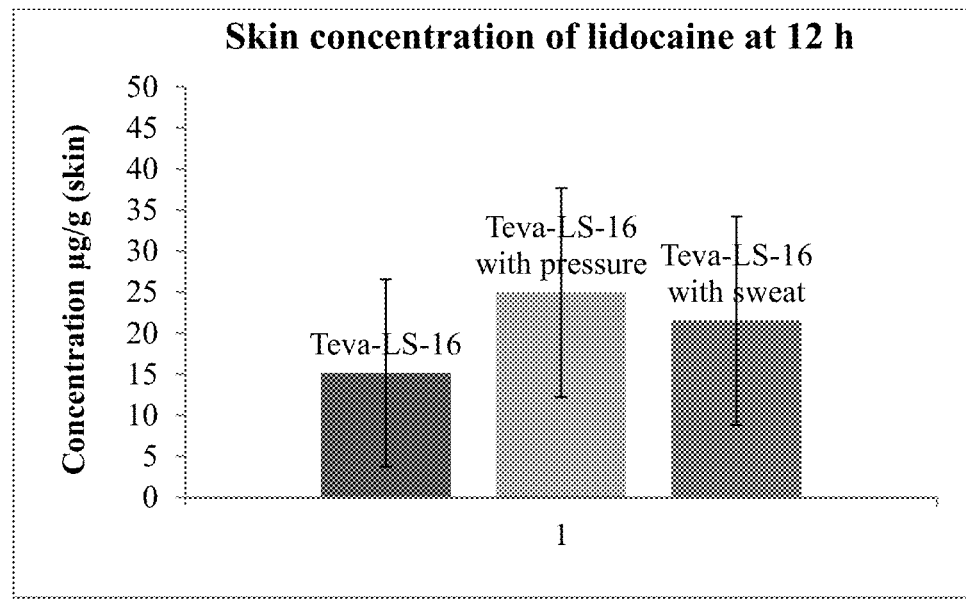
FIG. 9A depicts mean lidocaine skin concentrations after exposure to embodiments of the disclosure, as compared to a reference.
Figure 9B:
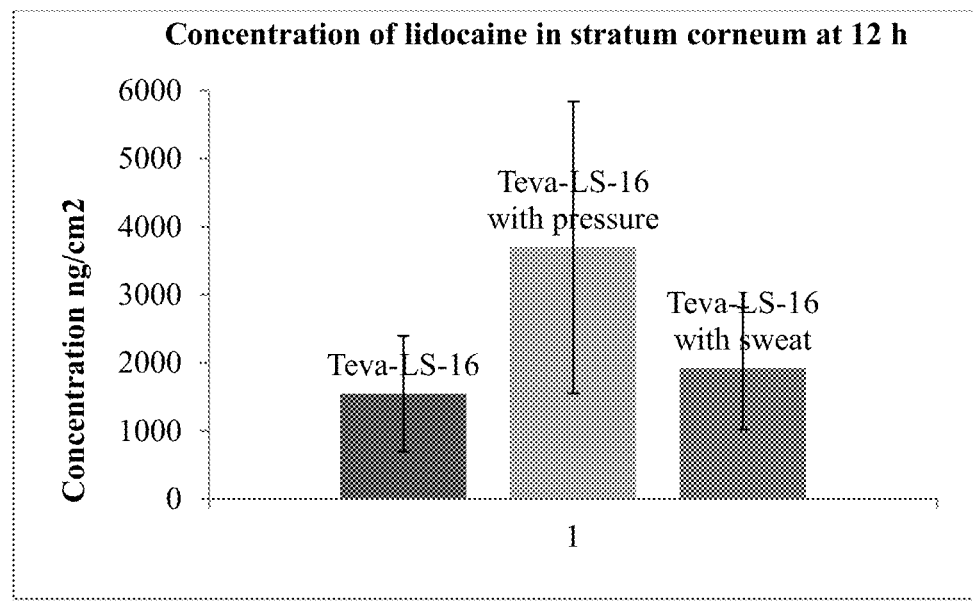
FIG. 9B depicts mean lidocaine stratum corneum concentrations after exposure to embodiments of the disclosure, as compared to a reference.

Lidocaine base was finished on different kinds of fibrous structures using a procedure similar to that described in Example 1 at different lidocaine HCl concentrations ranged from 1 to 25 w/w %. (See FIG. 3)

Example 6

Skin levels and plasma pharmacokinetic profiles of lidocaine after application of an finished fibrous structure with lidocaine in a mini pig model were tested. A commercially available 5% lidocaine patch was used as a reference (Lidoderm®, Endo pharmaceuticals, Inc, Chadds Ford, Calif.). Two lidocaine patches (total of 1400 mg lidocaine; 280 cm$^2$ surface area) were compared with finished fibrous structures containing ~3000 mg lidocaine HCl in each prototype; 280 cm$^2$ surface area. See Table 1.

TABLE 1

| Examples | Lidocaine* | PEG400** | Propylene glycol** | Polysorbate80** | Sorbitol** |
|---|---|---|---|---|---|
| LS-12 | about 3000 mg | | | 2% (w/w) | |
| LS-13 | about 3000 mg | | 10% (w/w) | 2% (w/w) | |
| LS-14 | about 3000 mg | 10% (w/w) | 10% (w/w) | 2% (w/w) | |
| LS-15 | about 3000 mg | | 10% (w/w) | 2% (w/w) | 10% (w/w) |
| LS-16 | about 5000 mg | 10% (w/w) | 10% (w/w) | 2% (w/w) | |

*lidocaine content on finished fibrous structure, as measured by HPLC
**content in finishing composition Test articles were placed on the dorsal skin of the tested animals. Test and reference article patches were applied to cover 280 cm$^2$ of the application site. Prior to application of the reference patch or the test articles, dose sites were gently wiped with tap water-moistened paper tissues/towels or with gauze pads. The application site was completely dry before application of the patches. No soaps or any cleansing agents were used to clean the application site. During the dose application, gloves were changed between each animal treatment by the study-performing technicians.

In general, each reference patch (LIDODERM® (lidocaine patch)) was 140 square centimeters in area (containing 700 mg lidocaine) and had one piece of release liner that covered the entire adhesive layer. The sticky side of two patches was applied to the pig's skin. To ensure the patch reference article was in good contact with the application site, the patch was gently smoothed out after application to ensure no air bubbles had been entrapped under the surface of the patch, and then gently pressed around the edges for at least 30 seconds. Two reference article patches were applied to the width of the application site, directly adjacent to each other, and were covered with a gauze pad. To ensure fixation, the gauze pad was secured with Vet-Flex.

The test article was a fibrous structure finished with Lidocaine of 280 square centimeter area. The test article was attached with pins and adhesive tape to Velcro strips that could wrap around the animal's abdomen in order to affix the test article. The region of the fibrous structure finished with Lidocaine was positioned over the application site (mid-abdomen just lateral of the spine on the left side).

The test article was held in contact with the skin by applying adhesive tape (3M) on the edges of the test fibrous structure and secured with Vet Flex tape but without covering the portion of the fibrous structure laden with Lidocaine.

The administration period for the reference/test articles was 12 h. Skin biopsies were collected after 12 hrs. Plasma samples were taken up to 32 hours post application. Lidocaine levels in skin biopsies and in plasma were analyzed. See Table 2, below. Results are depicted in FIGS. 4A, 4B, 4C, and 5.

TABLE 2

| Treatment | Duration and Area of Application | Dose and Drug Load | Plasma Collection | Skin Collection | Skin local tolerance |
|---|---|---|---|---|---|
| LIDODERM ® 2 patches Teva-LS-12 Teva-LS-13 Teva-LS-14 Teva-LS-15 | 12 h 280 cm² (7.5% BSA) | 1400 mg 5 mg/cm² 3000 mg 11 mg/cm² | 0, 1, 2, 4, 6, 8, 10, 12, 16, 14, and 32 h | Sc, full thickness skin at 12 h | Draze modified test at 12 h |

Results-Mean Plasma Concentrations vs. Time

Example 7

Local pressure and human sweat effects on LS-16 prototype (see Table 1) were investigated. Skin samples as well as blood samples for investigating the plasma pharmacokinetic profiles of lidocaine after application of lidocaine-finished fibrous structure in Gottingen minipigs were collected. An finished fibrous structure containing 5000 mg lidocaine was applied to each animal; test article surface area was 280 cm². Individual test article doses were administered on a fixed basis (1 test article/animal) via topical application. At least 1 day prior to the day of dosing, an area of dorsal skin larger than, but including the application site, was clipped to become free of hair and to allow uniform application of doses and clear observation of the application site. Prior to application of the test articles, dose sites were gently wiped with tap water-moistened gauze pads. The application site was completely dry before application of the test articles. No soaps or any cleansing agents were used to clean the application site.

The test articles were supplied as a fibrous structure finished with Lidocaine of 280 cm², attached with pins and adhesive tape to Velcro strips that wrapped the animal around its abdomen in order to affix the test article. The region of the fibrous structure finished with Lidocaine was positioned over the application site perpendicular to the spine. The test article was held in contact with the skin by applying adhesive tape on the edges of the test fibrous structure and secured with Vet Flex tape without covering the portion of the fibrous structure laden with Lidocaine.

The test article was applied for approximately 12 hours. At the end of the application period, the dressing was removed and skin irritation examination was performed using the modified Draize scoring system. For each group, the dose site was scored/graded predose and at 12 hours postdose (immediately following patch removal).

Evaluation of Skin Reactions Using Draize Scoring System

Erythema (Redness) and Eschar (Scabbing) Formation

| | |
|---|---|
| 0 | Normal |
| 1 | Very slight erythema (barely perceptible) |
| 2 | Well-defined erythema |
| 3 | Moderate-to-severe erythema |
| 4 | Severe erythema (beet redness) to slight eschar formation (injuries in depth) |

-continued

Evaluation of Skin Reactions Using Draize Scoring System

Edema (Swelling) Formation

| | |
|---|---|
| 0 | Normal |
| 1 | Very slight edema (barely perceptible) |
| 2 | Slight edema (edges of area well defined by definite raising) |
| 3 | Moderate edema (area raised approximately 1 mm) |
| 4 | Severe edema (raised more than 1 mm and extending beyond area of exposure) |

This study showed that mild scoring for erythema noted score of "2" for one minipig treated with LIDODERM. Other animals were scored "0" or "1" for erythema. All animals were scored "0" for edema and eschar. After test articles removal, skin was cleaned followed by skin sample collection process. Skin stripping and skin biopsy samples were taken.

Pressure Application:

Pressure was applied to the dose application area on 3 separate occasions for duration of approximately 1 hour each time using a sand weight 0.75 kg. The weight was applied at the following time ranges relative to the time of the dose application: 1-2 hours postdose, 4-5 hours postdose and 8-9 hours postdose. The weight was applied across the test article perpendicular to the spine. See FIGS. 6, 7, 8, 9A, and 9B.

Human Sweat Application:

Normal Sweat Human Fluid from individual donors was purchased from mybiosource (San Diego, Calif.) and was sprayed on the test article at approximately 1 and 4 hours after the dose application. At each occasion of human sweat application approximately 1.5 g of the human sweat was uniformly sprayed over the test article (approx. 280 cm²). The test article was covered with occlusive dressing. The dressing was removed after approximately 1 hr. See FIGS. 6, 7, 8, 9A, and 9B.

Example 8

The study design, including group designations and dose levels, is shown in Table 3.

TABLE 3

| Group | No. of Animals | Treatment | No. of Test Articles/dose | No. of Doses | Duration of each dose | Target Dose Level (mg/animal) |
|---|---|---|---|---|---|---|
| 1 | 3 | LIDODERM ® | 2[a] | 4[a] | 24 h | 1400 |
| 2 | 5 | Teva-LS-16 | 1[b] | 4[b] | 24 h | 5000 |

Note:
[a]Two patches were applied approximately every 24 hours for 96 hours (total of 4 applications).
[b]One test article was applied approximately every 24 hours for 96 hours (total of 4 applications).

Evaluation of local tolerance and PK of lidocaine following a continuous application (every 24 hours) of 4 doses of fibrous structure relative to LIDODERM® in mini-pigs (n=3-5) was conducted. The treatment duration was 96 hours. The tested products were replaced every 24 hours. Endpoints were plasma PK, skin PK, skin local tolerance Draize test. Reference articles (LIDODERM® patch) were administered as 2 patches/animal/application via topical application. Individual Teva-LS-16 test article doses were administered on a fixed basis 1 test article/animal/application via topical application.

At least 1 day prior to the day of dosing, an area of dorsal skin larger than, but including the application site, was clipped free of hair to allow uniform application of doses and clear observation of the application site. Prior to application of the test article, dose sites were gently wiped with tap water-moistened gauze pads. The application site was completely dry before application of the patches. No soaps or any cleansing agents were used to clean the application site. The test article used was a fibrous structure finished with Lidocaine of 280 cm$^2$ area and attached with pins and adhesive tape to Velcro strips that used to wrap the animal around its abdomen in order to affix the test article. The region of the fibrous structure finished with Lidocaine was positioned over the application site perpendicular to the spine. The test article was held in contact with the skin by applying adhesive tape on the edges of the test fibrous structure and secured with Vet Flex tape that did not cover the portion of the fibrous structure laden with the drug. The test articles were applied approximately every 24 hours up to 96 hours (Groups 1 and 2, total of 4 applications).

Figure 10:
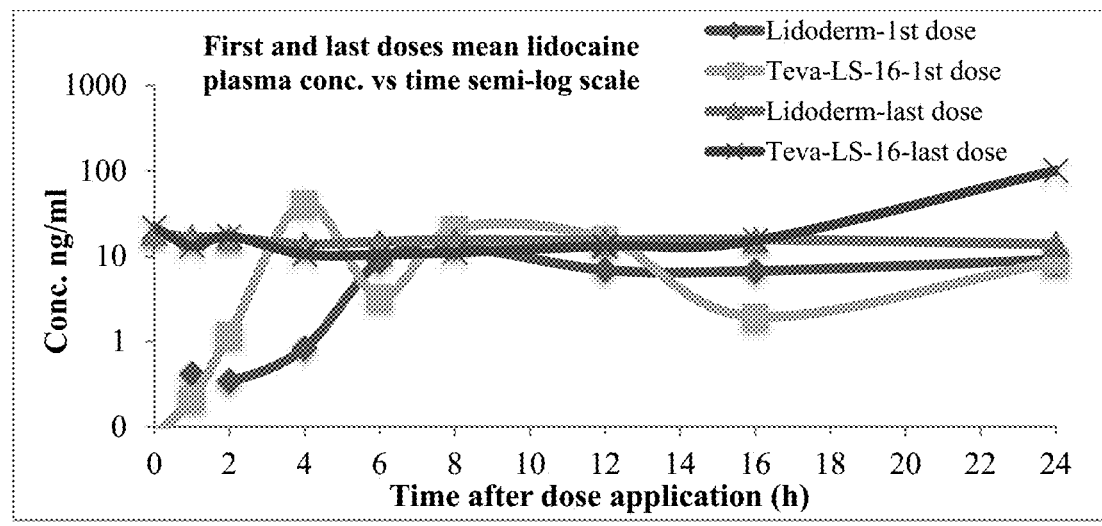
FIG. 10 depicts mean lidocaine plasma concentration over time for an embodiment of the disclosure.
Figure 11:
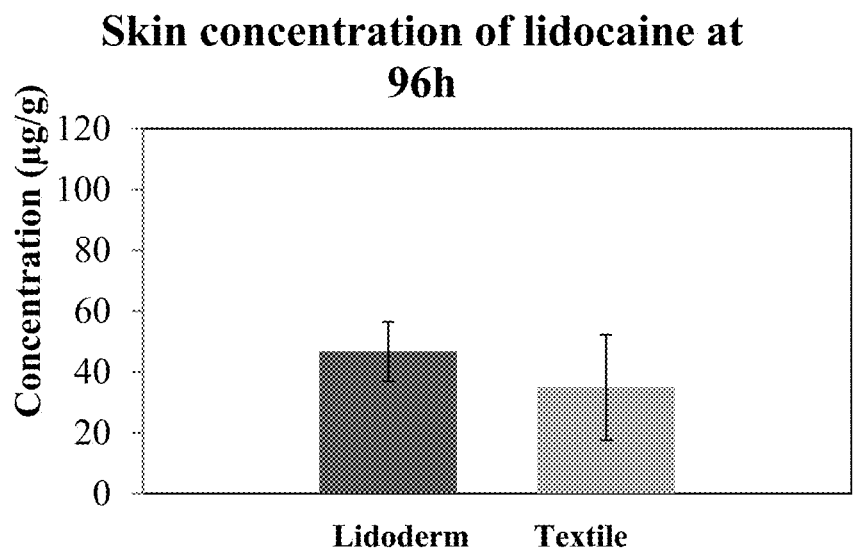
FIG. 11 depicts mean lidocaine skin concentrations after exposure to embodiments of the disclosure for 96 h, as compared to a reference.

At the end of the application period, the test/reference articles were removed; the application sites were scored, and then gently wiped with gauze pads. After cleaning, skin samples were collected (skin stripping and skin biopsies). Results are depicted in FIGS. 10 and 11.

Figure 12A:
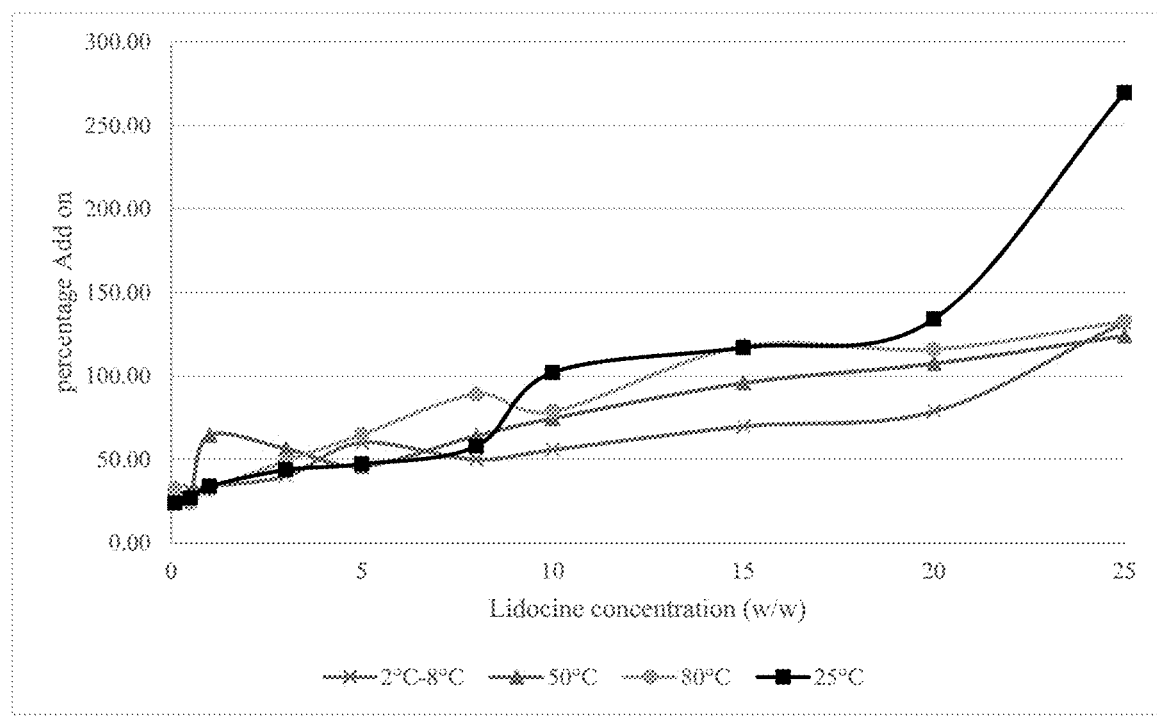
FIG. 12A depicts percentage Add-on using increasing concentrations of lidocaine in finishing compositions at 2-8° C., 50° C., 80° C., and 25° C.
Figure 12B:
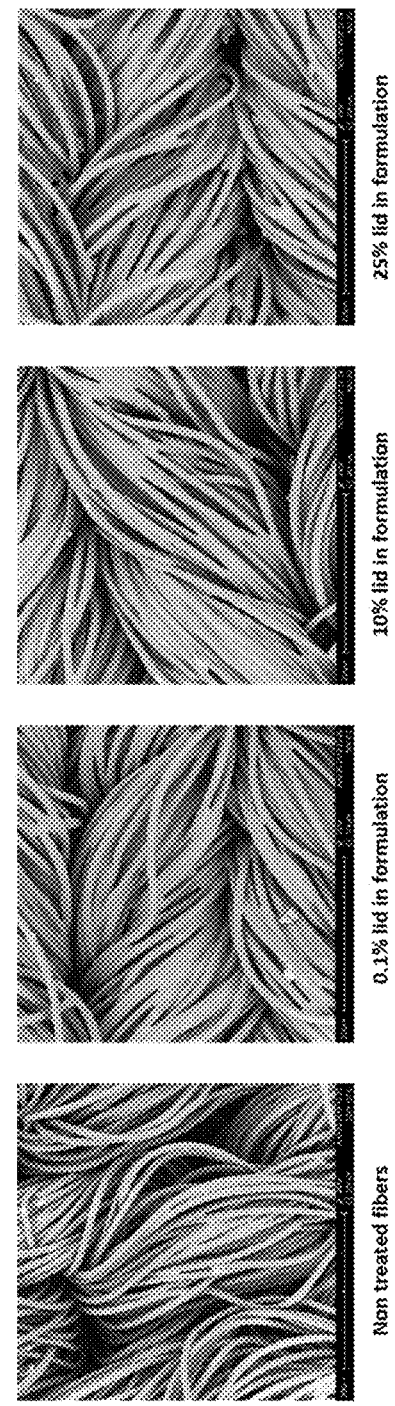
FIG. 12B depicts scanning electron microscope pictures of 80° C. finished and unfinished fibrous structures.

Example 9: Study of Different Temperatures and API Concentrations on Fibrous Structure Loading 10 g aqueous compositions of 10% PEG 400, 10% propylene glycol and 2% Polysorbate 80 together with lidocaine at concentrations between 0.1% to 25% were added to 20 ml vessels and placed on controlled temperature, 400 RPM, stirrer plates at either 2-8° C., room temperature, 50° C. or 80° C. After reaching the required temperature, 0.5 g samples of 91.4% polyamide/8.6% elastane were added to the vessels and mixed for a further hour. The samples were then removed from their vessels, weighed and left to dry overnight at room temperature before their dry weight and percentage Add on were determined. The results are shown in Table 4 and FIGS. 12A and 12B.

TABLE 4

| Lidocaine % (w/w) | 2-8° C. % Add on | RT % Add on | 50° C. % Add on | 80° C. % Add on |
|---|---|---|---|---|
| 0.1 | 25.93 | 23.91 | 32.73 | 32.20 |
| 0.5 | 31.48 | 26.79 | 29.79 | 23.91 |
| 1 | 34.00 | 33.96 | 64.44 | 32.14 |
| 3 | 40.00 | 43.75 | 56.52 | 48.98 |
| 5 | 60.00 | 47.27 | 46.00 | 64.91 |
| 8 | 50.00 | 58.00 | 64.15 | 89.13 |
| 10 | 55.77 | 102.04 | 74.55 | 78.72 |
| 15 | 69.77 | 116.98 | 95.74 | 117.78 |
| 20 | 78.72 | 134.04 | 107.41 | 116.00 |
| 25 | 132.08 | 269.57 | 124.00 | 132.56 |

Example 10. Study of Squeezing and Washing on Fibrous Structure Loading 100 ml aqueous compositions of 10% PEG400, 10% propylene glycol and 2% Polysorbate 80 together with lidocaine at concentrations of 0.1% or 25% were added to 250 ml vessels and placed on controlled temperature stirrer plates and heated to either 25° C. or 80° C. Once the temperature had been reached, 6 samples of 91.4% polyamide/8.6% elastane were added to each vessel. After a further hour, samples were then either a) left to dry at room temperature, b) squeezed—the sample was placed between the 2 layers of blotting paper and pressed for 2 min by the flat plate with a weight of 2.2 kg and then allowed to dry at room temperature, c) washed—using 200 ml water, the sample was mixed for 1 min in solution using a 400 RPM magnetic bar stirrer and then allowed to dry at room temperature or d) washed in 0.1M NaOH—the sample was mixed for 1 minute in 200 ml 0.1M NaOH solution that had been cooled to about 17° C. using a 400 RPM magnetic bar stirrer and then allowed to dry at room temperature. After drying, the sample's dry weight and percentage Add on were determined. The results are shown in Table 5.

TABLE 5

| | | % Add on | | | |
|---|---|---|---|---|---|
| temperature | lidocaine concentration | dried at RT | squeezed | washed in water | washed in NaOH |
| 25° C. | 0.1 | 42.31 | 7.23 | 1.40 | 2.74 |
| | 25 | 118.56 | 43.01 | 3.02 | 7.05 |
| 80° C. | 0.1 | 53.21 | 6.30 | 2.02 | 2.97 |
| | 25 | 136.85 | 112.83 | 83.44 | 55.28 |

The lidocaine concentration in the mother liquor was assayed for the 0.1% samples using HPLC (Luna C18(2), 100 Å, 5 µm, 250×4.6 mm (Phenomenex), mobile phase-water with acetic acid (pH 3.4) (80%) and Acetonitrile (20%), UV detection at 254 nm at room temperature, flow rate of 1.5 mL/min) and found to be 0.995 mg/ml for the 0.1%/25° C. liquor and 0.862 mg/ml for the 0.1%/80° C. liquor indicating that approximately 0.5 mg (0.5%) of lidocaine was loaded from the 0.1%/25° C. sample and 13.8 mg (14%) from the 0.1%/80° C. sample.

Example 11. Study of API without Excipients on Fibrous Structure Loading

Figure 13:
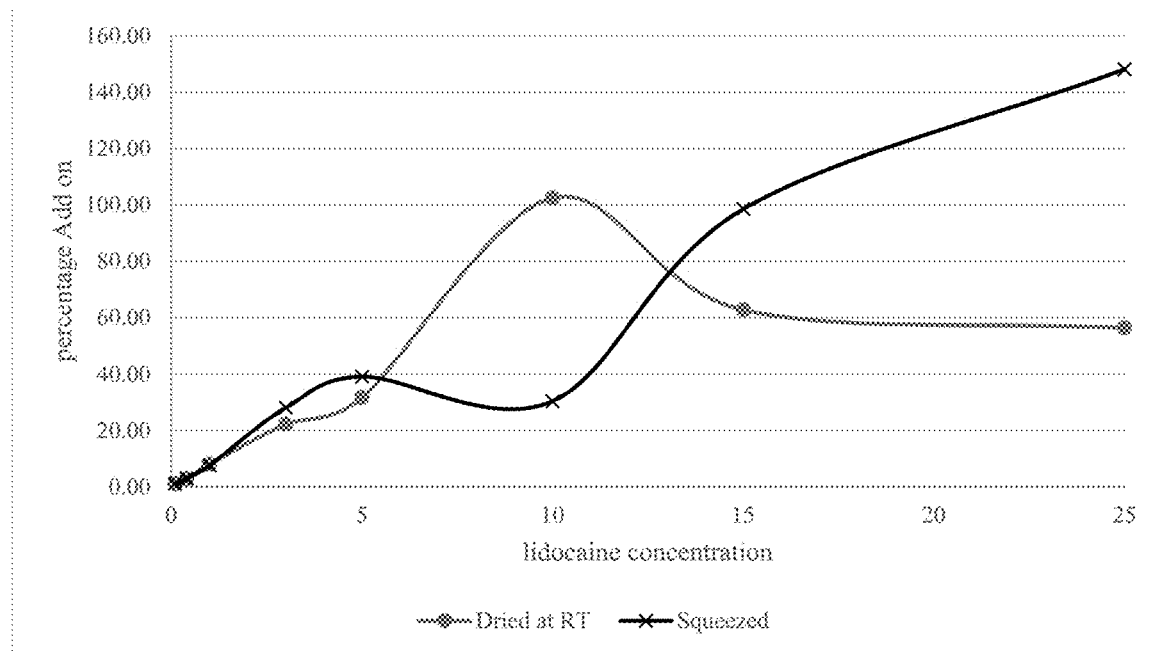
FIG. 13 depicts percentage Add-on of lidocaine, without added excipients in the finishing composition.
Figure 14:
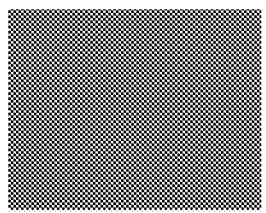
FIG. 14A depicts loading kinetics sample shape A.
FIG. 14B depicts loading kinetics sample shape B.
FIG. 14C depicts loading kinetics sample shape C.
FIG. 14D depicts loading kinetics sample shape D.
Figure 14:
Figure 14:
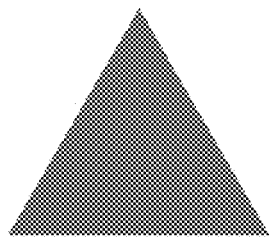
Figure 14:
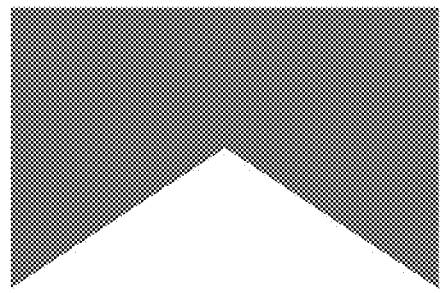
Figure 15:
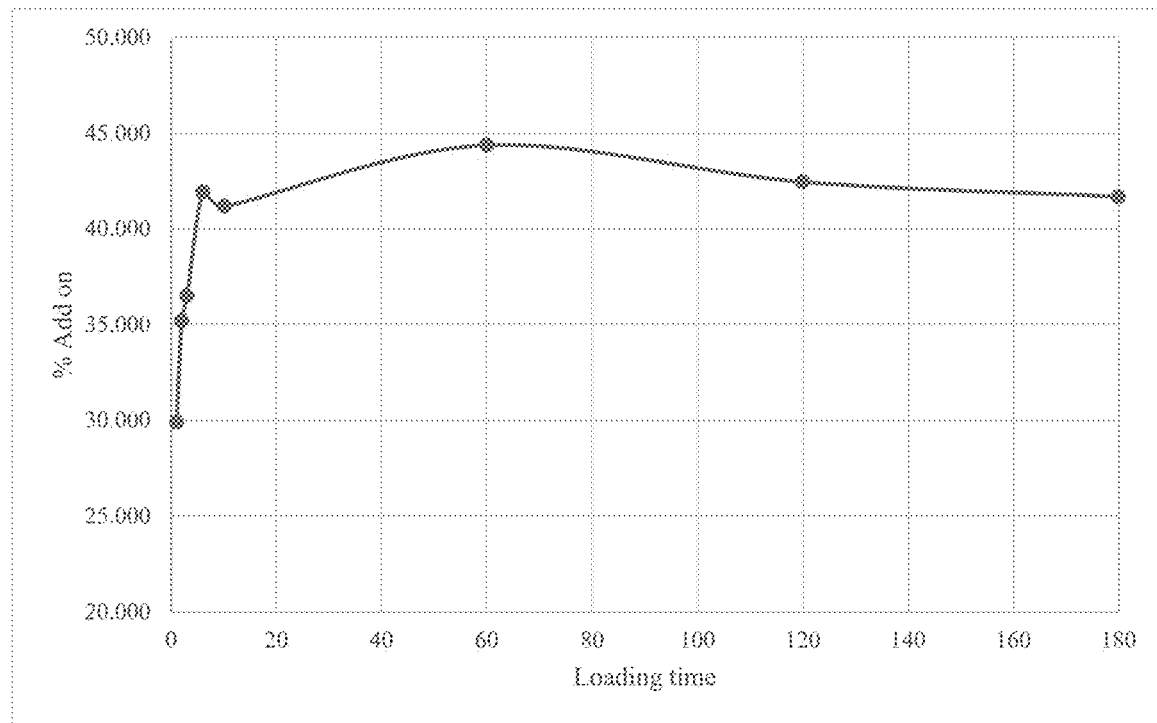
FIG. 15 depicts percentage Add-on with increasing loading time.

Aqueous compositions of 200 g of lidocaine at concentrations between 0.1% and 25% without additional excipients were added to were added to 500 ml vessels and placed in a Mathis Labomat, warmed to 60° C. and rotated at 40 PRM. Once the temperature was achieved, samples of 91.4% polyamide/8.6% elastane were added to each vessel. After a further hour, samples were then either a) left to dry at room temperature for 14 hours or b) squeezed—the sample was placed between the 2 layers of blotting paper and pressed for 2 min by the flat plate with a weight of 2.2 kg and then allowed to dry at room temperature for 14 hours. After drying, the sample's dry weight and percentage Add on were determined. The results are shown in Table 6 and FIG. 13.

TABLE 6

| Lidocaine [% w/w] | Dried at RT % Add on | Squeezed % Add on |
| --- | --- | --- |
| 0.1 | 1.03 | 1.09 |
| 0.4 | 2.86 | 2.91 |
| 1 | 8.03 | 7.57 |
| 3 | 22.17 | 28.01 |
| 5 | 31.61 | 39.06 |
| 10 | 102.39 | 30.39 |
| 15 | 62.68 | 98.46 |
| 25 | 56.33 | 148.02 |

The lidocaine concentration in the mother liquor was assayed for the 0.1, 0.4 and 1% samples using HPLC (Luna C18(2), 100 Å, 5 µm, 250×4.6 mm (Phenomenex), mobile phase-water with acetic acid (pH 3.4) (80%) and Acetonitrile (20%), UV detection at 254 nm at room temperature, flow rate of 1.5 mL/min) and found to be 0.457 mg/ml for the 0.1% liquor, 1.489 mg/ml for the 0.4% liquor and 2.659 mg/ml for the 1%° C. liquor indicating that approximately 108.6 mg (54%) of lidocaine was loaded from the 0.1% sample, 502.2 mg (63%) from the 0.4% sample and 1468 mg (73%) from the 1% sample.

Example 12. Study of Humectants on Fibrous Structure Loading

Aqueous compositions of 7 different humectants at concentrations of 5%, 15% and 25% with, or without, lidocaine and 2% Polysorbate 80, were added to 20 ml vessels and placed on controlled temperature 400 RPM stirrer plates and warmed to 60° C. After 20 minutes of stirring, a 0.4 g sample of 91.4% polyamide/8.6% elastane was added to each vessel. After a further hour, the samples were removed from their vessels, squeezed, weighed and left to dry at room temperature for a further 46 hours before their dry weight and percentage Add on were determined. The results are shown in Table 7.

TABLE 7

| Humectant | % Humectant | % Lidocaine | % PS80 | % Add on |
| --- | --- | --- | --- | --- |
| Mannitol | 5 | 10 | 2 | 37.170 |
|  | 15 | 10 | 2 | 52.217 |
|  | 25 | 10 | 2 | 72.422 |
|  | 25 | 0 | 2 | 39.535 |
| Galen IQ Isomalt | 5 | 10 | 2 | 37.890 |
|  | 15 | 10 | 2 | 33.647 |
|  | 25 | 10 | 2 | 68.766 |
|  | 25 | 0 | 2 | 47.002 |
| Sorbitol | 5 | 10 | 2 | 47.573 |
|  | 15 | 10 | 2 | 59.352 |
|  | 25 | 10 | 2 | 73.934 |
|  | 25 | 0 | 2 | 58.072 |
| Propanediol | 5 | 10 | 2 | 37.713 |
|  | 15 | 10 | 2 | 47.087 |
|  | 25 | 10 | 2 | 65.187 |
|  | 25 | 0 | 2 | 30.162 |
| PEG 200 | 5 | 10 | 2 | 40.865 |
|  | 15 | 10 | 2 | 65.060 |
|  | 25 | 10 | 2 | 79.612 |
|  | 25 | 0 | 2 | 37.717 |
| PEG 400 | 5 | 10 | 2 | 34.653 |
|  | 15 | 10 | 2 | 69.424 |
|  | 25 | 10 | 2 | 75.000 |
|  | 25 | 0 | 2 | 34.343 |
| PEG 600 | 5 | 10 | 2 | 42.748 |
|  | 15 | 10 | 2 | 55.025 |
|  | 25 | 10 | 2 | 59.512 |
|  | 25 | 0 | 2 | 39.423 |

Example 13. Study of Different Permeation Enhancers on Fibrous Structure Loading Aqueous compositions of 11 different permeation enhancers at concentrations of 5%, 15% and 25% with, or without, lidocaine and 2% Polysorbate 80, were added to 20 ml vessels and placed on controlled temperature 400 RPM stirrer plates, warmed to 60° C. and divided into 2 groups of compositions. For Group 1 compositions, after 40 minutes of stirring, a 0.4 g sample of 91.4% polyamide/8.6% elastane was added to each vessel. After a further hour, the samples were removed from their vessels, squeezed, weighed and left to dry at room temperature for a further 16 hours before their dry weight and percentage Add on were determined. For Group 2 compositions, after 45 minutes of stirring, a 0.4 g sample of 90% polyamide/10% elastane was added to each vessel. After 2 hours, the samples were removed from their vessels, squeezed, weighed and left to dry at room temperature for a further 66 hours before their dry weight and percentage Add on were determined. The results for Group 1 compositions are shown in Table 8 and for Group 2 compositions in Table 9.

TABLE 8

| Permeation enhancer | % Permeation enhancer | % Lidocaine | % PS80 | % Add on |
| --- | --- | --- | --- | --- |
| Propylene glycol | 5 | 10 | 2 | 38.261 |
|  | 15 | 10 | 2 | 44.975 |
|  | 25 | 10 | 2 | 59.502 |
|  | 25 | 0 | 2 | 31.494 |
| Isopropyl Myristate | 5 | 10 | 2 | 31.982 |
|  | 15 | 10 | 2 | 47.532 |
|  | 25 | 10 | 2 | 50.229 |
|  | 25 | 0 | 2 | 59.529 |
| 2-pyrrolidone 5 carboxylic acid | 5 | 10 | 2 | 36.343 |
|  | 15 | 10 | 2 | 53.616 |
|  | 25 | 10 | 2 | 65.848 |
|  | 25 | 0 | 2 | 94.761 |

TABLE 8-continued

| Permeation enhancer | % Permeation enhancer | % Lidocaine | % PS80 | % Add on |
|---|---|---|---|---|
| EDTA | 5 | 10 | 2 | 58.701 |
| | 15 | 10 | 2 | 65.049 |
| | 25 | 10 | 2 | 118.590 |
| | 25 | 0 | 2 | 80.918 |
| Citric acid | 5 | 10 | 2 | 24.557 |
| | 15 | 10 | 2 | 38.780 |
| | 25 | 10 | 2 | 53.012 |
| | 25 | 0 | 2 | 52.163 |
| Ethanol | 5 | 10 | 2 | 33.333 |
| | 15 | 10 | 2 | 38.902 |
| | 25 | 10 | 2 | 29.754 |
| | 25 | 0 | 2 | 9.534 |
| N-Methyl-2-pyrrolidone | 5 | 10 | 2 | 35.135 |
| | 15 | 10 | 2 | 39.303 |
| | 25 | 10 | 2 | 60.287 |
| | 25 | 0 | 2 | 31.417 |

TABLE 9

| Permeation enhancer | % Permeation enhancer | % Lidocaine | % PS80 | % Add on |
|---|---|---|---|---|
| 2-propanol | 5 | 10 | 2 | 37.084 |
| | 15 | 10 | 2 | 35.469 |
| | 25 | 10 | 2 | 22.628 |
| | 25 | 0 | 2 | 5.470 |
| Glycerol | 5 | 10 | 2 | 44.301 |
| | 15 | 10 | 2 | 55.000 |
| | 25 | 10 | 2 | 80.000 |
| | 25 | 0 | 2 | 51.891 |
| Erythritol | 5 | 10 | 2 | 40.909 |
| | 15 | 10 | 2 | 51.163 |
| | 25 | 10 | 2 | 85.610 |
| | 25 | 0 | 2 | 40.464 |

Example 14. Study of Different Surfactants on Fibrous Structure Loading

Aqueous compositions of 9 different surfactants at concentrations of 0.1%, 5% and 10% with, or without, lidocaine, were added to 20 ml vessels and placed on controlled temperature 400 RPM stirrer plates and warmed to 60° C. After 2 hours of stirring, a 0.4 g sample of 91.4% polyamide/8.6% elastane was added to each vessel. After a further hour, the samples were removed from their vessels, squeezed, weighed and left to dry at room temperature for a further 66 hours before their dry weight and percentage Add on were determined. The results are shown in Table 10.

TABLE 10

| Surfactant | % Surfactant | % Lidocaine | % Add on |
|---|---|---|---|
| Glyceryl mono isostearate/ Polysorbate 80 | 0.1/0.1 | 10 | 92.386 |
| | 5/5 | 10 | 58.186 |
| | 10/10 | 10 | 53.283 |
| | 10/10 | 0 | 61.369 |
| Polysorbate 20 | 0.1 | 10 | 56.934 |
| | 5 | 10 | 72.372 |
| | 10 | 10 | 82.282 |
| | 10 | 0 | 21.945 |
| Polysorbate 40 | 0.1 | 10 | 53.465 |
| | 5 | 10 | 43.000 |
| | 10 | 10 | 54.722 |
| | 10 | 0 | 18.500 |
| Polysorbate 80 | 0.1 | 10 | 67.143 |
| | 5 | 10 | 44.340 |
| | 10 | 10 | 54.306 |
| | 10 | 0 | 19.656 |

TABLE 10-continued

| Surfactant | % Surfactant | % Lidocaine | % Add on |
|---|---|---|---|
| Poloxamer 124 NF | 0.1 | 10 | 62.857 |
| | 5 | 10 | 49.409 |
| | 10 | 10 | 79.853 |
| | 10 | 0 | 21.957 |
| Poloxamer 188 NF | 0.1 | 10 | 45.278 |
| | 5 | 10 | 63.659 |
| | 10 | 10 | 57.627 |
| | 10 | 0 | 17.848 |
| Poloxamer 127 NF | 0.1 | 10 | 54.613 |
| | 5 | 10 | 36.186 |
| | 10 | 10 | 67.482 |
| | 10 | 0 | 18.780 |
| Cremophor RH40 | 0.1 | 10 | 58.621 |
| | 5 | 10 | 37.037 |
| | 10 | 10 | 46.384 |
| | 10 | 0 | 20.581 |
| Kolliphor ELP 35 | 0.1 | 10 | 79.028 |
| | 5 | 10 | 38.308 |
| | 10 | 10 | 47.585 |
| | 10 | 0 | 19.643 |

Example 15: Study of Different Solvents on Fibrous Structure Loading

A 10 g aqueous (70%) ethanol (30%) composition of 10% PEG 400, 10% propylene glycol and 2% Polysorbate 80 together with 10% lidocaine was added to 20 ml vessel and placed on a controlled temperature 400 RPM stirrer plate and warmed to 50° C. After reaching the required temperature, a 0.5 g sample of 91.4% polyamide/8.6% elastane was added to the vessel and mixed for a further hour. The sample was then removed from its vessels weighed and left to dry overnight at room temperature before its dry weight and percentage Add on were determined (percentage Add on—56%).

Example 16: Study of Diclofenac Fibrous Structure Loading 10 g aqueous compositions of 10% Diclofenac sodium salt, 10% PEG 400, 10% propylene glycol and 2% Polysorbate 80 with, or without 20% aqueous ethanol or NaOH 5N, were added to 20 ml vessels and placed on controlled temperature, 400 RPM, stirrer plates and warmed to 60° C. After reaching the required temperature, 0.5 g samples of 91.4% polyamide/8.6% elastane were added to the vessels and mixed for a further hour. The samples were then removed from their vessels, squeezed, weighed and left to dry overnight at room temperature before their dry weight and percentage Add on were determined. The results are shown in Table 11.

TABLE 11

| Concentration ethanol % (w/w) | NaOH | pH | % Add on |
|---|---|---|---|
| — | — | 8.5 | 42.2 |
| 13.6 | — | 8.3 | 44.1 |
| — | 1 drop | 13.2 | 32.0 |
| — | 1 drop | 14.0 | 46.0 |

The diclofenac concentration in the mother liquor was assayed for both samples not containing NaOH using HPLC (Luna C18(2), 100 Å, 5 μm, 250×4.6 mm (Phenomenex), mobile phase—40% water with acetic acid (pH 3.4) and 60% Acetonitrile, UV detection at 210 nm at room temperature, flow rate of 1.5 mL/min) and found to be 93.68 mg/g for the water based liquor and 90.76 mg/g for the ethanol based liquor indicating that approximately 91.4 mg (17%) of diclofenac was loaded from the water based sample and 104.7 mg (18%) from the ethanol based sample.

Example 17: Study of Clotrimazole Fibrous Structure Loading 200 g compositions of either a) 10% Clotrimazole, 20% PEG400, 15% propylene glycol, 5% Polysorbate 80 in 50% aqueous ethanol orb) 10% Clotrimazole, 20% PEG400, 15% propylene glycol, 5% Polysorbate 80 in ethanol were added to 500 ml vessels and placed in a Mathis Labomat, warmed to 60° C. and rotated at 40 PRM. Once the temperature was achieved, 10 g samples of 91.4% polyamide/8.6% elastane were added to each vessel. After a further hour, the samples were then either squeezed and then allowed to dry at room temperature for overnight. After drying, the sample's dry weight and percentage Add on were determined and the mean Clotrimazole content on the sample was calculated for each of the samples. The results are shown in Table 12.

TABLE 12

| Composition | Mean % Add on | RSD | Calculated Clotrimazole % content |
|---|---|---|---|
| a | 65 | 7.29 | 35 |
| b | 46 | 1.16 | 25 |

Example 18: Study of Ibuprofen Fibrous Structure Loading 200 g compositions of either a) 10% Ibuprofen, 10% PEG400, 10% propylene glycol, 2% Polysorbate 80 in 30% aqueous ethanol orb) 10% Ibuprofen, 10% PEG400, 10% propylene glycol, 2% Polysorbate 80 in ethanol were added to 500 ml vessels and placed in a Mathis Labomat, warmed to 60° C. and rotated at 40 PRM. Once the temperature was achieved, 10 g samples of 91.4% polyamide/8.6% elastane were added to each vessel. After a further hour, the samples were then either squeezed and then allowed to dry at room temperature for overnight. After drying, the sample's dry weight and percentage Add on were determined and the mean Ibuprofen content on the sample was calculated for each of the samples. The results are shown in Table 13.

TABLE 13

| Composition | Mean % Add on | RSD | Calculated Ibuprofen % content |
|---|---|---|---|
| a | 27 | 2.69 | 19 |
| b | 78 | 1.42 | 63 |

Example 19. Study of Different Fabrics and Finish Compositions on Fibrous Structure Loading 200 g aqueous compositions of 10% lidocaine, with, or without, 10% PEG 400, 10% propylene glycol and 2% Polysorbate 80, were prepared in 250 ml vessels and placed on controlled temperature 400 RPM stirrer plates, warmed to 60-70° C. After 1 hour minutes of stirring, different fabrics were added to each vessel and the temperature allowed to drop to 55-65° C. After a further hour, the samples were removed from their vessels, squeezed, weighed and left to dry at room temperature for at least 16 hours before their dry weight and percentage Add on were determined. The results are shown in Table 14.

TABLE 14

| Textile | Denier | % PEG 400/PG/PS80 | % Add on |
|---|---|---|---|
| 100% Polyamide | 20 | 10/10/2 | 139.96 |
| | | 0 | 203.95 |
| 97% Polyamide, 3% Elastane | 40 | 10/10/2 | 65.73 |
| | | 0 | 131.20 |
| 90% Polyamide, 10% Elastane | 20 | 10/10/2 | 85.21 |
| | | 0 | 190.79 |
| 88% Polyamide, 12% Elastane | 40 | 10/10/2 | 71.75 |
| | | 0 | 134.36 |
| 63% Polyamide, 37% Elastane | 15 | 10/10/2 | 161.03 |
| | | 0 | 175.05 |
| 72% Polyamide, 16% Elastane, 12% Polyester | 40 | 10/10/2 | 103.70 |
| | | 0 | 167.54 |
| 32% Polyamide, 17% Elastane, 51% Cotton* | — | 10/10/2 | 110.86 |
| | | 0 | 181.74 |
| 100% Cotton | — | 10/10/2 | 60.88 |
| | | 0 | 114.73 |

*experiment run on 100 g composition

Example 20: Study of Fibrous Structure Loading Kinetics 8 different 200 g aqueous compositions containing 10% lidocaine, 10% PEG 400, 10% propylene glycol and 2% Polysorbate 80, were added to 500 ml vessels and placed in a Mathis Labomat, warmed to 60° C. and rotated at 40 PRM. Once the temperature was achieved, pre-cut samples of the shapes, shown in FIGS. 14A-D, of 91.4% polyamide/8.6% elastane were added to each vessel. Vessels were either returned (Group 1, n=5) to the Labomat and mixed at 60° C., or not returned (Group 2, n=3). At time intervals of 1, 2 and 3 minutes, the samples were removed Group 2 vessels and at 6, 10, 60, 120 and 180 minutes from Group 1 vessels. After being removed from the vessels, the samples were squeezed and allowed to dry overnight at room temperature. After drying, the sample's dry weight and percentage Add on were determined. The results are shown in Table 15 and FIGS. 14A, 14B, 14C, 14D, and 15.

TABLE 15

| Loading time/min | % Add on | | | | |
|---|---|---|---|---|---|
| | Combined | Shape A | Shape B | Shape C | Shape D |
| 1 | 29.915 | 29.820 | 27.838 | 30.455 | 31.547 |
| 2 | 35.227 | 34.985 | 36.019 | 34.260 | 35.643 |
| 3 | 36.500 | 37.273 | 36.782 | 35.879 | 36.064 |
| 6 | 41.938 | 42.242 | 44.328 | 40.764 | 40.418 |
| 10 | 41.190 | 39.998 | 44.262 | 40.939 | 39.560 |
| 60 | 44.374 | 45.729 | 41.509 | 48.701 | 41.556 |
| 120 | 42.458 | 42.233 | 43.286 | 43.679 | 40.635 |
| 180 | 41.691 | 42.281 | 40.802 | 42.474 | 41.206 |

Example 21. Study of API and Finish Composition on Fibrous Structure Loading 8 different aqueous compositions with, or without, 3% lidocaine, 10% PEG 400, 10% propylene glycol and/or 2% Polysorbate 80, were added to 500 ml vessels and placed in a Mathis Labomat, warmed to 60° C. and rotated at 40 PRM. Once the temperature was achieved, samples of 91.4% polyamide/8.6% elastane were added to each vessel. After a further hour, the samples were then either a) left to dry at room temperature for more than 60 hours or b) squeezed and then allowed to dry at room temperature for more than 60 hours. After drying, the sample's dry weight and percentage Add on were determined. The results are shown in Table 16 and Table 17.

TABLE 16

| | % (w/w) | | | Mean % Add on (dried at RT) | RSD |
|---|---|---|---|---|---|
| Lidocaine | PEG 400 | Propylene glycol | Polysorbate 80 | | |
| 3 | — | — | — | 37.25 | 22.94 |
| 3 | 10 | — | — | 54.02 | 10.06 |
| 3 | — | 10 | — | 34.89 | 22.05 |
| 3 | — | — | 2 | 19.10 | 0.69 |
| 3 | 10 | 10 | — | 56.37 | 45.06 |
| 3 | 10 | — | 2 | 42.88 | 0.28 |
| 3 | 10 | 10 | 2 | 40.92 | 3.75 |
| 3 | — | 10 | 2 | 19.34 | 0.09 |

TABLE 17

| | % (w/w) | | | Mean % Add on (squeezed) | RSD |
|---|---|---|---|---|---|
| Lidocaine | PEG 400 | Propylene glycol | Polysorbate 80 | | |
| 3 | — | — | — | 20.27 | 17.23 |
| 3 | 10 | — | — | 32.03 | 5.51 |
| 3 | — | 10 | — | 21.14 | 8.27 |
| 3 | — | — | 2 | 14.97 | 3.00 |
| 3 | 10 | 10 | — | 30.01 | 15.54 |
| 3 | 10 | — | 2 | 24.91 | 2.54 |
| 3 | 10 | 10 | 2 | 25.73 | 0.95 |
| 3 | — | 10 | 2 | 14.48 | 1.98 |
| — | — | — | — | −0.17 | −63.70 |
| — | 10 | — | — | 13.07 | 3.20 |
| — | — | 10 | — | −0.28 | −19.83 |
| — | — | — | 2 | 1.96 | 9.47 |
| — | 10 | 10 | — | 13.58 | 0.29 |
| — | 10 | — | 2 | 13.41 | 2.34 |
| — | 10 | 10 | 2 | 15.04 | 5.63 |
| — | — | 10 | 2 | 2.19 | 27.08 |

Example 22. Study of Humectant and Permeation Enhancer Concentration on Fibrous Structure Loading Different 200 g aqueous compositions containing 2-20% PEG 400 or propylene glycol, with, or without, 3% lidocaine and 2% Polysorbate 80, were added to 500 ml vessels and placed in a Mathis Labomat, warmed to 60° C. and rotated at 40 PRM. Once the temperature was achieved, samples of 91.4% polyamide/8.6% elastane were added to each vessel. After a further hour, the samples were then squeezed and then allowed to dry at room temperature for more than 60 hours. After drying, the sample's dry weight and percentage Add on were determined. The results are shown in Table 18.

TABLE 18

| | % (w/w) | | | Mean % Add on | RSD |
|---|---|---|---|---|---|
| Lidocaine | PEG 400 | Propylene glycol | Polysorbate 80 | | |
| — | 2 | — | — | 2.48 | 15.28 |
| — | 8 | — | — | 7.84 | 5.21 |
| — | 15 | — | — | 15.20 | 0.29 |

TABLE 18-continued

| | % (w/w) | | | Mean % Add on | RSD |
|---|---|---|---|---|---|
| Lidocaine | PEG 400 | Propylene glycol | Polysorbate 80 | | |
| — | 20 | — | — | 20.06 | 1.57 |
| — | — | 2 | — | 2.59 | 2.34 |
| — | — | 8 | — | 7.43 | 6.32 |
| — | — | 15 | — | 12.72 | 0.09 |
| — | — | 20 | — | 19.14 | 0.06 |
| 3 | 2 | — | 2 | 16.59 | 0.95 |
| 3 | 8 | — | 2 | 26.06 | 2.15 |
| 3 | 15 | — | 2 | 30.96 | 2.69 |
| 3 | 20 | — | 2 | 37.95 | 5.14 |
| 3 | — | 2 | 2 | 14.96 | 1.49 |
| 3 | — | 8 | 2 | 15.93 | 2.29 |
| 3 | — | 15 | 2 | 14.84 | 0.26 |
| 3 | — | 20 | 2 | 16.03 | 3.45 |

Example 23. Study of Surfactant Concentration on Fibrous Structure Loading 6 different aqueous compositions containing 3% lidocaine together with 2 to 20% Polysorbate 80 or 10% PEG 400 or 10% propylene glycol, were added to 500 ml vessels and placed in a Mathis Labomat, warmed to 60° C. and rotated at 40 PRM. Once the temperature was achieved, samples of 91.4% polyamide/8.6% elastane were added to each vessel. After a further hour, the samples were then squeezed and then allowed to dry at room temperature for 68 hours. After drying, the sample's dry weight and percentage Add on were determined. The results are shown in Table 19.

татQD TABLE 19

| | % (w/w) | | | Mean % Add on (dried at RT) | RSD |
|---|---|---|---|---|---|
| Lidocaine | PEG 400 | Propylene glycol | Polysorbate 80 | | |
| 3 | — | — | 2 | 16.18 | 1.54 |
| 3 | — | — | 5 | 22.89 | 0.90 |
| 3 | — | — | 8 | 21.18 | 2.57 |
| 3 | — | — | 10 | 24.11 | 3.00 |
| 3 | — | — | 15 | 33.29 | 1.26 |
| 3 | — | — | 20 | 38.08 | 6.97 |
| 3 | 10 | — | — | 39.67 | 13.44 |
| 3 | — | 10 | — | 23.99 | 28.13 |

Figure 16:
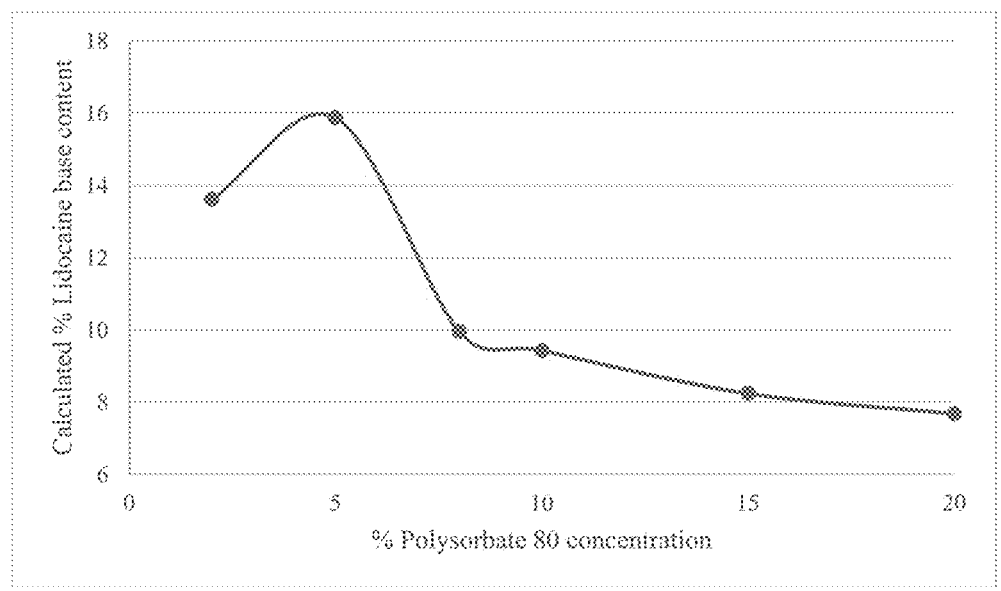
FIG. 16 depicts lidocaine base content with increasing concentration of surfactant.

The mean lidocaine base content on the sample was calculated for each of the Polysorbate 80 samples and the results shown in FIG. 16.

Example 24. Study of pH on Fibrous Structure Loading

Aqueous compositions of 200 g of 10% lidocaine (as the HCl salt), 10% PEG 400, 10% propylene glycol and 2% Polysorbate 80 with their pH tittered by the inclusion of KOH, were added to 500 ml vessels and placed in a Mathis Labomat, warmed to 60° C. and rotated at 40 PRM. After an hour the vessels were removed from the Labomat and samples of 91.4% polyamide/8.6% elastane was added to each vessel at a weight ratio of 1:10, sample:loading composition. Immediately prior to the samples being removed, each loading composition was sampled and the concentration of lidocaine assayed by HPLC. The results are shown in Table 20.

TABLE 20

| | Achieved pH | Concentration of loading composition % w/w |
|---|---|---|
| Loading composition 1 | <0 | 9.93 |
| Loading composition 2 | 2.61 | 9.88 |
| Loading composition 3 | 5.55 | 9.58 |
| Loading composition 4 | 6.18 | 7.44 |
| Loading composition 5 | 7.01 | 6.79 |
| Loading composition 6 | 8.94 | 6.77 |
| Loading composition 7 | 11.26 | 7.79 |
| Loading composition 8 | >14 | 4.53 |

Figure 17:
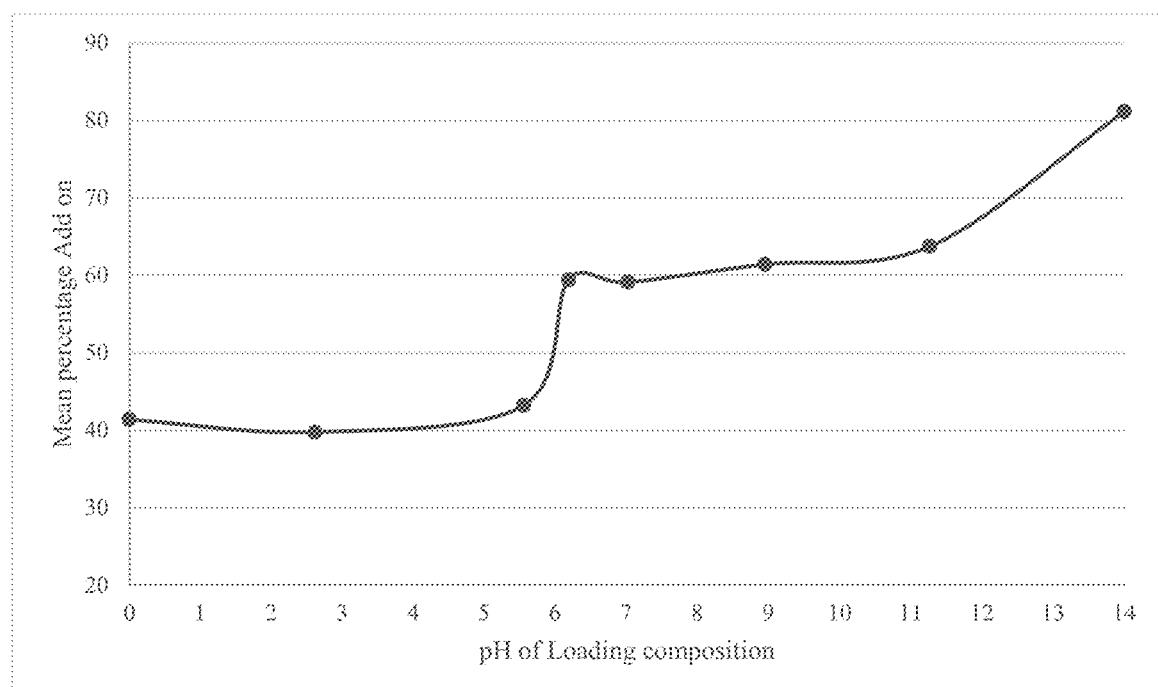
FIG. 17 depicts mean percentage Add-on with increasing pH.
Figure 18A:
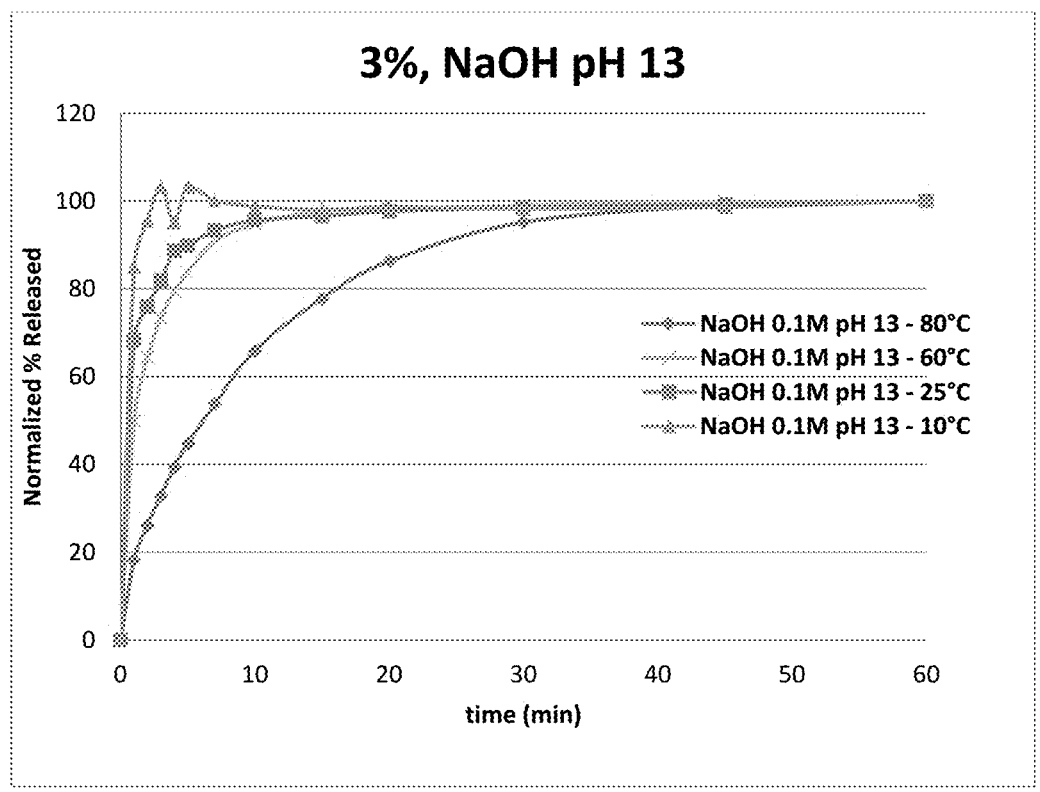
FIG. 18A depicts 3% lidocaine sample dissolution profiles
Figure 18B:
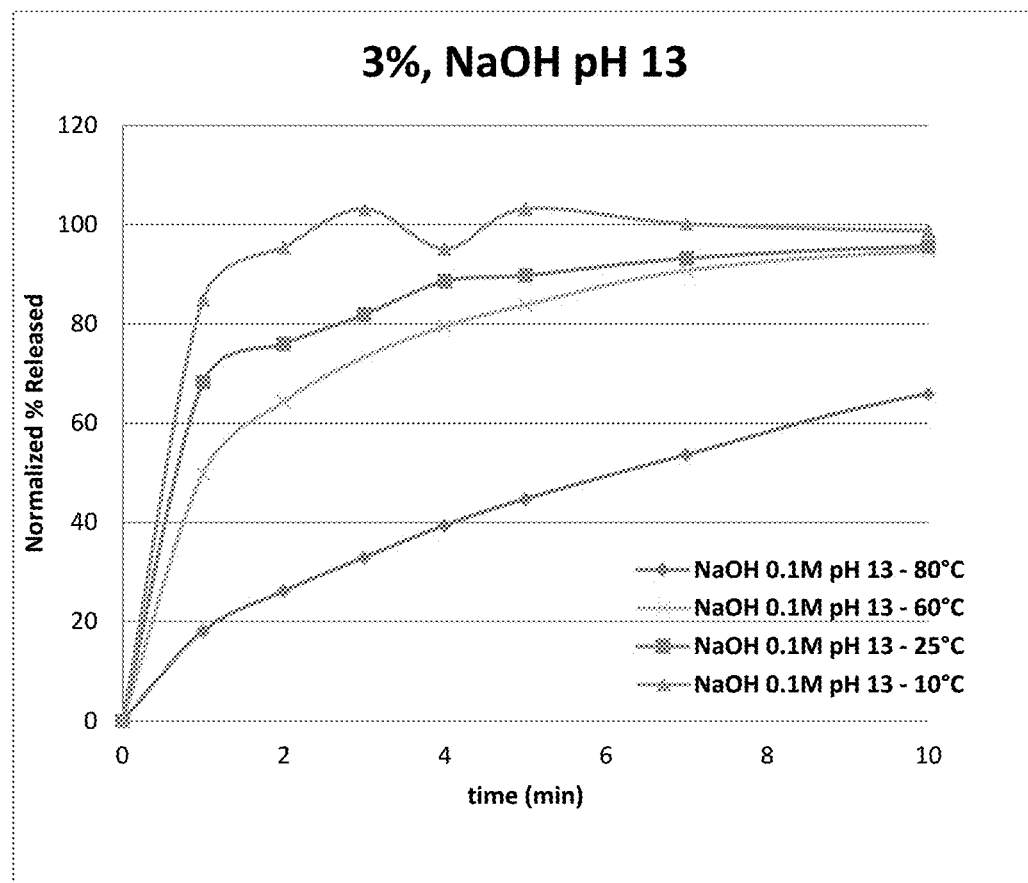
FIG. 18B depicts 3% lidocaine sample dissolution profiles (initial 10 minutes)
Figure 18C:
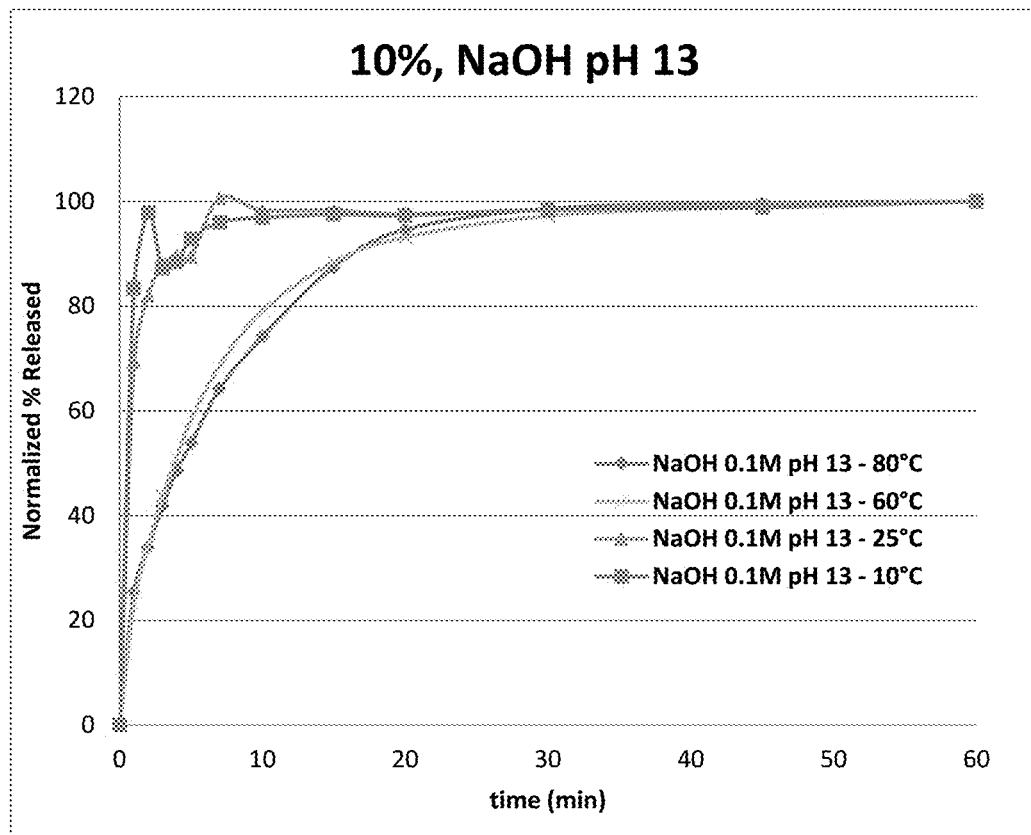
FIG. 18C depicts 10% lidocaine sample dissolution profiles
Figure 18D:
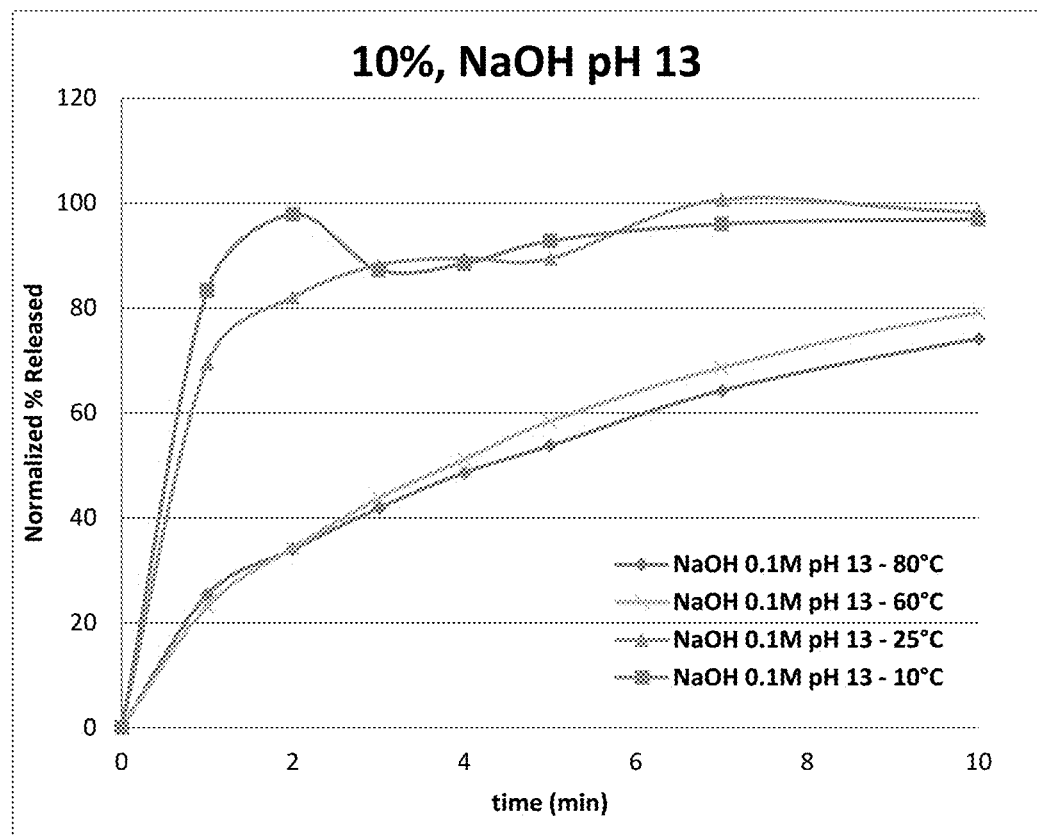
FIG. 18D depicts 10% lidocaine sample dissolution profiles (initial 10 minutes)
Figure 18E:
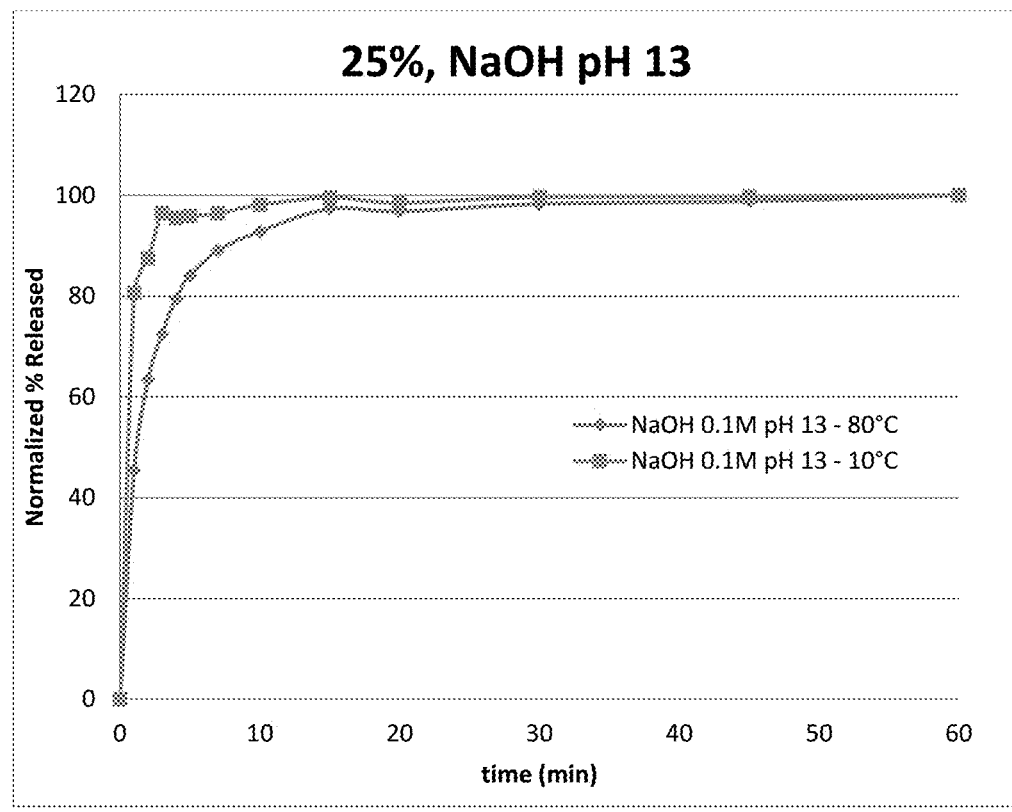
FIG. 18E depicts 25% lidocaine sample dissolution profiles
Figure 18F:
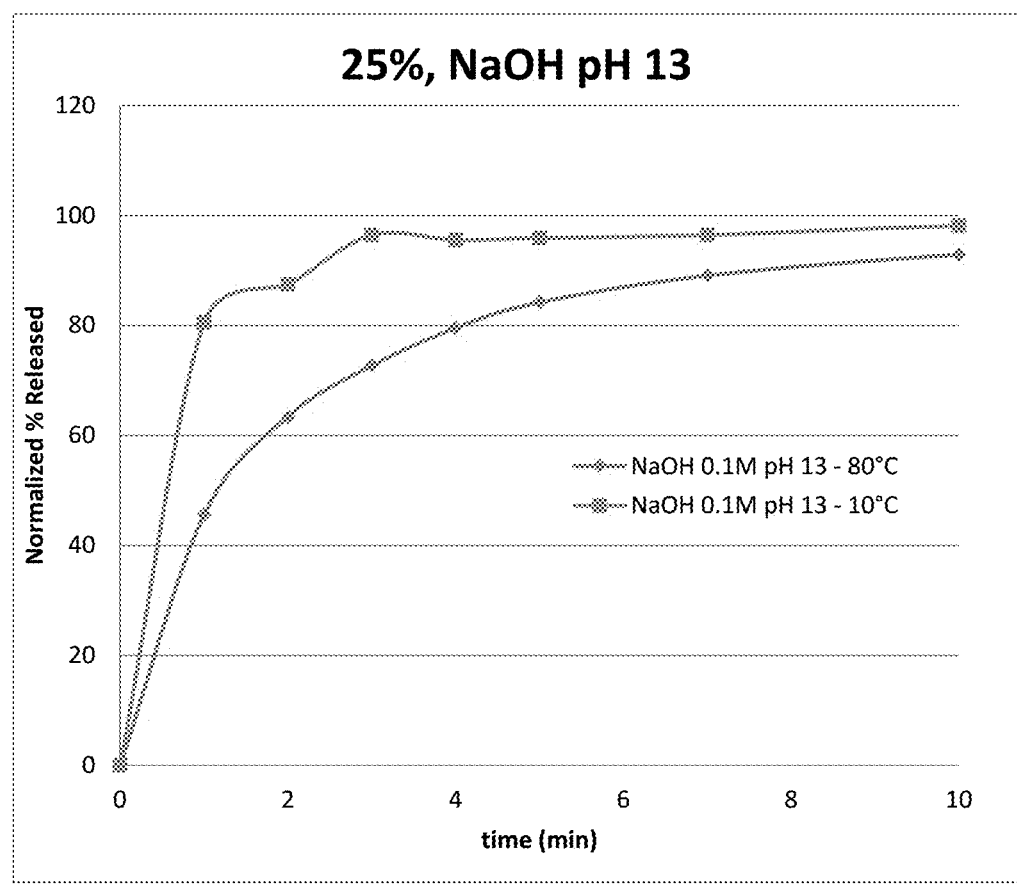
FIG. 18F depicts 25% lidocaine sample dissolution profiles (initial 10 minutes)

After a further hour, the samples were removed from their vessels, squeezed, weighed and left to dry at room temperature for a further 12 hours before their dry weight and percentage Add on were determined. The results are shown in FIG. 17.

Example 25: Study of Fibrous Structure Loading Kinetics and Dissolution 200 g aqueous compositions with 10% PEG 400, 10% propylene glycol, 2% Polysorbate 80 and 3%, 10% or 25% lidocaine, were added to 500 ml vessels and mixed to a controlled temperature. Vessels to be controlled at <10° C. were placed in an ice bath and mixed with a mechanical stirrer for at least 30 minutes. Vessels to be controlled at 60° C. or 80° C. were placed in a Mathis Labomat, warmed to either 60 or 80° C. and rotated at 40 RPM for at least 30 minutes. Once the temperatures were achieved, 20 g samples of 91.4% polyamide/8.6% elastane were added to each vessel. After a further hour, the samples were then squeezed and then allowed to dry overnight at room temperature. After drying, the sample's dry weight and percentage Add on were determined. Using assumptions of 8% (w/w) loading for the 3% lidocaine sample, 25% (w/w) loading for the 10% lidocaine sample and 50% (w/w) loading for the 25% lidocaine sample, 0.5 g, 1 g and 3 g pieces respectively, of the samples were cut off and introduced to a beaker containing 500 ml of 0.1M NaOH (pH 13) and stirred with a mechanical stirrer at 450 RPM. The media was sampled directly by HPLC ((Luna C18(2), 100 Å, 5 µm, 250×4.6 mm (Phenomenex), mobile phase—80% water with acetic acid (pH 3.4) and 20% Acetonitrile, UV detection at 254 nm at room temperature, flow rate of 1.5 mL/min)) at 1, 2, 3, 4, 5, 7, 10, 15, 20, 30, 45 and 60 minutes. The results are shown in FIGS. 18A-18F.

Example 26. Study of Leveling of Fibrous Structure Loading 200 ml aqueous compositions of 10% lidocaine, 10% PEG 400, 10% propylene glycol and 2% Polysorbate 80, were added to 500 ml vessels and placed in a Mathis Labomat, warmed to 60° C. and rotated at 40 PRM. Once the temperature was achieved, samples of 91.4% polyamide/8.6% elastane were added to each vessel. After a further hour, the samples were then squeezed, weighed and allowed to dry at room temperature for more than 60 hours. Samples were then added to 5 separate 20 ml vessels each containing 10 gr 0.01M HCl and placed on 400 RPM, stirrer plates at room temperature. Each sample was mixed for between 1 and 22 hours and then removed, rinsed in about 11 of deionized water and left to dry for 8 hours at room temperature before being weighed. The concentration of lidocaine remaining in each vessel was then identified using HPLC (Luna C18(2), 100 Å, 5 µm, 250×4.6 mm (Phenomenex), mobile phase—80% water with acetic acid (pH 3.4) and 20% Acetonitrile, UV detection at 254 nm at room temperature, flow rate of 1.5 mL/min) and the % lidocaine Add on of each sample calculated. The results are shown in Table 21.

TABLE 21

| Exposure to 0.01M HCl/hr | % lidocaine Add on | RSD |
|---|---|---|
| 1 | 18.86 | 1.91% |
| 2 | 18.07 | |
| 4 | 18.78 | |
| 6 | 18.25 | |
| 22 | 18.04 | |

Example 27. Study of Fibrous Structure Air Permeability

Samples of 91.4% polyamide/8.6% elastane and 100% cotton were loaded, as per the method described in Example 26, with aqueous finishing compositions of lidocaine at concentrations between 0.1% to 20%, together with, or without, 10% PEG 400, 10% propylene glycol and 2% Polysorbate 80. The samples were subsequently weighed and left to dry overnight at room temperature before their dry weight and percentage Add on were determined. Using a modified ASTM D737-09 methodology, the sample's air permeability was tested using a YG461E/II Digital Fabric Air Permeability Tester (Ningbo Textile Instrument Factory). The samples were placed in an atmospheric environment of 25° C. temperature, and 50±2% relative humidity with a test area of 20 cm². The test pressure drop was set to 200 Pa. and nozzles used were 4, 6 (for polyamide samples), and 12 (for cotton samples) and values were measures as the permeation rate of volume (mm/sec). The results are shown in Table 22.

TABLE 22

| Sample | % Add on | Air Permeability mm/sec |
|---|---|---|
| 91.4% polyamide/ 8.6% elastane | 0 | 364 |
| | 17 | 409 |
| | 39 | 333 |
| | 52 | 231 |
| | 69 | 366 |
| 100% Cotton | 16 | 2188 |
| | 20 | 2356 |
| | 33 | 2422 |
| | 61 | 2322 |
| | 91 | 2519 |
| | 138 | 1980 |

Example 28. Study of Fibrous Structure Stiffness

Samples of 91.4% polyamide/8.6% elastane and 100% cotton were loaded, as per the method described in Example 26, with aqueous finishing compositions of lidocaine at concentrations between 0.1% to 20%, together with, or without, 10% PEG 400, 10% propylene glycol and 2% Polysorbate 80. The samples were subsequently weighed and left to dry overnight at room temperature before their dry weight and percentage Add on were determined.

Figure 19:
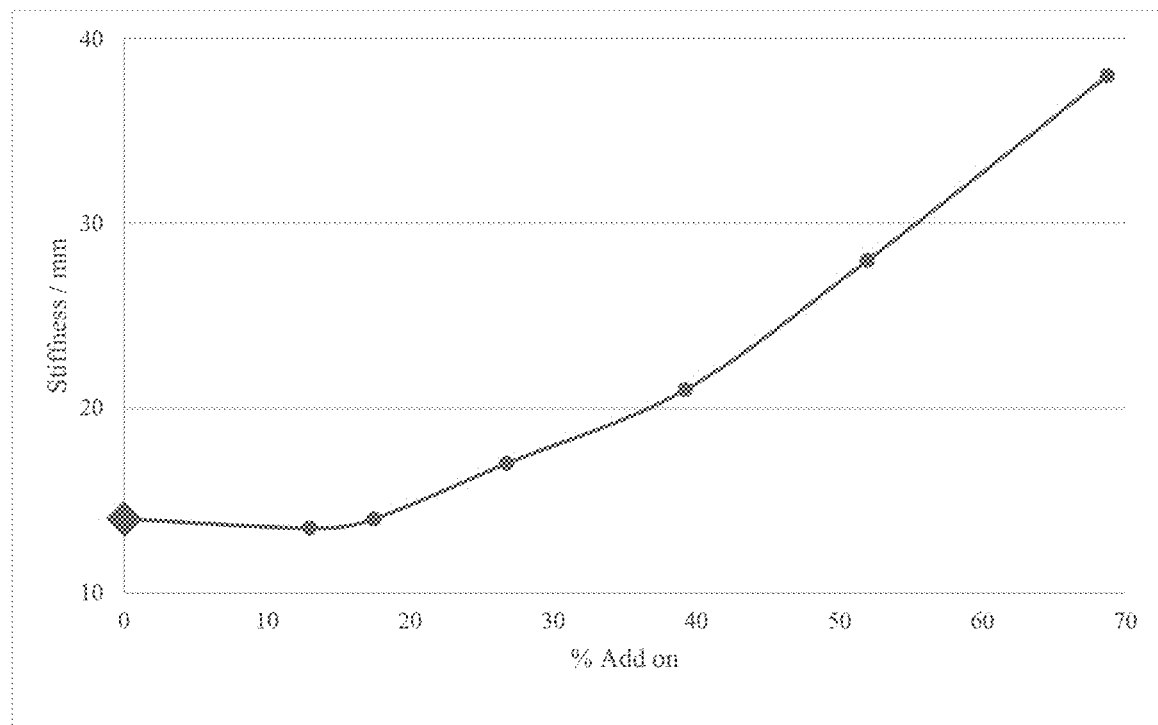

The flexural rigidity of the samples was evaluated using a Shirley Stiffness Tester to measure bending length in millimeters, using a metal ruler to a standard angle of 41.50°. The stiffness test was performed according to ASTM method D1388-18 (Standard Test Method for Stiffness of Fabrics). The bending length was directly obtained by sliding a strip of the sample (2.5 cm wide and 5 cm long) out of the smooth low friction, flat surface platform and letting the fabric tip drape to the plane with a deflection angle below the horizontal of 41.5°. The length of fabric required to bend to this angle is recorded. The greater the length, the greater the fabric's resistance to bend. The results are shown in Table 23 and FIG. 19.

TABLE 23

| Sample | % Add on | Stiffness/mm |
|---|---|---|
| 91.4% polyamide/8.6% elastane | 0 | 14 |
|  | 13 | 14 |
|  | 17 | 14 |
|  | 27 | 17 |
|  | 39 | 21 |
|  | 52 | 28 |
|  | 69 | 38 |
| 100% Cotton | 0 | 22 |
|  | 16 | 21 |
|  | 20 | 21 |
|  | 33 | 26 |
|  | 61 | 36 |
|  | 92 | 39 |
|  | 138 | 68 |

Example 29. Study of Fibrous Structure Tensile Properties

Samples of 91.4% polyamide/8.6% elastane or 100% cotton were loaded, as per the method described in Example 26, with aqueous finishing compositions of lidocaine at concentrations between 0.1% to 20%, together with, or without, 10% PEG 400, 10% propylene glycol and 2% Polysorbate 80. The samples were subsequently weighed and left to dry overnight at room temperature before their dry weight and percentage Add on were determined.

Figure 20A:
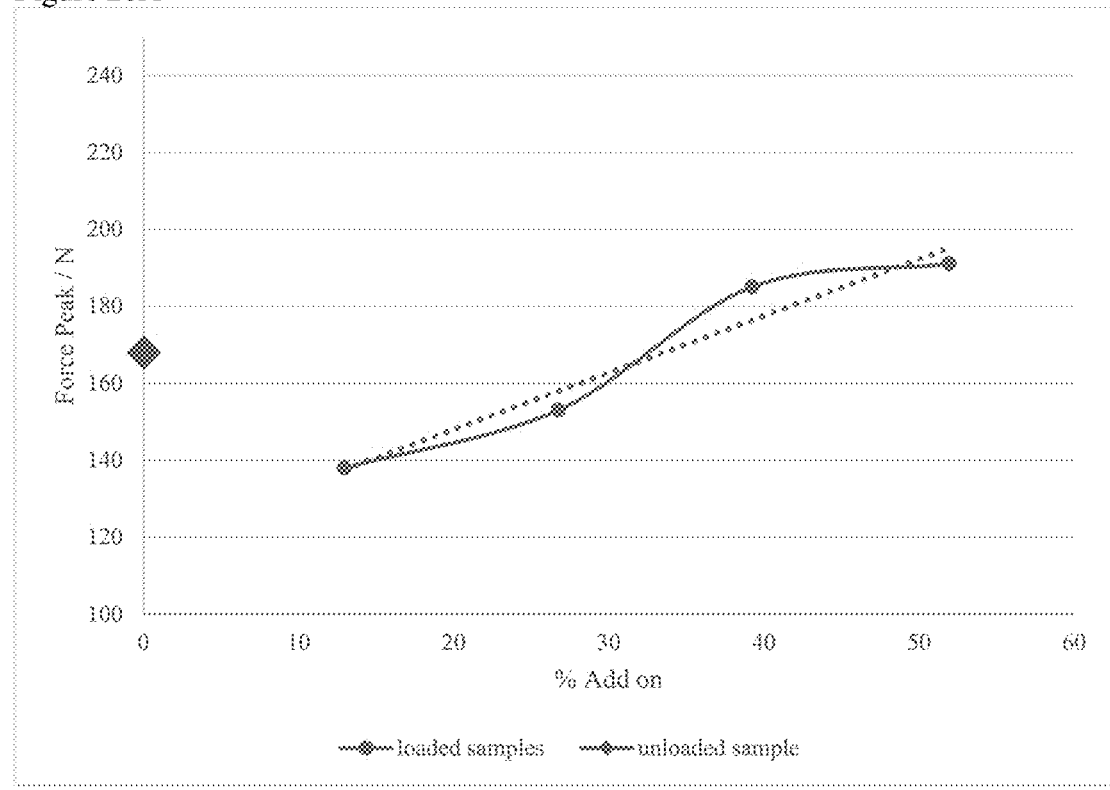
Figure 20B:
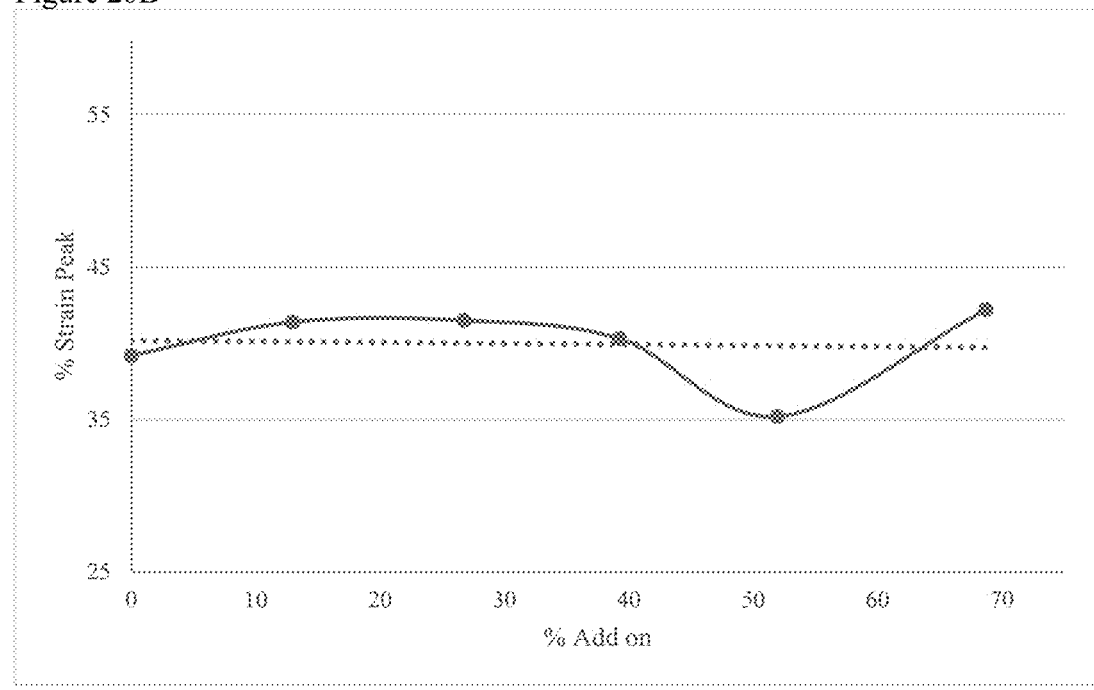

Using a Testometric Tensile Testing Machine M350-10CT (Testometric Co. Ltd., Rochdale, Lancs., England) with a maximum load capacity of 10 kN and according to ASTM D5034-09(2017) test method, the samples' tensile strength and elongation at break (%) were assayed. With all measurements undertaken at 25° C. and 51% RH, the samples were cut into 10 cm×5 cm strips, held with an initial grip separation of 2.5 cm and then pulled apart at a head speed of 300 mm/min. The Force at peak and Strain at peak were recorded by Win-testR analysis software v4.4.5. The results are shown in Table 24 and FIGS. 20A and 20B.

TABLE 24

| Sample | % Add on | Force Peak/N | % Strain Peak |
|---|---|---|---|
| 91.4% polyamide/ 8.6% elastane | 0 | 168 | 39 |
|  | 13 | 138 | 41 |
|  | 17 | 188 | 49 |
|  | 27 | 153 | 42 |
|  | 39 | 185 | 40 |
|  | 52 | 191 | 35 |
|  | 69 | 227 | 39 |
| 100% Cotton | 0 | 217 | 19 |
|  | 16 | 247 | 21 |
|  | 20 | 245 | 25 |
|  | 33 | 261 | 22 |
|  | 61 | 206 | 24 |
|  | 92 | 196 | 25 |
|  | 138 | 226 | 23 |

Figure 21:
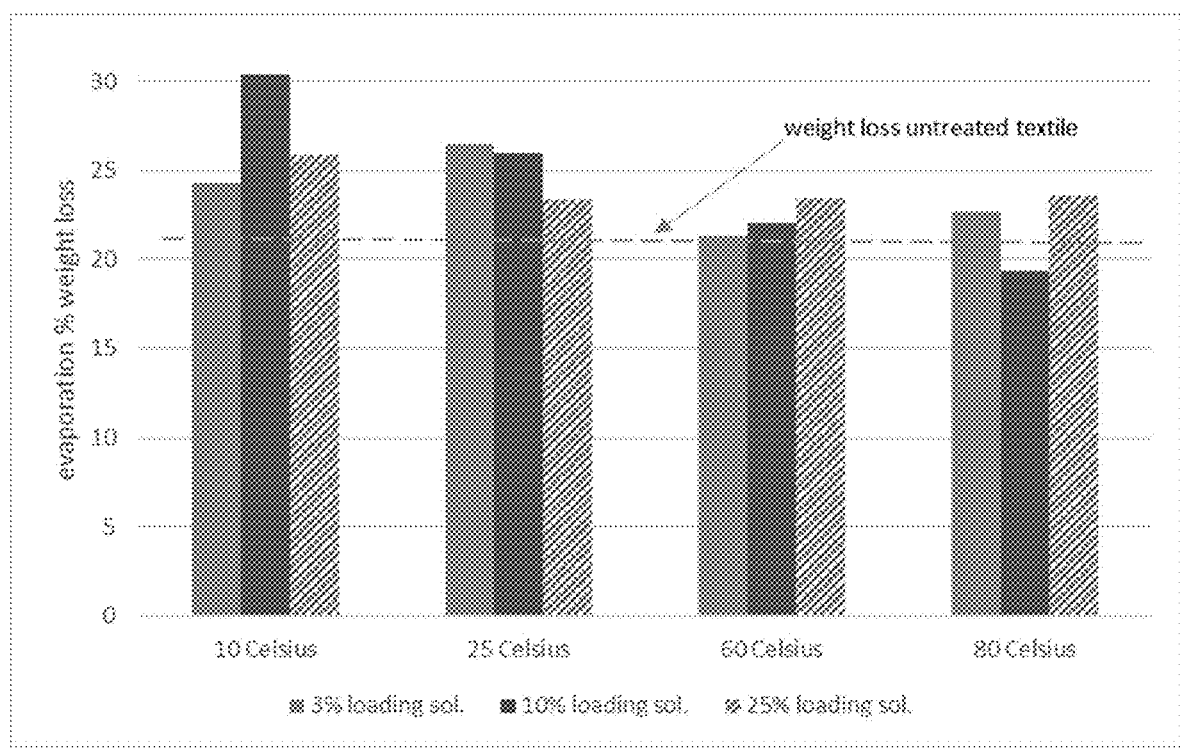
FIG. 21 depicts evaporation % weight loss at 72 hours.

Example 30. Study of Fibrous Structure Moisture Vapor Transmission Rate 200 g aqueous compositions with 10% PEG 400, 10% propylene glycol, 2% Polysorbate 80 and 3%, 10% or 25% lidocaine, were added to 500 ml vessels and mixed to a controlled temperature. Vessels to be controlled at <10° C. were placed in an ice bath and mixed with a mechanical stirrer for at least 30 minutes. Vessels to be controlled at 60° C. or 80° C. were placed in a Mathis Labomat, warmed to either 60 or 80° C. and rotated at 40 RPM for at least 30 minutes. Once the temperatures were achieved, 20 g samples of 91.4% polyamide/8.6% elastane were added to each vessel. After a further hour, the samples were then squeezed and then allowed to dry overnight at room temperature. After drying, the sample's dry weight and percentage Add on were determined. Using a modified ASTM E96-80 methodology, 200 ml of water was added to 500 ml beakers (diameter 75 mm) and closed with the samples, as described above, firmly fixed on top. The beakers were left at 40° C. for 72 hours before being weighed and their percentage evaporation weight loss calculated. The results are shown in FIG. 21.

What is claimed:

1. A method of locally, systemically, or locally and systemically, administering a therapeutically effective amount of an active pharmaceutical ingredient to a subject in need thereof comprising:
    applying a garment that is a mechanically dewatered, finished, non-occlusive, pharmaceutical fibrous structure to the intact skin of the subject for a time sufficient to locally administer, systemically administer, or both locally and systemically administer the therapeutically effective amount of the active pharmaceutical ingredient to the subject,
    the garment comprising natural fibers, manmade fibers, synthetic fibers, or a mixture thereof,
    wherein the garment has been finished with a finishing composition that is a homogeneous dispersion comprising
        an active pharmaceutical ingredient or a pharmaceutically acceptable salt thereof,
        a solvent;
        a surfactant;
        optionally, a humectant; and
        optionally, a permeation enhancer;
    wherein the garment is finished by being caused to interact with the homogeneous dispersion by at least one of diffusion of the homogeneous dispersion into the garment fibers, deposition of the homogeneous dispersion onto the surfaces of the garment fibers, and deposition of the homogeneous dispersion onto the interstices between the garment fibers; and
    wherein the dry weight of the mechanically dewatered, finished, non-occlusive, pharmaceutical fibrous structure is increased at least about 20% Add-on, as compared to the dry weight of the fibrous structure absent the finishing treatment.

2. The method of claim 1 wherein the active pharmaceutical ingredient is lidocaine, prilocaine, bupivacaine, mepivacaine, ropivacaine, articaine, tetracaine, capsaicin, diclofenac, menthol, methyl salicylate, salicylic acid, scopolamine, nitroglycerin, clonidine, estradiol, estradiol/norethidrone, ethinyl estradiol/norelgestromin, estradiol/levonorgestrel fentanyl, nicotine, testosterone, oxybutynin, prilocaine, methylphenidate, betamethasone, buprenorphine, triclocarban, acyclovir, adapalene, allantoin, benzocaine, bexarotene, brimonidine, calcipotriene, calcitriol, ciclopirox, clindamycin, clobetasol, dapsone, diphenhydramine, doxepin, econazole, fluocinolone, fluticasone, halobetasol, hydrocortisone, imiquimod, ingenol, ivermectin, ketoconazole, loteprednol, luliconazole, mafenide, methyl salicylate, metronidazole, miconazole, minoxidil, mometasone, mupirocin, neomycin, nystatin, penciclovir, phenylephedrine, pimecrolimus, pramoxine, selenium, sulconazole, sulfacetamide, tacrolimus, tavaborole, tetracycline, tioconazole, tretinoin, triamcinolone, triclosan, selegiline, rotigotine, rivastigmine, terbinafine, clotrimazole, detomidine, medetomidine, dexmedetomidine, or a combination thereof.

3. The method of claim 1, wherein the garment is applied to the subject's intact skin for a time period that is between about 1 hour and about 72 hours.

4. The method of claim 1, wherein the therapeutically effective amount is administered to the subject throughout the time period.

5. The method of claim 1, wherein the garment is applied to the subject's intact skin continuously throughout the time period.

6. The method of claim 1, wherein the garment is applied to the subject's intact skin intermittently throughout the time period.

7. The method of claim 1, for the treatment of pain.

8. The method of claim 7, wherein the pain is neuropathic pain.

9. The method of claim 7, wherein the pain is postherpetic neuralgia or painful diabetic neuropathy, pain associated with chemotherapy, pain associated with HIV, erythromelalgia, pain associated with osteoarthritis, or lower back pain.

10. The method of claim 1, for the treatment of a microbial infection or a fungal infection.

11. The method of claim 1, for the treatment of an allergy, atopic dermatitis, psoriasis, chronic inflammation, or acute inflammation.

12. The method of claim 1, wherein the garment is finished by being caused to interact with the homogeneous dispersion by diffusion of the homogeneous dispersion into the garment fibers.

13. The method of claim 1, wherein the garment is finished by being caused to interact with the homogeneous dispersion by deposition of the homogeneous dispersion onto the surfaces of the garment fibers.

14. The method of claim 1, wherein the garment is finished by being caused to interact with the homogeneous dispersion by deposition of the homogeneous dispersion onto the interstices between the garment fibers.

15. The method of claim 1, wherein the garment is in the form of a glove, sock, shirt, pant, cap, underpant, brassier, or band.

16. The method of claim 15, wherein the band is an armband, legband, headband, wristband, backbelt, kneeband, ankleband, elbowband, or neckband.

17. The method of claim 1, wherein the garment is in the form of a sock.

18. The method of claim 1, wherein the garment is in the form of a t-shirt.

19. The method of claim 1, wherein the garment is in the form of a glove.

20. The method of claim 1, wherein the garment is in the form of a band.

* * * * *